US011915805B2

(12) United States Patent
Crowley et al.

(10) Patent No.: US 11,915,805 B2
(45) Date of Patent: Feb. 27, 2024

(54) USER INTERFACES FOR SHARED HEALTH-RELATED DATA

(71) Applicant: Apple Inc., Cupertino, CA (US)

(72) Inventors: Matthew W. Crowley, Sunnyvale, CA (US); Nicholas D. Felton, Sunnyvale, CA (US); Tiffany S. Jon, Sunnyvale, CA (US); Kristin M. Canavan, San Francisco, CA (US); Pablo F. Caro, San Francisco, CA (US); Dmitri Cavander, San Francisco, CA (US); Heather E. Daniel, San Jose, CA (US); Christopher D. Lauritzen, San Francisco, CA (US); Charmian B. Naguit, San Francisco, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 17/483,380

(22) Filed: Sep. 23, 2021

(65) Prior Publication Data

US 2022/0392588 A1 Dec. 8, 2022

Related U.S. Application Data

(60) Provisional application No. 63/197,957, filed on Jun. 7, 2021, provisional application No. 63/197,494, filed on Jun. 6, 2021.

(51) Int. Cl.
*G16H 10/60* (2018.01)
*G06F 3/0482* (2013.01)
*G16H 10/40* (2018.01)

(52) U.S. Cl.
CPC ........... *G16H 10/60* (2018.01); *G06F 3/0482* (2013.01); *G16H 10/40* (2018.01)

(58) Field of Classification Search
CPC ....... G16H 10/60; G16H 10/40; G06F 3/0482
USPC ........................................................ 705/2, 3
See application file for complete search history.

(56) References Cited

U.S. PATENT DOCUMENTS

| | | | |
|---|---|---|---|
| 6,416,471 | B1 | 7/2002 | Kumar et al. |
| 6,705,972 | B1 | 3/2004 | Takano et al. |
| 7,128,693 | B2 | 10/2006 | Brown et al. |
| 7,739,148 | B2 | 6/2010 | Suzuki et al. |
| 8,475,339 | B2 | 7/2013 | Hwang et al. |
| 8,676,170 | B2 | 3/2014 | Porrati et al. |
| 8,784,115 | B1 | 7/2014 | Chuang |

(Continued)

FOREIGN PATENT DOCUMENTS

| | | | |
|---|---|---|---|
| CA | 2815518 | A1 | 5/2012 |
| CN | 102448555 | A | 5/2012 |

(Continued)

OTHER PUBLICATIONS

Notice of Allowance received for U.S. Appl. No. 16/894,309, dated Nov. 5, 2021, 12 pages.

(Continued)

*Primary Examiner* — Joshua B Blanchette
(74) *Attorney, Agent, or Firm* — DLA Piper LLP (US)

(57) ABSTRACT

The present disclosure generally relates to user interfaces for managing sharing of health-related data. In some embodiments, user interfaces for establishing sharing of health-related data are described. In some embodiments, user interfaces for viewing and managing shared health-related data are described.

60 Claims, 29 Drawing Sheets

(56) References Cited

U.S. PATENT DOCUMENTS 9,148,483 B1 9/2015 Molettiere et al.
9,224,291 B2 12/2015 Moll-Carrillo et al.
9,557,881 B1 1/2017 Jain et al.
9,589,445 B2 3/2017 White et al.
9,712,629 B2 7/2017 Molettiere et al.
9,813,642 B1 11/2017 Chen et al.
9,940,682 B2 4/2018 Hoffman et al.
10,004,451 B1 6/2018 Proud
10,467,029 B1* 11/2019 Lin ........................ G06F 9/451
2003/0216971 A1 11/2003 Sick et al.
2003/0226695 A1 12/2003 Mault
2004/0210117 A1 10/2004 Ueno et al.
2005/0075214 A1 4/2005 Brown et al.
2005/0079905 A1 4/2005 Martens
2005/0228735 A1 10/2005 Duquette
2005/0272564 A1 12/2005 Pyles et al.
2006/0098109 A1 5/2006 Ooki
2006/0106741 A1 5/2006 Janarthanan
2007/0056727 A1 3/2007 Newman
2007/0179434 A1 8/2007 Weinert et al.
2008/0200312 A1 8/2008 Tagliabue
2008/0300110 A1 12/2008 Smith et al.
2009/0118100 A1 5/2009 Oliver et al.
2009/0210078 A1 8/2009 Crowley
2009/0216556 A1 8/2009 Martin et al.
2009/0262088 A1 10/2009 Moll-Carrillo et al.
2009/0287103 A1 11/2009 Pillai
2010/0048358 A1 2/2010 Tchao et al.
2010/0060586 A1 3/2010 Pisula et al.
2010/0064255 A1 3/2010 Rottler et al.
2010/0121700 A1 5/2010 Wigder et al.
2010/0131298 A1* 5/2010 Buttner .................. G16H 40/67 705/3
2010/0179833 A1 7/2010 Roizen et al.
2010/0273610 A1 10/2010 Johnson
2011/0066051 A1 3/2011 Moon et al.
2011/0071765 A1 3/2011 Yodfat et al.
2011/0087076 A1 4/2011 Brynelsen et al.
2011/0098928 A1 4/2011 Hoffman et al.
2011/0137678 A1 6/2011 Williams
2011/0195383 A1 8/2011 Weiss
2011/0218407 A1 9/2011 Haberman et al.
2011/0275940 A1 11/2011 Nims et al.
2011/0307821 A1 12/2011 Martens
2012/0041767 A1 2/2012 Hoffman et al.
2012/0071770 A1 3/2012 Grey et al.
2012/0116550 A1 5/2012 Hoffman et al.
2012/0253485 A1 10/2012 Weast et al.
2012/0253488 A1 10/2012 Shaw et al.
2012/0283855 A1 11/2012 Hoffman et al.
2012/0316455 A1 12/2012 Rahman et al.
2012/0317167 A1 12/2012 Rahman et al.
2013/0110264 A1 5/2013 Weast et al.
2013/0115583 A1 5/2013 Gordon et al.
2013/0132028 A1 5/2013 Crankson et al.
2013/0151285 A1 6/2013 Mclaren et al.
2013/0197679 A1 8/2013 Balakrishnan et al.
2013/0231575 A1 9/2013 Erkkila et al.
2013/0238287 A1 9/2013 Hoffman et al.
2013/0245966 A1 9/2013 Burroughs et al.
2013/0332286 A1 12/2013 Medelius et al.
2014/0038781 A1 2/2014 Foley et al.
2014/0067096 A1 3/2014 Aibara
2014/0135592 A1 5/2014 Ohnemus et al.
2014/0135955 A1 5/2014 Burroughs
2014/0221790 A1 8/2014 Pacione et al.
2014/0240122 A1 8/2014 Roberts et al.
2014/0244009 A1 8/2014 Mestas
2014/0275852 A1 9/2014 Hong et al.
2014/0336796 A1 11/2014 Agnew
2014/0337451 A1 11/2014 Choudhary et al.
2014/0358012 A1 12/2014 Richards et al.
2014/0371887 A1 12/2014 Hoffman et al.
2015/0057942 A1 2/2015 Self et al.
2015/0067811 A1 3/2015 Agnew et al.
2015/0130830 A1 5/2015 Nagasaki et al.
2015/0142689 A1 5/2015 Squires
2015/0181314 A1 6/2015 Swanson
2015/0182843 A1 7/2015 Esposito et al.
2015/0185967 A1 7/2015 Ly et al.
2015/0196805 A1 7/2015 Koduri et al.
2015/0217163 A1 8/2015 Amis et al.
2015/0220883 A1 8/2015 Bfar et al.
2015/0288797 A1* 10/2015 Vincent .................. G16H 10/60 455/404.2
2015/0347711 A1 12/2015 Soli et al.
2015/0364057 A1 12/2015 Catani et al.
2015/0379198 A1* 12/2015 Tambasco, Jr. ........ G16H 10/60 705/3
2016/0019360 A1 1/2016 Pahwa et al.
2016/0058331 A1 3/2016 Keen et al.
2016/0058336 A1 3/2016 Blahnik et al.
2016/0058337 A1 3/2016 Blahnik et al.
2016/0062464 A1 3/2016 Moussette et al.
2016/0062582 A1 3/2016 Wilson et al.
2016/0135731 A1 5/2016 Drennan
2016/0166195 A1 6/2016 Radecka et al.
2016/0210099 A1 7/2016 Hampapuram et al.
2016/0235374 A1 8/2016 Miller et al.
2016/0250517 A1 9/2016 Tilvis et al.
2016/0256082 A1 9/2016 Ely et al.
2016/0256741 A1 9/2016 Holma et al.
2016/0263435 A1 9/2016 Venkatraman et al.
2016/0324457 A1 11/2016 Dagum
2016/0328991 A1 11/2016 Simpson et al.
2016/0332025 A1 11/2016 Repka
2016/0346607 A1 12/2016 Rapfogel
2016/0373631 A1 12/2016 Titi et al.
2017/0053542 A1 2/2017 Wilson et al.
2017/0075737 A1 3/2017 Kim et al.
2017/0084196 A1 3/2017 Nusbaum et al.
2017/0124276 A1 5/2017 Tee
2017/0161014 A1 6/2017 Kikugawa et al.
2017/0181678 A1 6/2017 Newberry
2017/0215811 A1 8/2017 Newberry
2017/0237694 A1 8/2017 Choudhary et al.
2017/0243508 A1 8/2017 Cheng et al.
2017/0249417 A1 8/2017 Gosieski et al.
2017/0266531 A1 9/2017 Elford et al.
2017/0274267 A1 9/2017 Blahnik
2017/0281057 A1 10/2017 Blahnik et al.
2017/0294174 A1 10/2017 Albadawi et al.
2017/0300186 A1 10/2017 Kuhar et al.
2017/0329933 A1 11/2017 Brust et al.
2017/0348562 A1 12/2017 Jung et al.
2017/0354845 A1 12/2017 Williams et al.
2017/0357520 A1 12/2017 De Vries et al.
2018/0053200 A1* 2/2018 Cronin .................. G16H 20/30
2018/0065025 A1 3/2018 Toda et al.
2018/0074462 A1 3/2018 Helder et al.
2018/0074464 A1 3/2018 Essery et al.
2018/0078182 A1 3/2018 Chen et al.
2018/0137937 A1 5/2018 Gass et al.
2018/0140211 A1 5/2018 Nakazawa et al.
2018/0140927 A1 5/2018 Kito et al.
2018/0226150 A1 8/2018 Hayter et al.
2018/0350451 A1 12/2018 Ohnemus et al.
2019/0104951 A1 4/2019 Valys et al.
2019/0333614 A1 10/2019 Burger et al.
2019/0336044 A1 11/2019 Williams et al.
2019/0336045 A1 11/2019 Williams et al.
2019/0339849 A1 11/2019 Williams et al.
2020/0143258 A1 5/2020 Kanner et al.
2020/0203012 A1 6/2020 Kamath et al.
2020/0261763 A1 8/2020 Park et al.
2020/0297249 A1 9/2020 Williams et al.
2020/0350052 A1 11/2020 Saint et al.
2021/0068714 A1 3/2021 Crowley et al.
2022/0160258 A1 5/2022 Williams et al.
2022/0262485 A1 8/2022 Meschter et al.
2022/0273204 A1 9/2022 Kamath et al.

(56) References Cited

U.S. PATENT DOCUMENTS

| | | | |
|---|---|---|---|
| 2022/0406422 A1 | 12/2022 | Crowley et al. | |
| 2023/0017793 A1 | 1/2023 | Williams et al. | |

FOREIGN PATENT DOCUMENTS

| | | | |
|---|---|---|---|
| CN | 103403627 A | 11/2013 | |
| CN | 106510719 A | 3/2017 | |
| CN | 106537397 A | 3/2017 | |
| CN | 106709235 A | 5/2017 | |
| CN | 107469327 A | 12/2017 | |
| JP | 2004-318503 A | 11/2004 | |
| JP | 2005-79814 A | 3/2005 | |
| JP | 2010-517725 A | 5/2010 | |
| JP | 2010-162297 A | 7/2010 | |
| JP | 2010-181280 A | 8/2010 | |
| JP | 2012-524640 A | 10/2012 | |
| JP | 2013-543156 A | 11/2013 | |
| JP | 2013-544140 A | 12/2013 | |
| JP | 2014-45782 A | 3/2014 | |
| JP | 2014-171831 A | 9/2014 | |
| JP | 2015-28686 A | 2/2015 | |
| JP | 2016-502875 A | 2/2016 | |
| JP | 2016-528016 A | 9/2016 | |
| JP | 2016-177151 A | 10/2016 | |
| JP | 2016-202751 A | 12/2016 | |
| JP | 2017-40981 A | 2/2017 | |
| JP | 2017-134689 A | 8/2017 | |
| JP | 2017-156267 A | 9/2017 | |
| JP | 2017-211994 A | 11/2017 | |
| JP | 2017-532069 A | 11/2017 | |
| KR | 10-2012-0023657 A | 3/2012 | |
| KR | 10-2013-0111569 A | 10/2013 | |
| KR | 10-2013-0111570 A | 10/2013 | |
| KR | 10-2017-0003608 A | 1/2017 | |
| WO | 2009/095908 A2 | 8/2009 | |
| WO | 2010/126825 A1 | 11/2010 | |
| WO | 2012/061438 A2 | 5/2012 | |
| WO | 2012/061440 A2 | 5/2012 | |
| WO | 2013/109916 A1 | 7/2013 | |
| WO | WO-2014144258 A2 * | 9/2014 | ............ A43C 19/00 |
| WO | 2015/027133 A1 | 2/2015 | |
| WO | 2015/198488 A1 | 12/2015 | |
| WO | 2016/036582 A2 | 3/2016 | |
| WO | 2017/037242 A1 | 3/2017 | |

OTHER PUBLICATIONS

Notice of Allowance received for Korean Patent Application No. 10-2021-7038005, dated Dec. 14, 2021, 4 pages (2 pages of English Translation and 2 pages of Official Copy).

Office Action received for Chinese Patent Application No. 202010606407.4, dated Nov. 18, 2021, 6 pages (3 pages of English Translation and 3 pages of Official Copy).

Summons to Attend Oral Proceedings received for European Patent Application No. 20182116.2, mailed on Dec. 21, 2021, 7 pages.

Supplemental Notice of Allowance received for U.S. Appl. No. 16/894,309, dated Dec. 24, 2021, 2 pages.

Office Action received for European Patent Application No. 20203526.7, dated Nov. 23, 2021, 9 pages.

Advisory Action received for U.S. Appl. No. 16/144,849, dated Aug. 12, 2019, 5 pages.

Advisory Action received for U.S. Appl. No. 16/144,864, dated Jul. 6, 2020, 6 pages.

Advisory Action received for U.S. Appl. No. 16/144,864, dated Jul. 29, 2019, 6 pages.

Applicant Initiated Interview Summary received for U.S. Appl. No. 16/144,849, dated Jan. 21, 2020, 6 pages.

Applicant Initiated Interview Summary received for U.S. Appl. No. 16/144,864, dated Apr. 29, 2020, 4 pages.

Applicant Initiated Interview Summary received for U.S. Appl. No. 16/894,309, dated Jan. 26, 2021, 3 pages.

Applicant-Initiated Interview Summary received for U.S. Appl. No. 16/138,809, dated Dec. 16, 2020, 7 pages.

Applicant-Initiated Interview Summary received for U.S. Appl. No. 16/138,809, dated Jun. 9, 2020, 4 pages.

Applicant-Initiated Interview Summary received for U.S. Appl. No. 16/144,864, dated Jun. 22, 2020, 3 pages.

Applicant-Initiated Interview Summary received for U.S. Appl. No. 16/894,309, dated Jun. 25, 2021, 4 pages.

CNET, "Google Fit's automatic activity tracking is getting smarter on Android Wear", Available online at: https://www.youtube.com/watch?v=IttzlCid_d8, May 18, 2016, 1 page.

DC Rainmaker, "Garmin Fenix3 New Auto Climb Functionality", Available online at: https://www.youtube.com/watch?v=iuavOSNpVRc, Feb. 19, 2015, 1 page.

Decision on Appeal received for Korean Patent Application No. 10-2019-7025538, mailed on Feb. 24, 2021, 20 pages (4 pages of English Translation and 16 pages of Official Copy).

Decision to Grant received for Danish Patent Application No. PA201870379, dated Jul. 5, 2019, 2 pages.

European Search Report received for European Patent Application No. 20182116.2, dated Oct. 21, 2020, 4 pages.

Evergreen et al., "Bar Chart", Better Evaluation, Available Online at: https://www.betterevaluation.org/en/evaluation-options/BarChart, Oct. 31, 2014, 8 pages.

Extended European Search Report received for European Patent Application No. 20203526.7, dated Jan. 29, 2021, 13 pages.

Final Office Action received for U.S. Appl. No. 16/138,809, dated Aug. 27, 2020, 24 pages.

Final Office Action received for U.S. Appl. No. 16/144,849, dated Jun. 7, 2019, 29 pages.

Final Office Action received for U.S. Appl. No. 16/144,864, dated May 17, 2019, 24 pages.

Final Office Action received for U.S. Appl. No. 16/144,864, dated May 28, 2020, 29 pages.

Final Office Action received for U.S. Appl. No. 16/894,309, dated Feb. 24, 2021, 30 pages.

Fitbit App, Available online at: http://web.archive.org/web/20180114083150/https://www.fitbit.com/au/app, Jan. 14, 2018, 8 pages.

Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.

Graphs and Charts, Online available at: https://www.teachervision.com/lesson-planning/graph-chart-teacher-resources, retrieved on Dec. 12, 2018, 4 pages.

Intention to Grant received for Danish Patent Application No. PA201870379, dated May 2, 2019, 2 pages.

International Preliminary Report on Patentability received for PCT Patent Application No. PCT/US2019/024570, dated Nov. 19, 2020, 10 pages.

International Search Report and Written Opinion received for PCT Patent Application No. PCT/US2019/024570, dated Aug. 8, 2019, 18 pages.

International Search Report and Written Opinion received for PCT Patent Application No. PCT/US2020/042439, dated Oct. 9, 2020, 14 pages.

Multi-Set Bar Chart, The Data Visualization Catalogue, Available Online at: https://datavizcatalogue.com/methods/multiset_barchart.html, Feb. 8, 2014, 3 pages.

Non-Final Office Action received for U.S. Appl. No. 16/138,809, dated Feb. 28, 2020, 22 pages.

Non-Final Office Action received for U.S. Appl. No. 16/144,849, dated Dec. 31, 2018, 28 pages.

Non-Final Office Action received for U.S. Appl. No. 16/144,849, dated Sep. 17, 2019, 9 pages.

Non-Final Office Action Received for U.S. Appl. No. 16/144,864, dated Dec. 18, 2018, 19 pages.

Non-Final Office Action received for U.S. Appl. No. 16/144,864, dated Jan. 31, 2020, 29 pages.

Non-Final Office Action received for U.S. Appl. No. 16/894,309, dated Oct. 15, 2020, 24 pages.

Notice of Acceptance received for Australian Patent Application No. 2019222943, dated May 5, 2020, 3 pages.

(56) References Cited

OTHER PUBLICATIONS

Notice of Acceptance received for Australian Patent Application No. 2020204153, dated Jul. 6, 2020, 3 pages.
Notice of Acceptance received for Australian Patent Application No. 2020256383, dated Aug. 3, 2021, 3 pages.
Notice of Allowance received for Japanese Patent Application No. 2019-162293, dated Apr. 9, 2021, 4 pages (1 page of English Translation and 3 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for Korean Patent Application No. 10-2020-7026035, dated Aug. 23, 2021, 4 pages (2 pages of English Translation and 2 pages of Official Copy).
Notice of Allowance received for U.S. Appl. No. 16/138,809, dated Apr. 16, 2021, 11 pages.
Notice of Allowance received for U.S. Appl. No. 16/138,809, dated Jul. 20, 2021, 6 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/144,864, dated Feb. 9, 2021, 13 pages.
Notice of Allowance received for U.S. Appl. No. 16/144,864, dated Jul. 28, 2020, 27 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Australian Patent Application No. 2020256383, dated Jun. 4, 2021, 3 pages.
Office Action received for Chinese Patent Application No. 201910858933.7, dated Aug. 18, 2020, 14 pages (7 pages of English Translation and 7 pages of Official Copy).
Office Action received for Chinese Patent Application No. 201910858933.7, dated Jun. 29, 2021, 8 pages (3 pages of English Translation and 5 pages of Official Copy).
Office Action received for Chinese Patent Application No. 202010606407.4, dated Jan. 27, 2021, 16 pages (7 pages of English Translation and 9 pages of Official Copy).
Office Action received for Chinese Patent Application No. 202010606407.4, dated Jun. 2, 2021, 12 pages (5 pages of English Translation and 7 pages of Official Copy).
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for European Patent Application No. 19721883.7, dated Jan. 10, 2020, 4 pages.
Office Action received for European Patent Application No. 19721883.7, dated Jun. 15, 2021, 9 pages.
Office Action received for European Patent Application No. 19721883.7, dated May 28, 2020, 11 pages.
Office Action received for European Patent Application No. 20182116.2, dated May 25, 2021, 9 pages.
Office Action received for European Patent Application No. 20182116.2, dated Nov. 6, 2020, 9 pages.
Office Action received for Japanese Patent Application No. 2018-184532, dated Mar. 1, 2021, 11 pages (6 pages of English Translation and 5 pages of Official Copy).
Office Action received for Japanese Patent Application No. 2019-162293, dated Jan. 31, 2020, 8 pages (4 pages of English Translation and 4 pages of Official Copy).
Office Action received for Japanese Patent Application No. 2019-162293, dated Jul. 27, 2020, 9 pages (5 pages of English Translation and 4 pages of Official Copy).
Office Action received for Japanese Patent Application No. 2020-104679, dated Sep. 18, 2020, 13 pages (7 pages of English Translation and 6 pages of Official Copy).
Office Action received for Korean Patent Application No. 10-2019-7025538, dated Aug. 15, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy).
Office Action received for Korean Patent Application No. 10-2020-7026035, dated Feb. 19, 2021, 13 pages (6 pages of English Translation and 7 pages of Official Copy).
Result of Consultation received for European Patent Application No. 19721883.7, mailed on Oct. 7, 2020, 3 pages.
Rizknows, "TomTom Multisport Cardio Review", Online available at: https://www.youtube.com/watch?v=WoVCzLrSN9A, Sep. 4, 2015, 1 page.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Smith, "Garmin Fenix 5 Activity/Smart Watch Review", Online Available at: https://www.youtube.com/watch?v=6PkQxXQxpoU, Sep. 2, 2017, 1 page.
Sportstechguides, "Garmin Fenix 5: How to Add Power Data Fields", Online Available at: https://www.youtube.com/watch?v=ZkPptnnXEIQ, Apr. 29, 2017, 2 pages.
Sportstechguides, "Garmin Fenix 5: How To Set Up Run Alerts", Online Available at: https://www.youtube.com/watch?v=gSMwv8vlhB4, May 13, 2017, 2 pages.
Supplemental Notice of Allowance received for U.S. Appl. No. 16/144,849, dated Mar. 31, 2020, 2 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan-Heart Rate Zones", Online Available at: https://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at :- https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.

(56) References Cited

OTHER PUBLICATIONS

Visual Pace Alarm app, Available Online at: https://apps.garmin.com/en-US/apps/3940f3a2-4847-4078-a911-d77422966c82, Oct. 19, 2016, 1 page.
Wesley, "Apple Watch Series 1", online available at:- http://toolbox.info/blog/archives/1737-unknown.html, May 28, 2015, 5 pages (Official copy only) (See Communication under 37 CFR § 1.98(a) (3)).
Youtube, "Apple Watch Series 3", Online available at:- https://www.youtube.com/watch?v=iBPr9gEfkK8, Nov. 21, 2017, 15 pages (Official copy only) (See Communication under 37 CFR § 1.98(a) (3)).
Zlelik, "Garmin Fenix 5 Open Water Swimming Activity Demo", Online Available at: https://www.youtube.com/watch?v=iSVhdvw2dcs, Jun. 9, 2017, 1 page.
Notice of Allowance received for U.S. Appl. No. 16/894,309, dated Feb. 25, 2022, 9 pages.
Office Action received for Chinese Patent Application No. 201910858933.7, dated Dec. 30, 2021, 9 pages (4 pages of English Translation and 5 pages of Official Copy).
Brief Communication Regarding Oral Proceedings received for European Patent Application No. 20182116.2, mailed on Apr. 13, 2022, 3 pages.
Supplemental Notice of Allowance received for U.S. Appl. No. 16/894,309, dated Apr. 8, 2022, 3 pages.
International Preliminary Report on Patentability received for PCT Patent Application No. PCT/US2020/042439, dated Jan. 27, 2022, 10 pages.
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Supplemental Notice of Allowance received for U.S. Appl. No. 16/894,309, dated Jan. 25, 2022, 2 pages.
International Search Report and Written Opinion received for PCT Patent Application No. PCT/US2022/030491, dated Sep. 5, 2022, 15 pages.
Applicant-Initiated Interview Summary received for U.S. Appl. No. 16/851,451, dated Nov. 29, 2022, 4 pages.
Intention to Grant received for European Patent Application No. 20182116.2, dated Nov. 11, 2022, 9 pages.
Office Action received for Australian Patent Application No. 2021266294, dated Nov. 11, 2022, 3 pages.
Brief Communication Regarding Oral Proceedings received for European Patent Application No. 20203526.7, mailed on Dec. 23, 2022, 4 pages.
Office Action received for Australian Patent Application No. 2020313970, dated Dec. 22, 2022, 3 pages.
Final Office Action received for U.S. Appl. No. 16/851,451, dated Oct. 20, 2022, 31 pages.
Applicant-Initiated Interview Summary received for U.S. Appl. No. 16/851,451, dated Aug. 5, 2022, 3 pages.
Intention to Grant received for European Patent Application No. 20182116.2, dated Jun. 2, 2022, 8 pages.
Minutes of the Oral Proceedings received for European Patent Application No. 20182116.2, mailed on May 24, 2022, 7 pages.
Non-Final Office Action received for U.S. Appl. No. 16/851,451, dated May 9, 2022, 26 pages.
Notice of Allowance received for Korean Patent Application No. 10-2022-7008569, dated May 19, 2022, 5 pages (2 pages of English Translation and 3 pages of Official Copy).
Summons to Attend Oral Proceedings received for European Patent Application No. 20203526.7, mailed on Jun. 23, 2022, 9 pages.
Brief Communication Regarding Oral Proceedings received for European Patent Application No. 20203526.7, mailed on Jan. 18, 2023, 1 page.
Result of Consultation received for European Patent Application No. 20203526.7, mailed on Jan. 13, 2023, 3 pages.
Non-Final Office Action received for U.S. Appl. No. 16/851,451, dated Feb. 24, 2023, 28 pages.
Non-Final Office Action received for U.S. Appl. No. 17/666,301, dated Feb. 16, 2023, 24 pages.
Notice of Acceptance received for Australian Patent Application No. 2021266294, dated Mar. 3, 2023, 3 pages.
Office Action received for Japanese Patent Application No. 2022-022159, dated Feb. 20, 2023, 10 pages (5 pages of English Translation and 5 pages of Official Copy).
Nakasuji Yoshito, "Apple Watch", First Edition 1st Printing, Japan, Incorporated Company Technical Hyoronsha, Jun. 15, 2015, 4 pages (Official copy only). {See Communication under 37 CFR § 1.98(a) (3)}.
Applicant-Initiated Interview Summary received for U.S. Appl. No. 16/851,451, dated Apr. 20, 2023, 4 pages.
Intention to Grant received for European Patent Application No. 19721883.7, dated May 11, 2023, 9 pages.
Notice of Allowance received for U.S. Appl. No. 17/666,301, dated May 4, 2023, 10 pages.
Supplemental Notice of Allowance received for U.S. Appl. No. 17/666,301, dated May 17, 2023, 2 pages.
Applicant-Initiated Interview Summary received for U.S. Appl. No. 17/666,301, dated Mar. 28, 2023, 4 pages.
Decision to Grant received for European Patent Application No. 20182116.2, dated Mar. 23, 2023, 3 pages.
Office Action received for Australian Patent Application No. 2020313970, dated Mar. 22, 2023, 4 pages.
Office Action received for Japanese Patent Application No. 2022-502594, dated Mar. 20, 2023, 10 pages (5 pages of English Translation and 5 pages of Official Copy).
Intention to Grant received for European Patent Application No. 20203526.7, dated Feb. 10, 2023, 9 pages.
Notice of Allowance received for Chinese Patent Application No. 202210238202.4, dated Jan. 13, 2023, 7 pages (3 pages of English Translation and 4 pages of Official Copy).
Advisory Action received for U.S. Appl. No. 17/952,133, dated Oct. 20, 2023, 7 pages.
Applicant-Initiated Interview Summary received for U.S. Appl. No. 17/952,133, dated Jul. 3, 2023, 4 pages.
Decision to Grant received for European Patent Application No. 19721883.7, dated Aug. 31, 2023, 4 pages.
Decision to Grant received for European Patent Application No. 20203526.7, dated Jun. 22, 2023, 4 pages.
Final Office Action received for U.S. Appl. No. 16/851,451, dated Jun. 1, 2023, 35 pages.
Final Office Action received for U.S. Appl. No. 17/952,133, dated Sep. 26, 2023, 20 pages.
Health Follow-Up with Wearable Medical Device, Vivago Move, XP93061915, Retrieved from the Internet: https://move.vivago.com/en/wearable-medical-devices/#:~:text=Vivago%20MOVETM%20is%20developed,more%20personalized%20and%20timely%20care. [retrieved on Jul. 6, 2023], Jul. 31, 2021, 4 pages.
International Search Report and Written Opinion received for PCT Patent Application No. PCT/US2023/017428, dated Jul. 14, 2023, 17 pages.
Non-Final Office Action received for U.S. Appl. No. 17/952,133, dated Jun. 2, 2023, 28 pages.
Notice of Acceptance received for Australian Patent Application No. 2020313970, dated Jun. 22, 2023, 3 pages.
Notice of Allowance received for Japanese Patent Application No. 2022-022159, dated Aug. 10, 2023, 4 pages (1 page of English Translation and 3 pages of Official Copy).
Notice of Allowance received for Japanese Patent Application No. 2022-502594, dated Jul. 7, 2023, 4 pages (1 page of English Translation and 3 pages of Official Copy).
Office Action received for European Patent Application No. 20751022.3, dated Oct. 19, 2023, 8 pages.
Supplemental Notice of Allowance received for U.S. Appl. No. 17/666,301, dated Jun. 5, 2023, 2 pages.
Vivago Mobile User Manual, XP093061914, Retrieved from the Internet: https://vivago.studio.crasman.fi/pub/web/2016/materials/ladattavat+materiaalit/AEN0007-05_Vivago-MOBILE-User-Manual.pdf [retrieved on Jul. 6, 2023], Jul. 4, 2019, 38 pages.

(56) References Cited

OTHER PUBLICATIONS

International Preliminary Report on Patentability received for PCT Patent Application No. PCT/US2022/030491, dated Dec. 21, 2023, 12 pages.

* cited by examiner

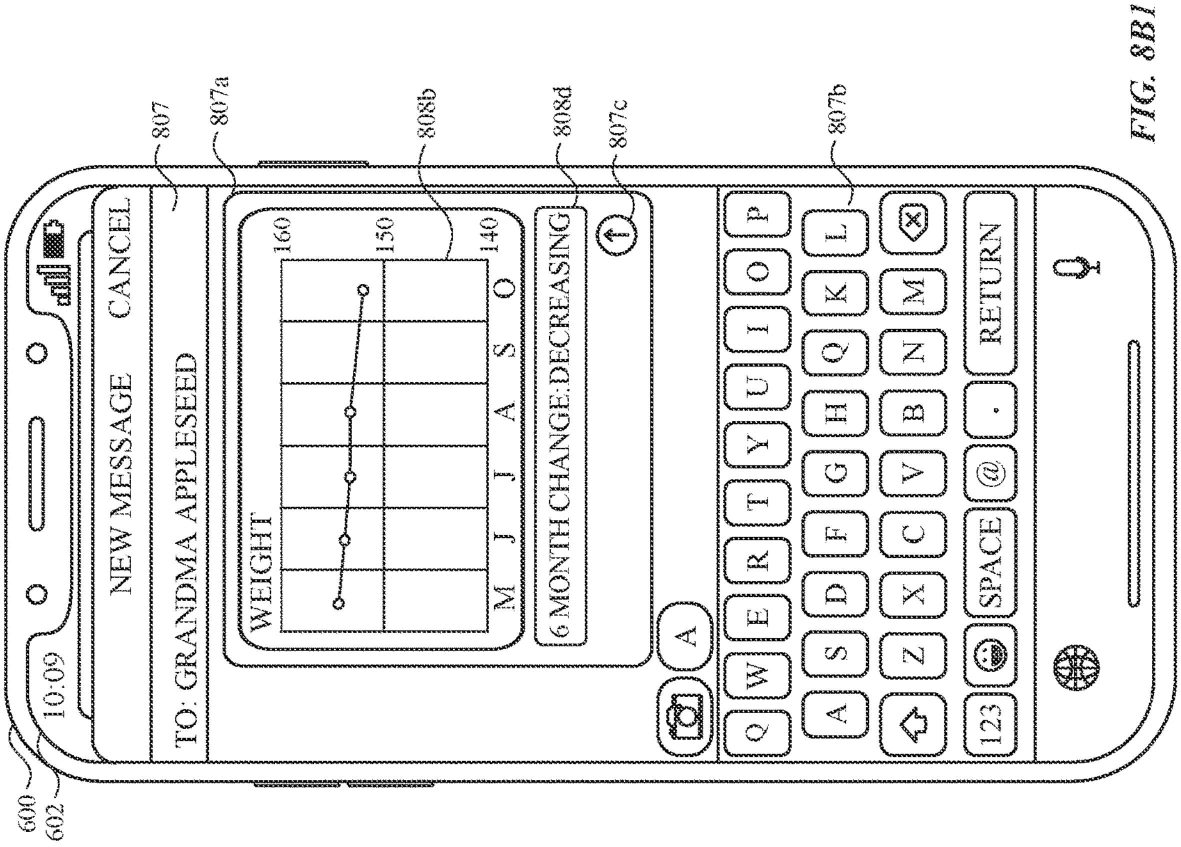
FIG. 8B1

900

902
Display, via the display generation component, a health data sharing user interface that includes a plurality of selectable graphical user interface objects that include:

904
A first selectable user interface object that corresponds to a second user account of a second user that is sharing a first set of health-related data with the first user account.

906
A second selectable user interface object that corresponds to a third user account of a third user that is receiving a second set of health-related data from the first user account.

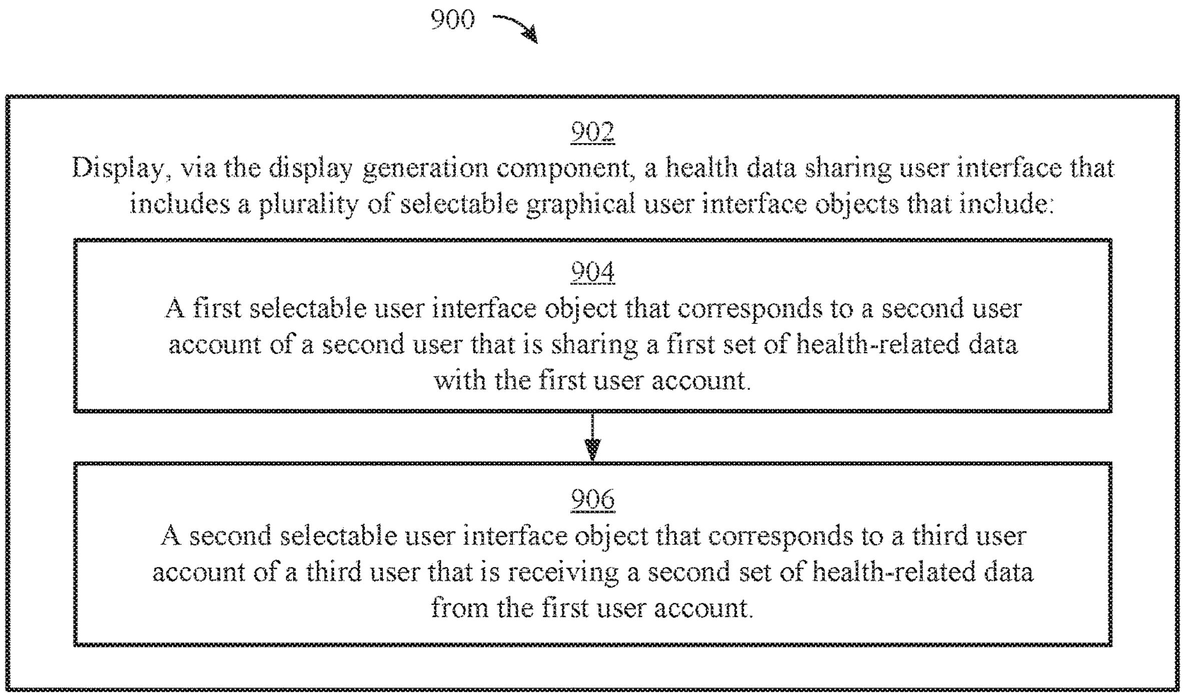

*FIG. 9*

USER INTERFACES FOR SHARED HEALTH-RELATED DATA

CROSS-REFERENCE TO RELATED APPLICATIONS

This application claims priority to U.S. Provisional Application Ser. No. 63/197,494, entitled "USER INTERFACES FOR SHARED HEALTH-RELATED DATA," filed Jun. 6, 2021, and to U.S. Provisional Application Ser. No. 63/197,957, entitled "USER INTERFACES FOR SHARED HEALTH-RELATED DATA," filed Jun. 7, 2021. The content of these applications is hereby incorporated by reference in their entirety.

FIELD

The present disclosure relates generally to computer user interfaces, and more specifically to techniques for managing shared health-related data.

BACKGROUND

Electronic devices collect, store, and access health-related information for users. Such devices provide the user with the ability to manage health information and corresponding functions using the electronic device. Users may select certain health-related information to be shared with family, friends, and/or health institutions via an electronic device.

BRIEF SUMMARY

Some techniques for managing shared health-related data using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for managing shared health-related data. Such methods and interfaces optionally complement or replace other methods for managing shared health-related data. Such methods and interfaces reduce the cognitive burden on a user and produce a more efficient human-machine interface. For battery-operated computing devices, such methods and interfaces conserve power and increase the time between battery charges.

In accordance with some embodiments, a method performed at a computer system that is in communication with a display generation component and one or more input devices is described. The method comprises: receiving, via the one or more input devices, a first set of one or more inputs that correspond to a request to initiate a process for sharing a set of health-related data; and in response to receiving the first set of one or more inputs: displaying, via the display generation component, a first data selection user interface that includes: in accordance with a determination that a first data type satisfies a first set of criteria, a first selectable user interface object that corresponds to the first data type and that, when selected, modifies the sharing status of the first data type in the process for sharing the set of health-related data; and in accordance with a determination that a second data type satisfies the first set of criteria, a second selectable user interface object that corresponds to the second data type and that, when selected, modifies the sharing status of the second data type in the process for sharing the set of health-related data.

In accordance with some embodiments, a non-transitory computer readable storage medium is described. The non-transitory computer-readable storage medium stores one or more programs configured to be executed by one or more processors of a computer system that is in communication with a display generation component and one or more input devices, the one or more programs including instructions for: receiving, via the one or more input devices, a first set of one or more inputs that correspond to a request to initiate a process for sharing a set of health-related data; and in response to receiving the first set of one or more inputs: displaying, via the display generation component, a first data selection user interface that includes: in accordance with a determination that a first data type satisfies a first set of criteria, a first selectable user interface object that corresponds to the first data type and that, when selected, modifies the sharing status of the first data type in the process for sharing the set of health-related data; and in accordance with a determination that a second data type satisfies the first set of criteria, a second selectable user interface object that corresponds to the second data type and that, when selected, modifies the sharing status of the second data type in the process for sharing the set of health-related data.

In accordance with some embodiments, a transitory computer readable storage medium is described. The transitory computer-readable storage medium stores one or more programs configured to be executed by one or more processors of a computer system that is in communication with a display generation component and one or more input devices, the one or more programs including instructions for: receiving, via the one or more input devices, a first set of one or more inputs that correspond to a request to initiate a process for sharing a set of health-related data; and in response to receiving the first set of one or more inputs: displaying, via the display generation component, a first data selection user interface that includes: in accordance with a determination that a first data type satisfies a first set of criteria, a first selectable user interface object that corresponds to the first data type and that, when selected, modifies the sharing status of the first data type in the process for sharing the set of health-related data; and in accordance with a determination that a second data type satisfies the first set of criteria, a second selectable user interface object that corresponds to the second data type and that, when selected, modifies the sharing status of the second data type in the process for sharing the set of health-related data.

In accordance with some embodiments, a computer system that is configured to communicate with a display generation component and one or more input devices is described. The computer system comprises: one or more processors; and memory storing one or more programs configured to be executed by the one or more processors, the one or more programs including instructions for: receiving, via the one or more input devices, a first set of one or more inputs that correspond to a request to initiate a process for sharing a set of health-related data; and in response to receiving the first set of one or more inputs: displaying, via the display generation component, a first data selection user interface that includes: in accordance with a determination that a first data type satisfies a first set of criteria, a first selectable user interface object that corresponds to the first data type and that, when selected, modifies the sharing status of the first data type in the process for sharing the set of health-related data; and in accordance with a determination that a second data type satisfies the first set of criteria, a second selectable user interface object that corresponds to the second data type and that, when selected, modifies the sharing status of the second data type in the process for sharing the set of health-related data.

In accordance with some embodiments, a computer system that is configured to communicate with a display generation component and one or more input devices is described. The computer system comprises: means for receiving, via the one or more input devices, a first set of one or more inputs that correspond to a request to initiate a process for sharing a set of health-related data; and means, responsive to receiving the first set of one or more inputs, for: displaying, via the display generation component, a first data selection user interface that includes: in accordance with a determination that a first data type satisfies a first set of criteria, a first selectable user interface object that corresponds to the first data type and that, when selected, modifying the sharing status of the first data type in the process for sharing the set of health-related data; and in accordance with a determination that a second data type satisfies the first set of criteria, a second selectable user interface object that corresponds to the second data type and that, when selected, modifying the sharing status of the second data type in the process for sharing the set of health-related data.

In accordance with some embodiments, a computer program product is described. The computer program product comprises one or more programs configured to be executed by one or more processors of a computer system that is in communication with a display generation component and one or more input devices. The one or more programs include instructions for: receiving, via the one or more input devices, a first set of one or more inputs that correspond to a request to initiate a process for sharing a set of health-related data; and in response to receiving the first set of one or more inputs: displaying, via the display generation component, a first data selection user interface that includes: in accordance with a determination that a first data type satisfies a first set of criteria, a first selectable user interface object that corresponds to the first data type and that, when selected, modifies the sharing status of the first data type in the process for sharing the set of health-related data; and in accordance with a determination that a second data type satisfies the first set of criteria, a second selectable user interface object that corresponds to the second data type and that, when selected, modifies the sharing status of the second data type in the process for sharing the set of health-related data.

In accordance with some embodiments, a method performed at a computer system that is in communication with a display generation component, wherein the computer system is associated with a first user account of a first user, is described. The method comprises: displaying, via the display generation component, a health data sharing user interface that includes a plurality of selectable graphical user interface objects that include: a first selectable user interface object that corresponds to a second user account of a second user that is sharing a first set of health-related data with the first user account; and a second selectable user interface object that corresponds to a third user account of a third user that is receiving a second set of health-related data from the first user account.

In accordance with some embodiments, a non-transitory computer readable storage medium is described. The non-transitory computer-readable storage medium stores one or more programs configured to be executed by one or more processors of a computer system that is in communication with a display generation component, wherein the computer system is associated with a first user account of a first user, the one or more programs including instructions for: displaying, via the display generation component, a health data sharing user interface that includes one or more selectable graphical user interface objects that include: a first selectable user interface object that corresponds to a second user account of a second user that is sharing a first set of health-related data with the first user account; and a second selectable user interface object that corresponds to a third user account of a third user that is receiving a second set of health-related data from the first user account.

In accordance with some embodiments, a transitory computer readable storage medium is described. The transitory computer-readable storage medium stores one or more programs configured to be executed by one or more processors of a computer system that is in communication with a display generation component, wherein the computer system is associated with a first user account of a first user, the one or more programs including instructions for: displaying, via the display generation component, a health data sharing user interface that includes one or more selectable graphical user interface objects that include: a first selectable user interface object that corresponds to a second user account of a second user that is sharing a first set of health-related data with the first user account; and a second selectable user interface object that corresponds to a third user account of a third user that is receiving a second set of health-related data from the first user account.

In accordance with some embodiments, a computer system that is configured to communicate with a display generation component, wherein the computer system is associated with a first user account of a first user, is described. The computer system comprises: one or more processors; and memory storing one or more programs configured to be executed by the one or more processors, the one or more programs including instructions for: displaying, via the display generation component, a health data sharing user interface that includes one or more selectable graphical user interface objects that include: a first selectable user interface object that corresponds to a second user account of a second user that is sharing a first set of health-related data with the first user account; and a second selectable user interface object that corresponds to a third user account of a third user that is receiving a second set of health-related data from the first user account.

In accordance with some embodiments, a computer system that is configured to communicate with a display generation component, wherein the computer system is associated with a first user account of a first user, is described. The computer system comprises: means for displaying, via the display generation component, a health data sharing user interface that includes one or more selectable graphical user interface objects that include: a first selectable user interface object that corresponds to a second user account of a second user that is sharing a first set of health-related data with the first user account; and a second selectable user interface object that corresponds to a third user account of a third user that is receiving a second set of health-related data from the first user account.

In accordance with some embodiments, a computer program product is described. The computer program product comprises one or more programs configured to be executed by one or more processors of a computer system that is in communication with a display generation component, wherein the computer system is associated with a first user account of a first user. The one or more programs include instructions for: displaying, via the display generation component, a health data sharing user interface that includes one or more selectable graphical user interface objects that include: a first selectable user interface object that corresponds to a second user account of a second user that is sharing a first set of health-related data with the first user account; and a second selectable user interface object that corresponds to a third user account of a third user that is receiving a second set of health-related data from the first user account.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for managing shared health-related data, thereby increasing the effectiveness, efficiency, and user satisfaction with such devices. Such methods and interfaces may complement or replace other methods for managing shared health-related data.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 9 is a flow diagram illustrating a method for display of shared health-related data using a computer system, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for computer systems that provide efficient methods and interfaces for managing shared health-related data. For example, it is advantageous to establish sharing relationships for health-related data between users. Additionally, it is advantageous to notify a user of a change in health-related data of another user. Such techniques can reduce the cognitive burden on a user who shares health-related data, thereby enhancing productivity. Further, such techniques can reduce processor and battery power otherwise wasted on redundant user inputs.

Figure 6A:
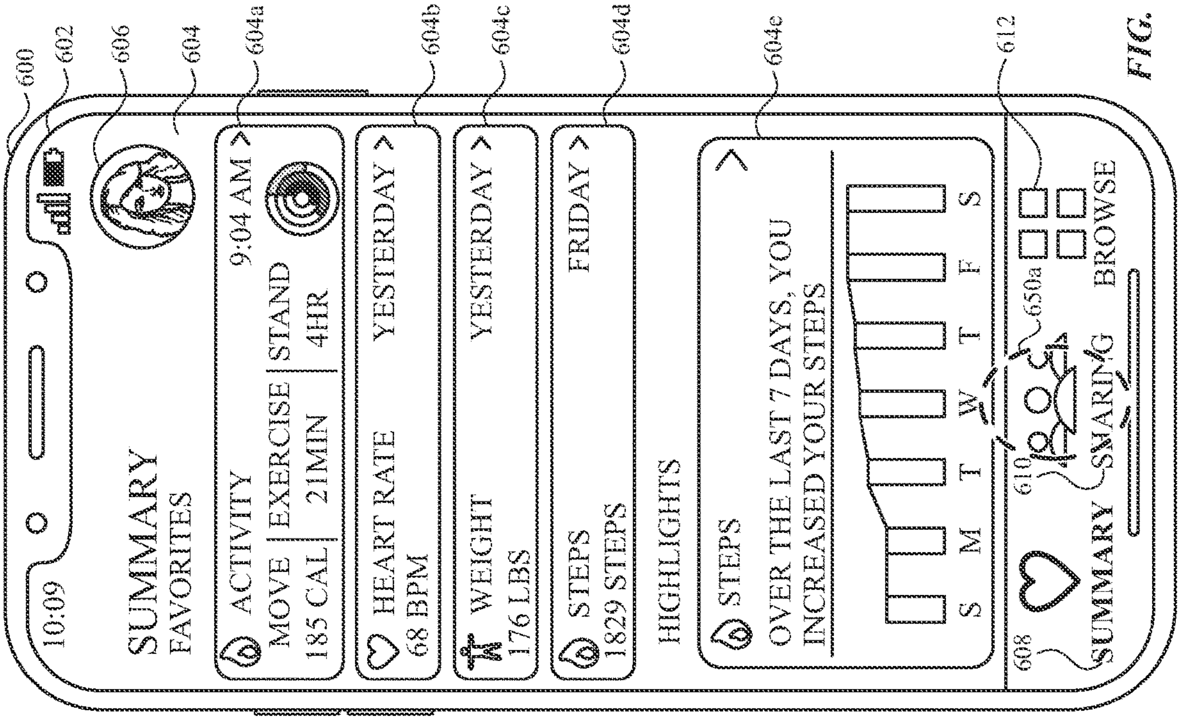
Figure 6T:
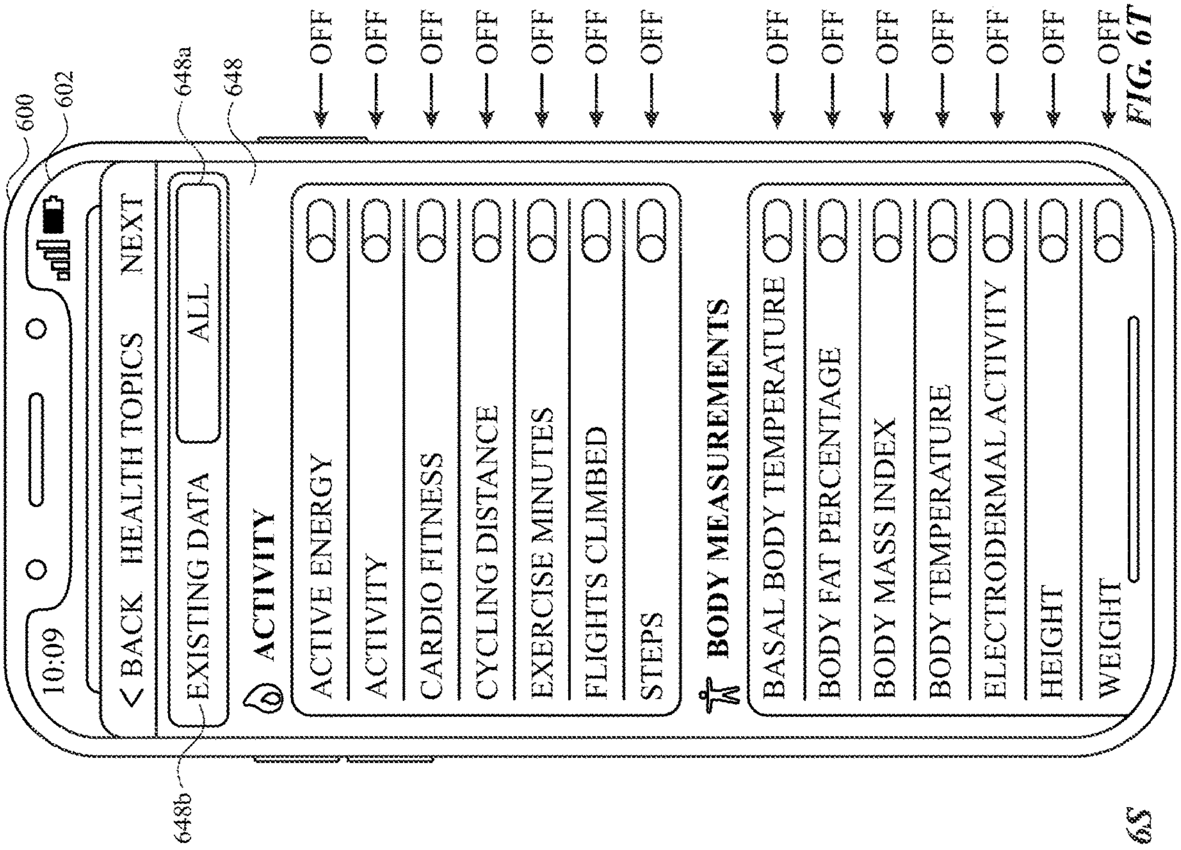
Figure 7:
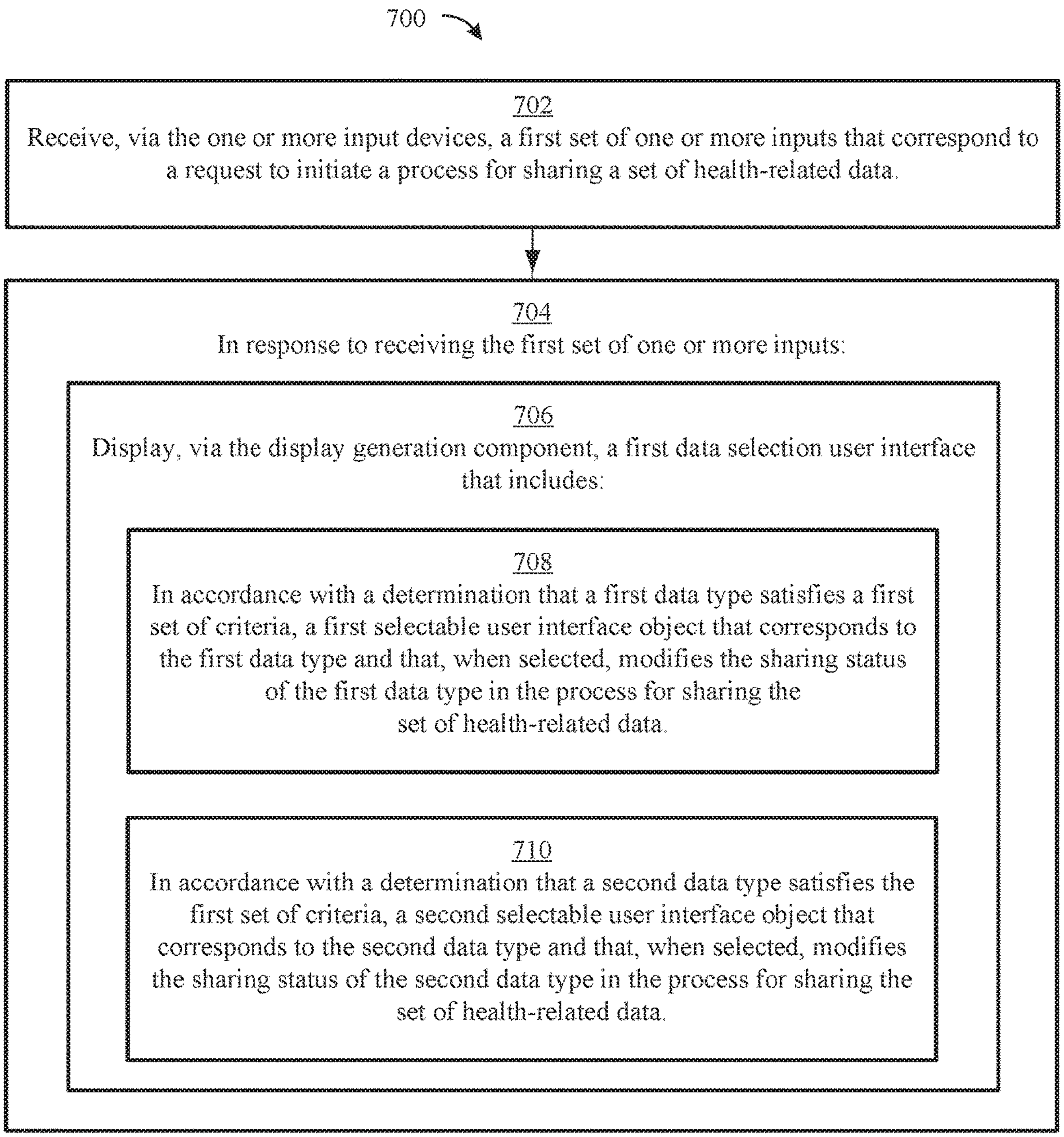
FIG. 7 is a flow diagram illustrating a method for initiating sharing of health-related data using a computer system, in accordance with some embodiments.

Below, FIGS. 1A-1B, 2, 3, 4A-4B, and 5A-5B provide a description of exemplary devices for performing the techniques for managing event notifications. FIGS. 6A-6T illustrate exemplary user interfaces for managing shared health-related data. FIG. 7 is a flow diagram illustrating methods of managing shared health-related data in accordance with some embodiments. The user interfaces in FIGS. 6A-6T are used to illustrate the processes described below, including the processes in FIG. 7. FIGS. 8A-8P illustrate exemplary user interfaces for displaying shared health-related data. FIG. 9 is a flow diagram illustrating methods of displaying shared health-related data in accordance with some embodiments. The user interfaces in FIGS. 8A-8P are used to illustrate the processes described below, including the processes in FIG. 9.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms “first,” “second,” etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
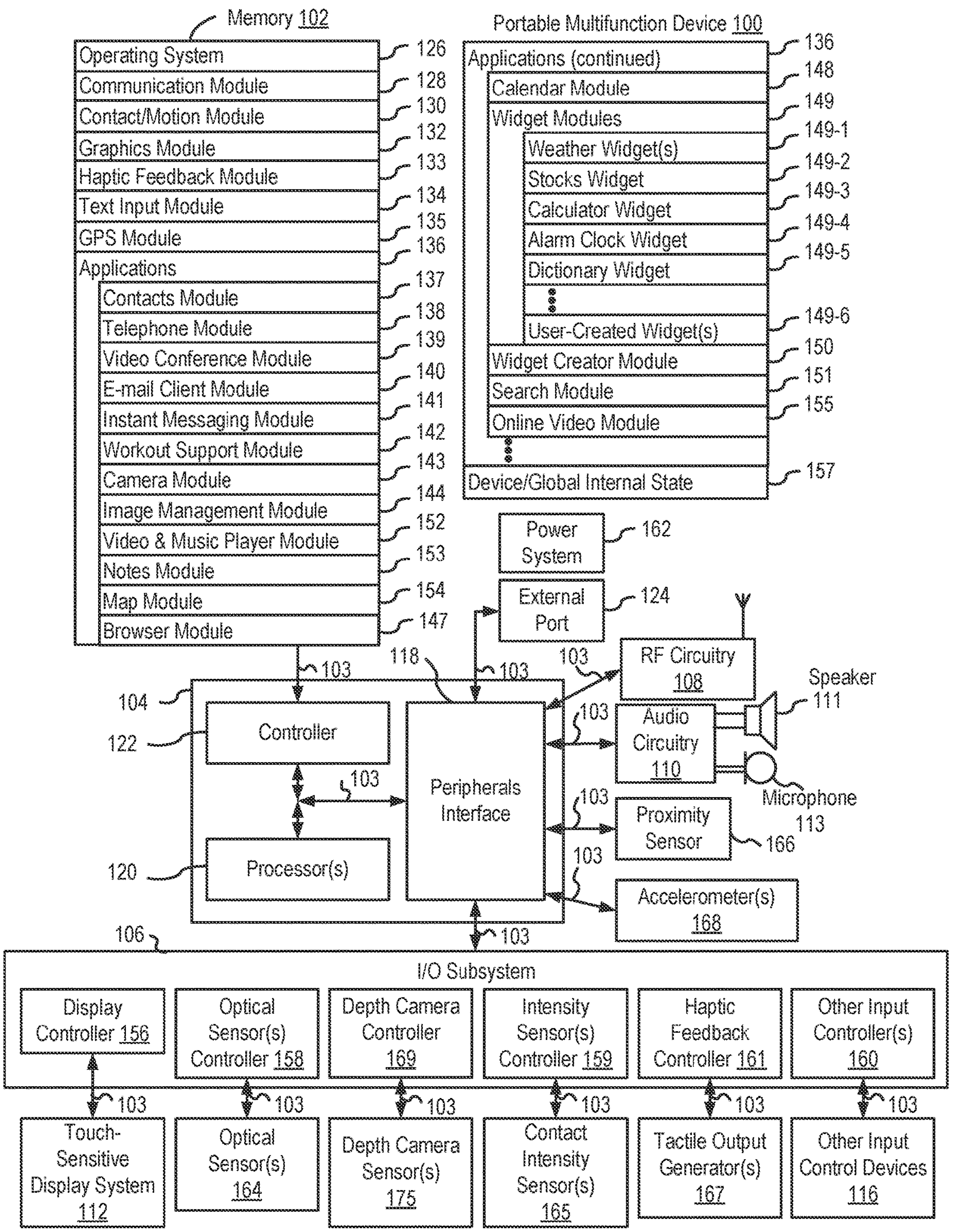
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
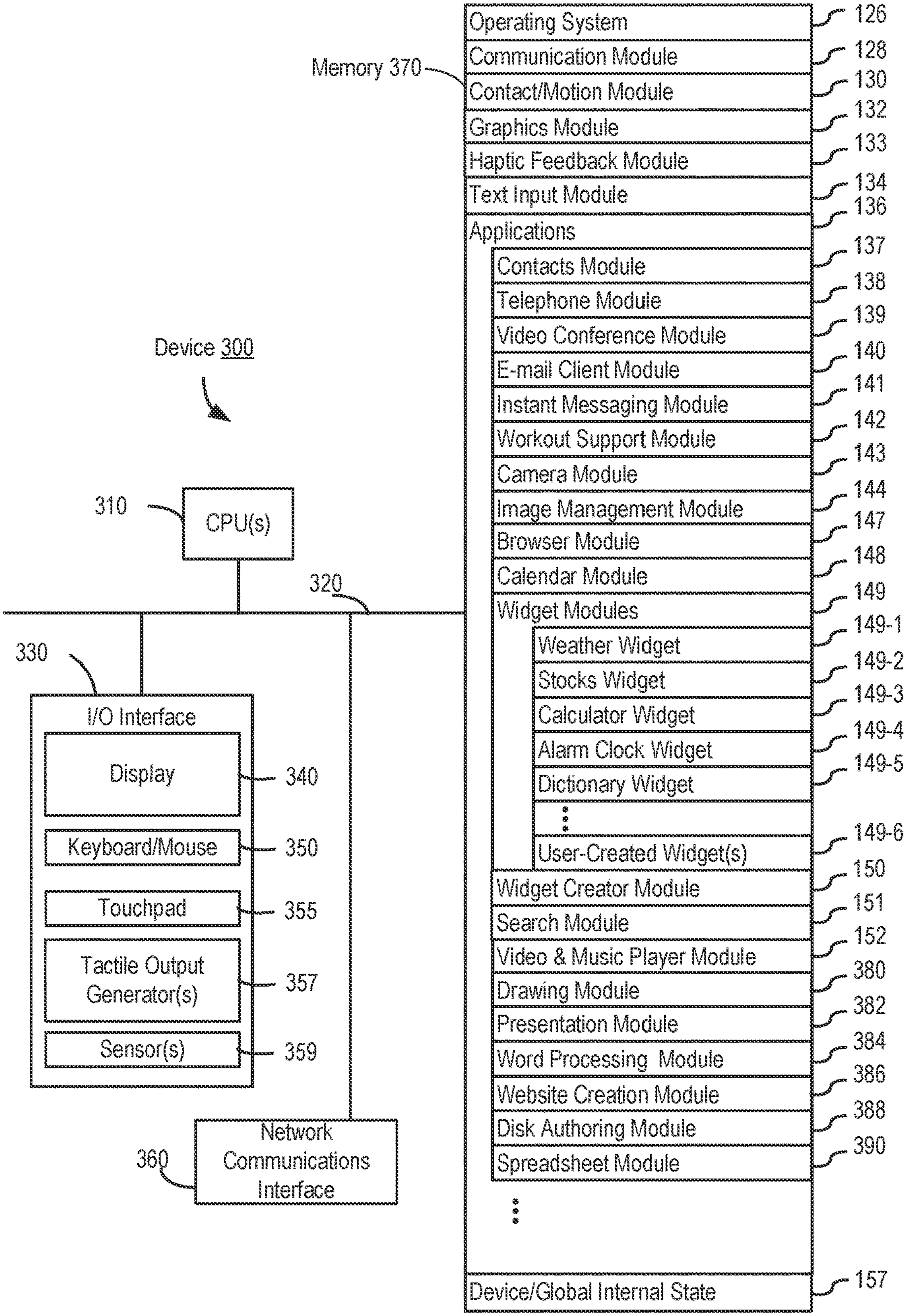
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
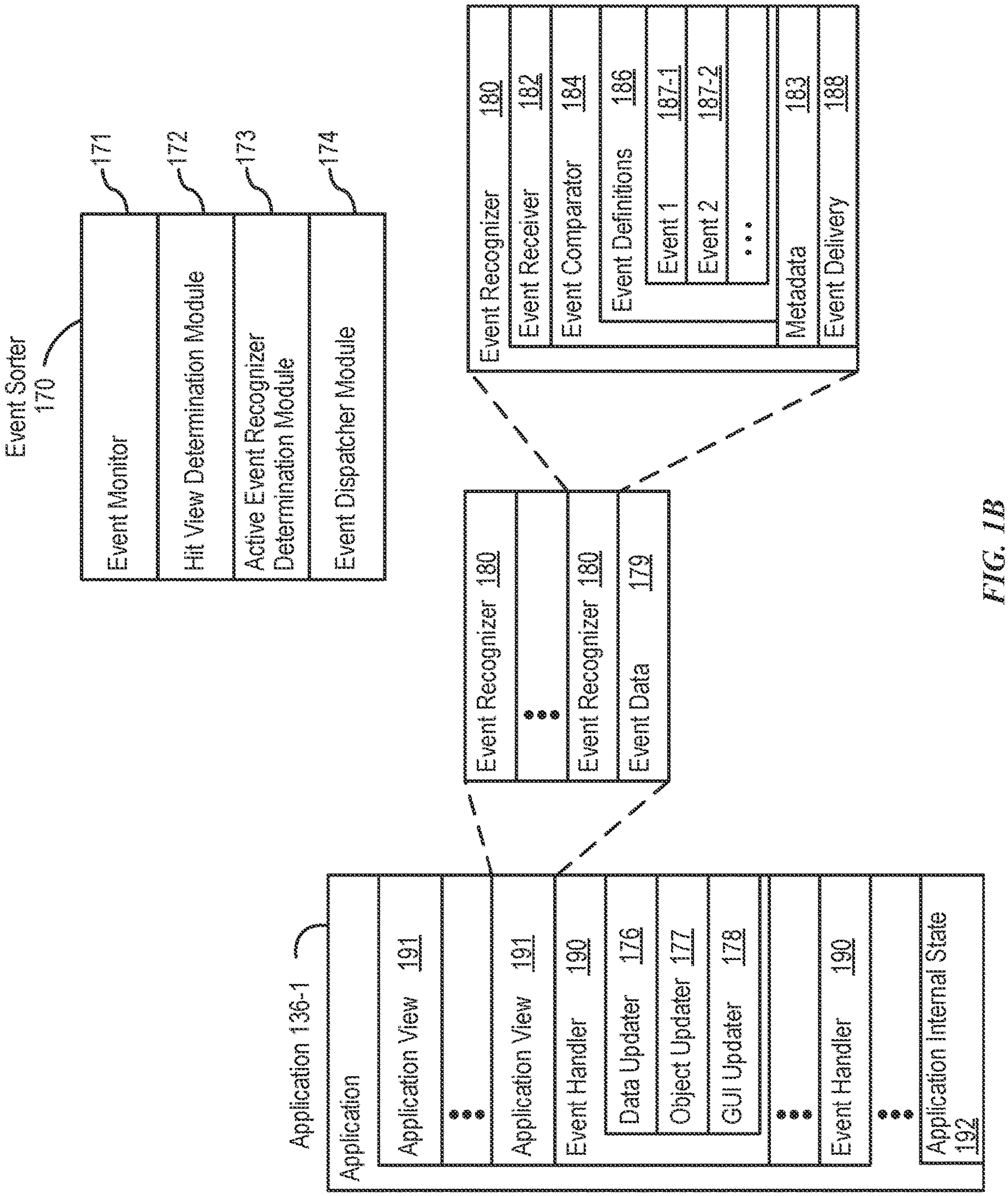
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
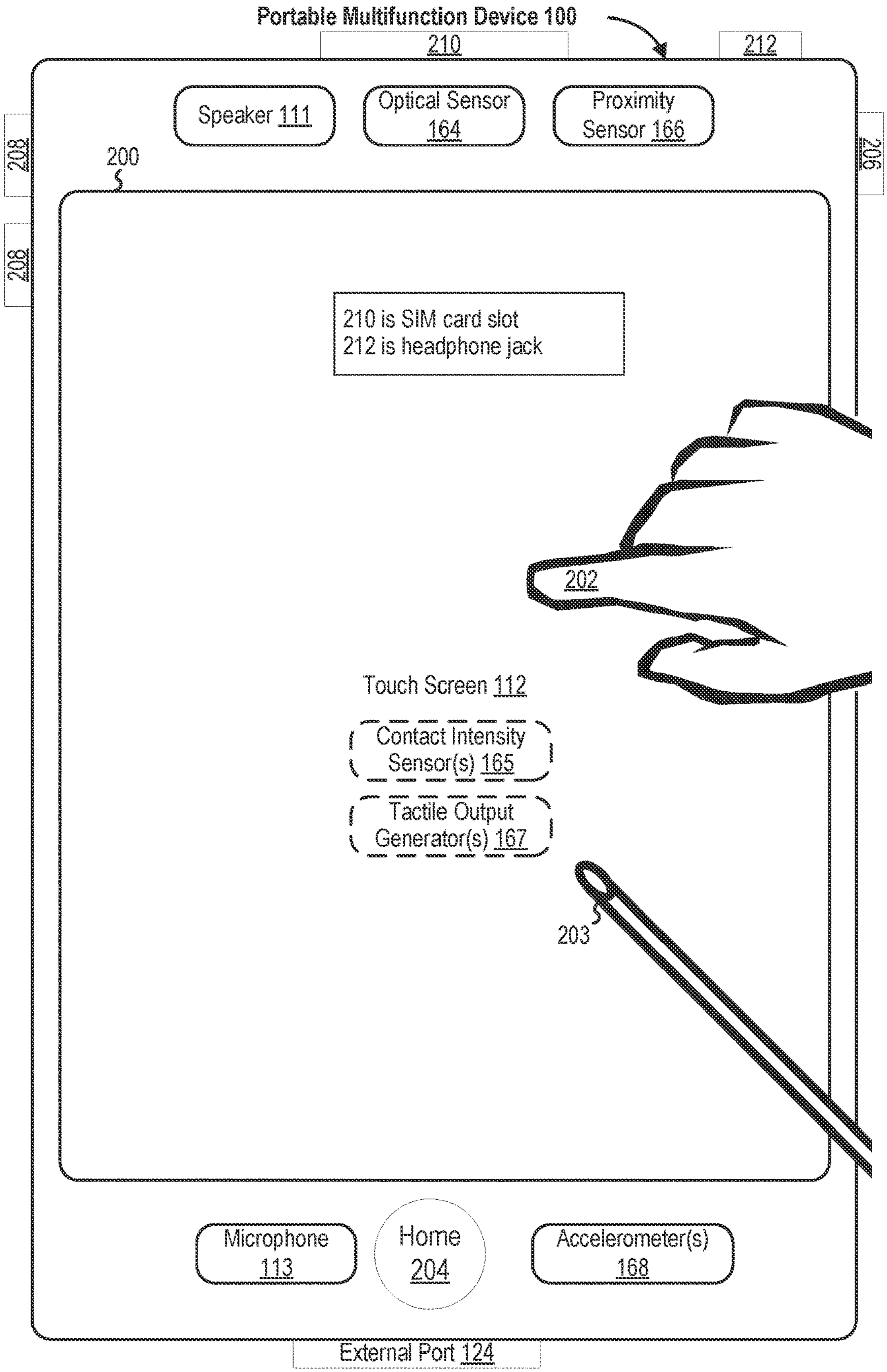
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
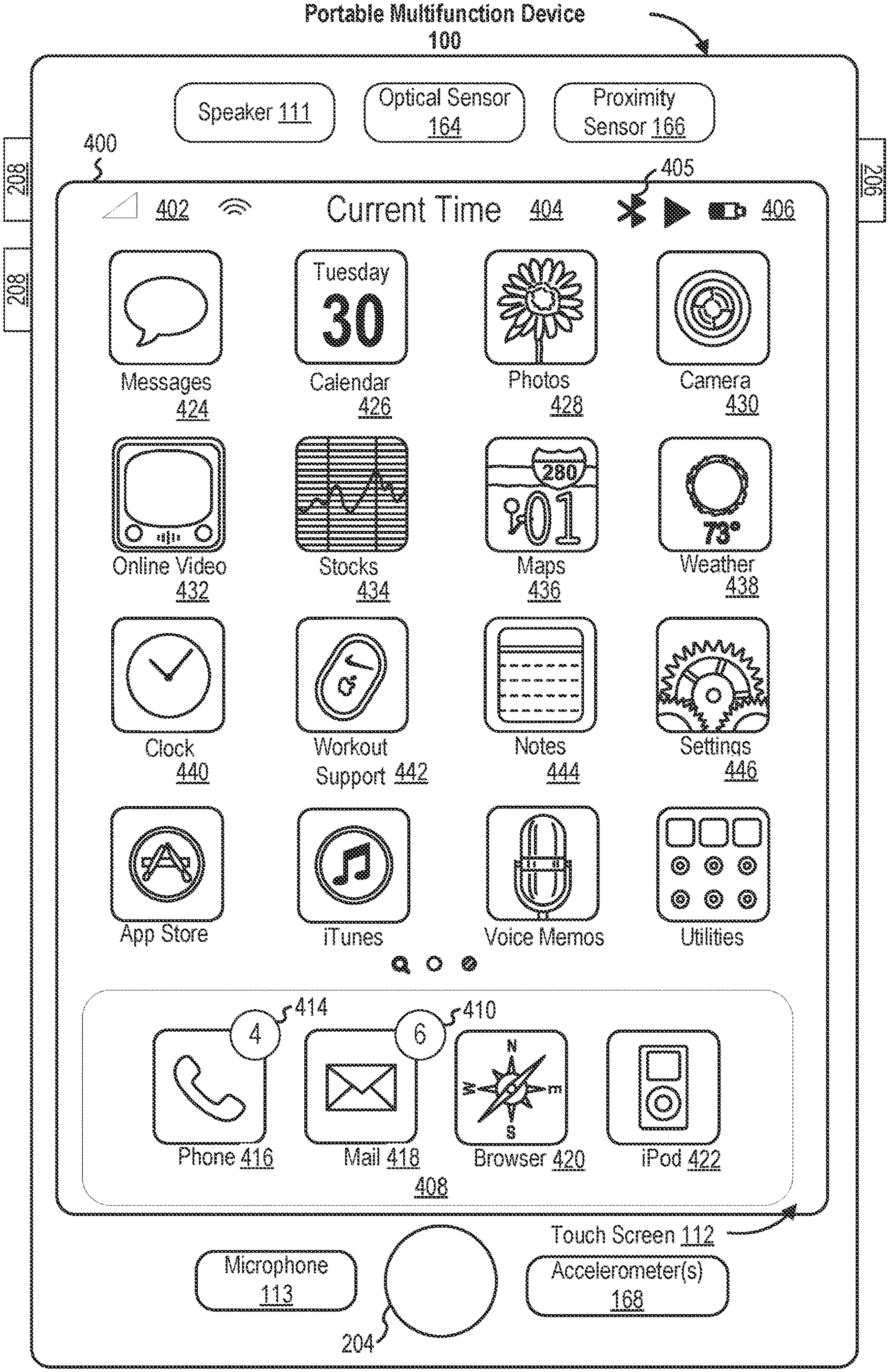
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

- Signal strength indicator(s) 402 for wireless communication(s), such as cellular and Wi-Fi signals;
- Time 404;
- Bluetooth indicator 405;
- Battery status indicator 406;
- Tray 408 with icons for frequently used applications, such as:
  - Icon 416 for telephone module 138, labeled "Phone," which optionally includes an indicator 414 of the number of missed calls or voicemail messages;
  - Icon 418 for e-mail client module 140, labeled "Mail," which optionally includes an indicator 410 of the number of unread e-mails;
  - Icon 420 for browser module 147, labeled "Browser;" and
  - Icon 422 for video and music player module 152, also referred to as iPod (trademark of Apple Inc.) module 152, labeled "iPod;" and
- Icons for other applications, such as:
  - Icon 424 for IM module 141, labeled "Messages;"
  - Icon 426 for calendar module 148, labeled "Calendar;"
  - Icon 428 for image management module 144, labeled "Photos;"
  - Icon 430 for camera module 143, labeled "Camera;"
  - Icon 432 for online video module 155, labeled "Online Video;"
  - Icon 434 for stocks widget 149-2, labeled "Stocks;"
  - Icon 436 for map module 154, labeled "Maps;"
  - Icon 438 for weather widget 149-1, labeled "Weather;"
  - Icon 440 for alarm clock widget 149-4, labeled "Clock;"
  - Icon 442 for workout support module 142, labeled "Workout Support;"
  - Icon 444 for notes module 153, labeled "Notes;" and
  - Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
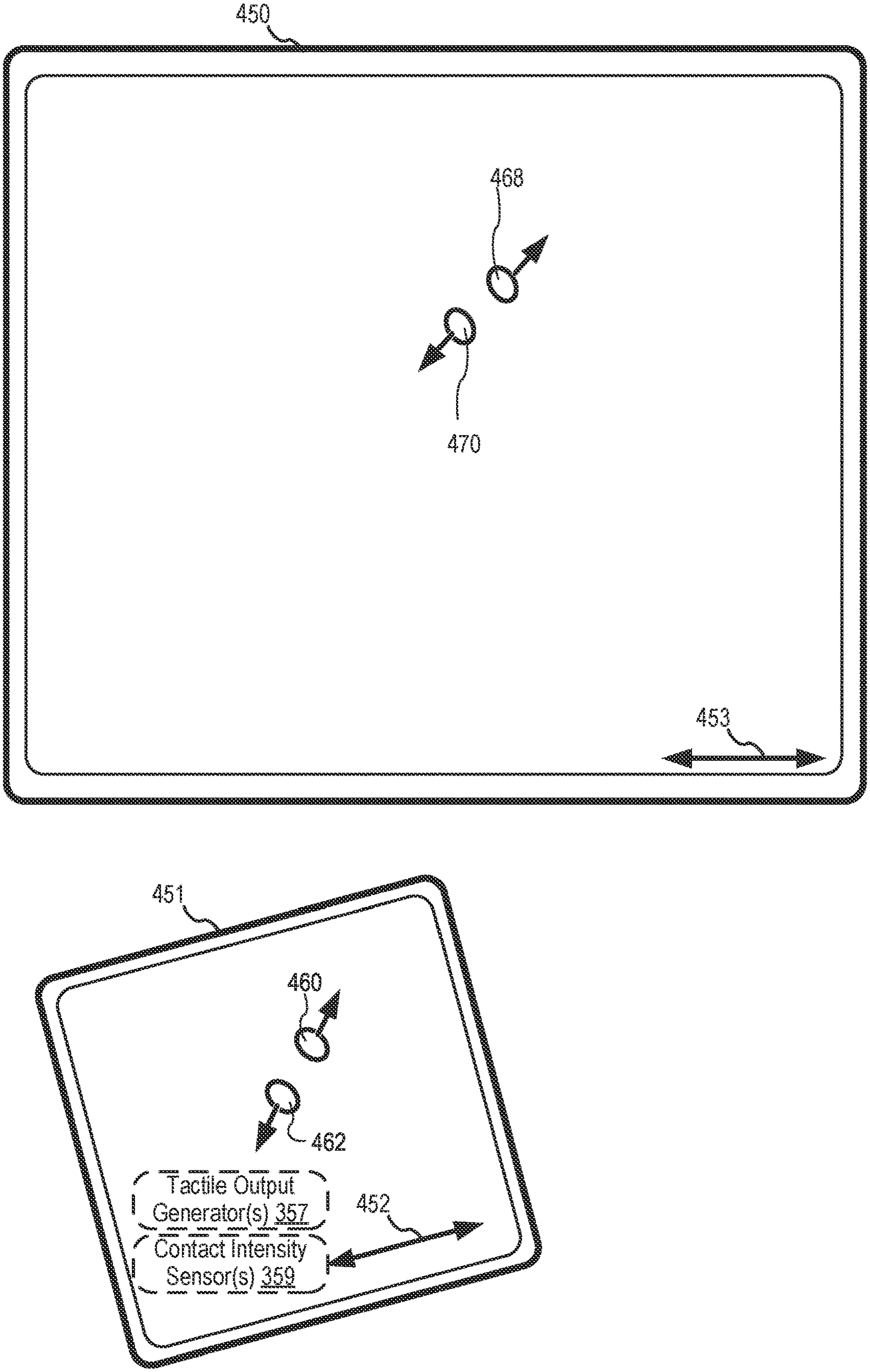
FIG. 4B illustrates an exemplary user interface for a multifunction device with a touch-sensitive surface that is separate from the display in accordance with some embodiments.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
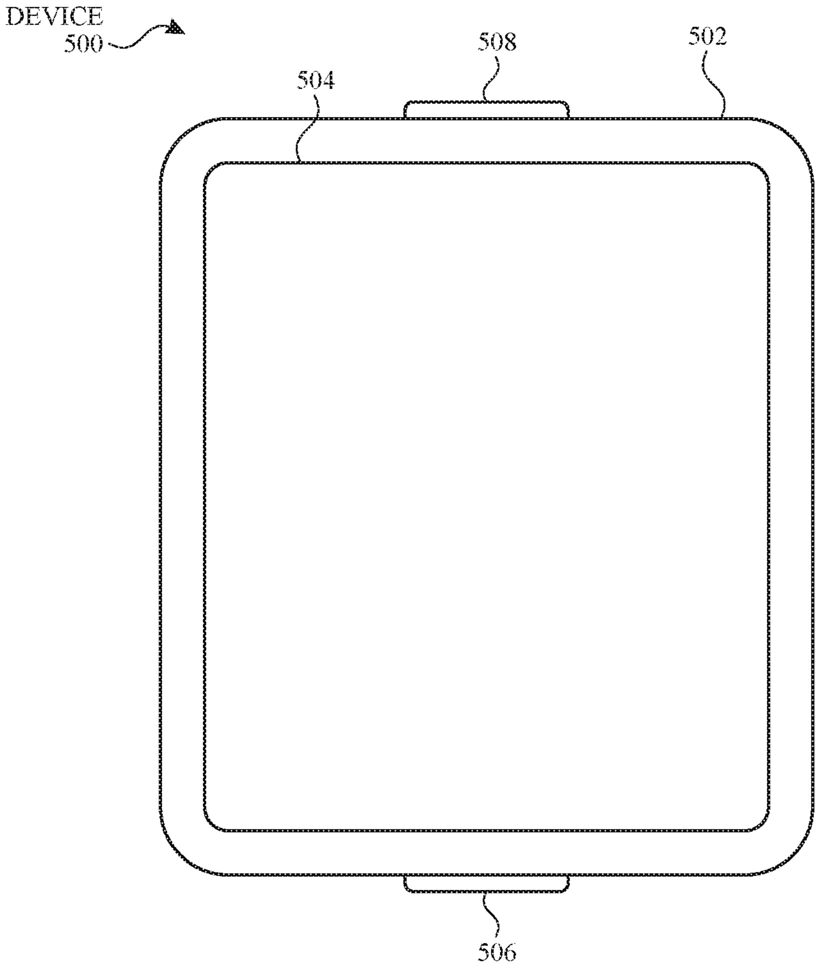
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
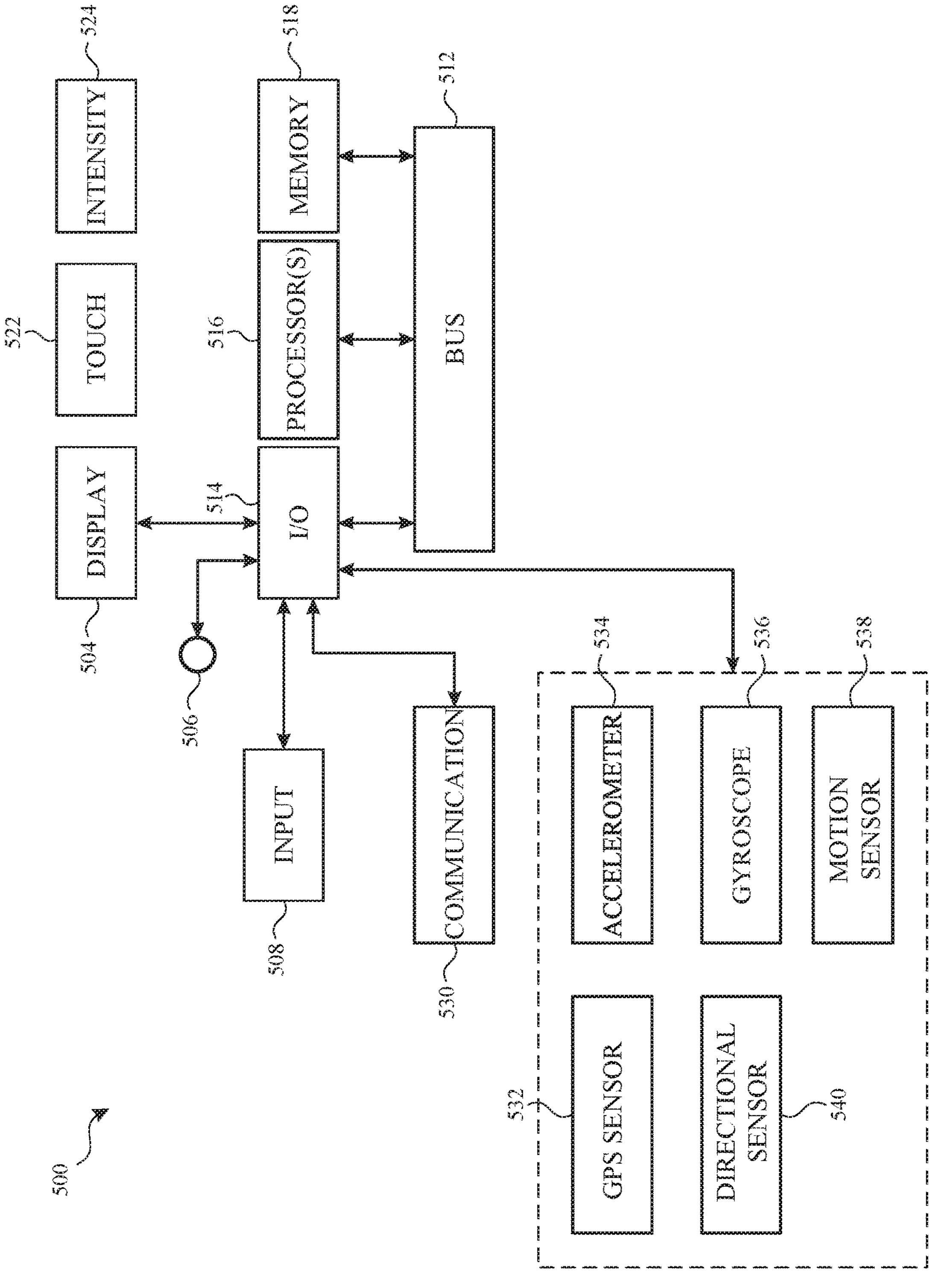
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 and 900 (FIGS. 7 and 9). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Attention is now directed towards embodiments of user interfaces ("UI") and associated processes that are implemented on an electronic device, such as portable multifunction device 100, device 300, or device 500.

FIGS. 6A-6T illustrate exemplary user interfaces for managing shared health-related data, in accordance with some embodiments. The user interfaces in these figures are used to illustrate the processes described below, including the processes in FIG. 7.

FIG. 6A illustrates device 600, which includes touch-screen display 602, displaying a health summary user interface 604 within a health application (e.g., Health App) operating on device 600. Device 600 is a smart phone having one or more features of devices 100, 300, and/or 500 and can be used for tracking health-data related to a primary user account, as well as other user accounts when configured to receive shared health-related user data. In some embodiments, device 600 includes sensors (e.g., accelerometer, gyroscope, GPS) for tracking health-related user data. In some embodiments, device 600 is in communication with one or more smart devices (e.g., a smart watch, a smart scale, a glucose monitor) via a wireless communication protocol (e.g., Bluetooth and/or WiFi), and the smart devices are associated with the primary user account. In some embodiments, the one or more smart devices in communication with device 600 transmit health-related user data to device 600. In some embodiments, device 600 receives one or more user inputs corresponding to manually inputting health-related user data. In some embodiments, health-related user data associated with the primary user account from third-party applications that are operating on device 600 can be imported for display on health summary user interface 604.

In FIG. 6A, health summary user interface 604 includes various selectable affordances 604*a*-604*e* and primary user affordance 606 for a primary user account associated with the user, Tiffany Smith. Primary user affordance 606 indicates that the health data displayed on health summary user interface 604 is associated with the user account of the primary user of device 600 (e.g., Tiffany Smith). Selectable health data affordances 604*a*-604*d* are displayed in the "FAVORITES" section of health summary user interface 604. Activity affordance 604*a* summarizes health data relating to movement, such as calories burned, minutes of exercise, and number of hours that include at least one minute of standing, as performed by the primary user. Heart rate affordance 604*b* includes a heart rate measurement of the primary user. Weight affordance 604*c* includes the most recent weight measurement of the primary user. Steps affordance 604*d* includes a count of how many steps the primary user has taken in a day (e.g., the current day). Highlight affordance 604*e* is displayed in the "HIGHLIGHTS" section of health summary user interface 604 and includes a trend based on the number of steps the primary user has taken in a day over a predetermined period of time (e.g., one day (e.g., today vs. yesterday), one week (e.g., 7 day trend), two weeks (e.g., this week vs. last week), one month), which indicates that the primary user has increased their number of steps in the past week. In some embodiments, highlight affordance 604*e* is based on other types of health data, such as activity, heart rate, blood oxygen levels, weight, workouts, sleep, etc. As previously discussed, in some embodiments, the health data displayed in affordances 604*a*-604*e* can be collected and transmitted to device 600 by an external device (e.g., a smart watch) that is associated with the primary user account and in communication with device 600. In some embodiments, the health data displayed in affordances 604*a*-604*e* can be manually entered using device 600. In some embodiments, the health data displayed in affordances 604*a*-604*e* is imported from third-party applications.

In FIG. 6A, device 600 also displays, on display 602, summary affordance 608, sharing affordance 610, and browse affordance 612. Summary affordance 608 is displayed in an emphasized state (e.g., bolded) to indicate that health summary user interface 604 is being concurrently displayed on device 600. In some embodiments, when sharing affordance 610 is displayed in an emphasized state, a health sharing user interface is displayed. In some embodiments, when browse affordance 612 is displayed in an emphasized state, a health topics user interface is displayed and health data relating to various different health data types associated with the primary user account can be viewed. In FIG. 6A, device 600 detects, via touchscreen display 602, tap input 650*a* corresponding to selection of sharing affordance 610.

Figure 6B:
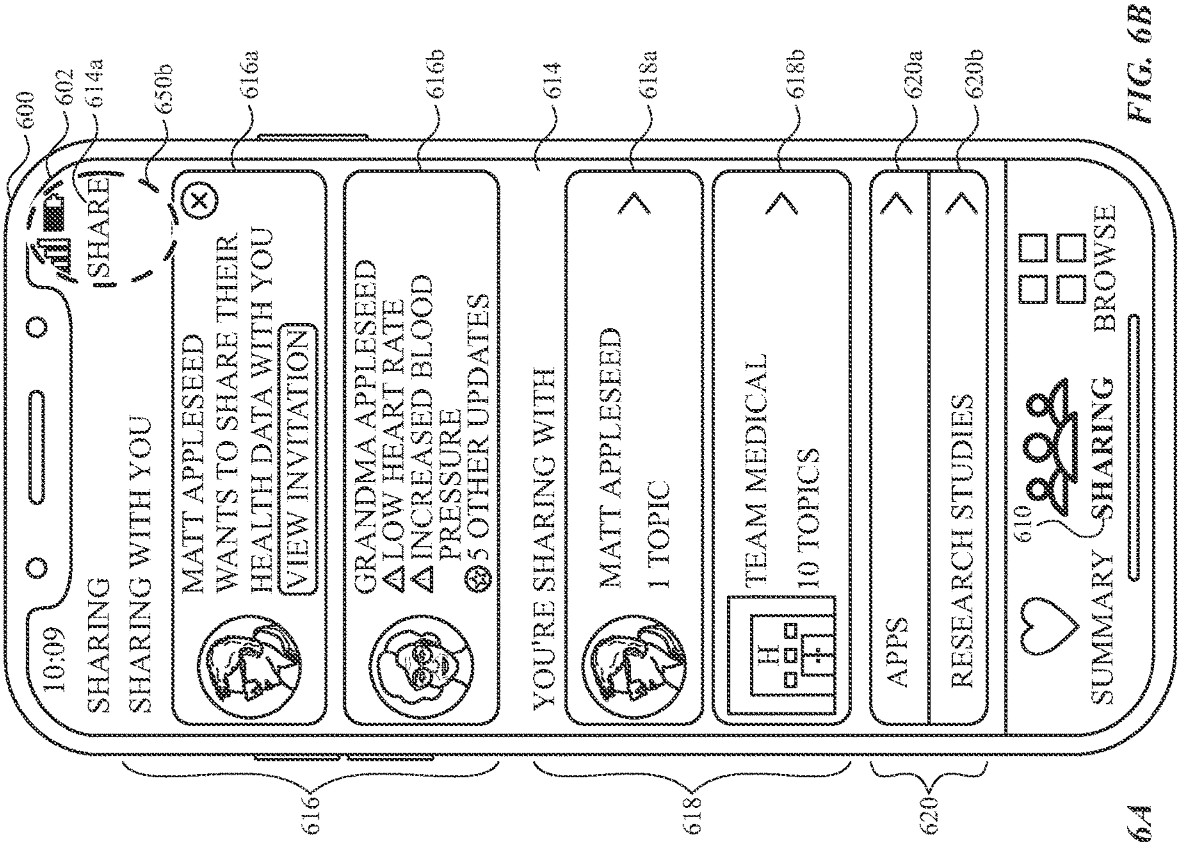
FIGS. 6A-6T illustrate exemplary user interfaces related to sharing health-related data using a computer system, in accordance with some embodiments.

In FIG. 6B, in response to receiving tap input 650*a* at sharing affordance 610, device 600 displays health sharing user interface 614, and sharing affordance 610 is displayed in an emphasized state. Health sharing user interface 614 includes "Sharing with You" section 616 having first sharing affordance 616*a* and second sharing affordance 616*b*. "Sharing with You" section 616 details other user accounts that are sharing their health-related data with the user account of device 600. First sharing affordance 616*a* is shown as an invitation from Matt Appleseed to receive their shared health-related data. Creating an invitation to receive shared health-related data, similar to first sharing affordance 616*a*, is described in more detail below. Second sharing affordance 616*b* corresponds to Grandma Appleseed's shared health-related data. In some embodiments, second sharing affordance 616*b* is shown on health sharing user interface 614 as an invitation for receiving Grandma Appleseed's shared health-related data, similar to first sharing affordance 616*a*. In some embodiments, after accepting the invitation to receive Grandma Appleseed's shared health-related data, second sharing affordance 616*b* is shown with summaries of Grandma Appleseed's shared health-related data, which is discussed in greater detail with respect to FIGS. 8A-8P.

Health sharing user interface 614 of FIG. 6B also includes "You're Sharing with" section 618, which details other user accounts and/or medical institutions (e.g., a healthcare provider) that are receiving shared health-related data from the primary user account associated with device 600. In this example, "You're Sharing with" section 618 includes third sharing affordance 618*a*, which indicates that Matt Appleseed is receiving one topic of shared health-related data associated with the primary user account of device 600, and fourth sharing affordance 618*b*, which indicates that Team Medical is receiving ten topics of shared health-related data associated with the primary user account of device 600. In some embodiments, after sending an invitation to share health-related data associated with the primary user account with another user account (e.g., Matt Appleseed's account) and prior to the other user (e.g., Matt Appleseed) accepting the invitation, third sharing affordance 618*a* is displayed in an invitation pending state, similar to fifth sharing affordance 618*c* of FIG. 6R.

Health sharing user interface 614 of FIG. 6B further includes sharing section 620 having apps affordance 620*a* and research studies affordance 620*b*. In some embodiments, device 600 detects an input corresponding to selection of apps affordance 620*a* and in response, displays a user interface containing applications (e.g., applications installed on device 600) that are receiving health-related data associated with the primary user account of device 600. In some embodiments, device 600 detects an input corresponding to selection of research studies affordance 620*b* and in response, displays a user interface containing research studies that are receiving health-related data associated with the primary user account of device 600. In some embodiments, the primary user associated with device 600 previously enrolled in research studies and selected health-related data for sharing with the research studies.

In FIG. 6B, device 600 receives tap input 650*b* corresponding to selection of share affordance 614*a* displayed on health sharing user interface 614. In FIG. 6C, in response to detecting tap input 650*b* at share affordance 614*a*, device 600 displays a menu containing "With a Person" affordance 614*aa* and "With a Doctor" affordance 614*ab*. Device 600 receives tap input 650*c* corresponding to selection of "With a Person" affordance 614*aa* to initiate creation of an invitation to receive shared health-related data associated with the primary user account of device 600. In some embodiments, selection of "With a Doctor" affordance 614*a* b initiates a process for selecting health-related data associated with the primary user account for sharing with a medical professional and/or healthcare provider.

Figure 6D:
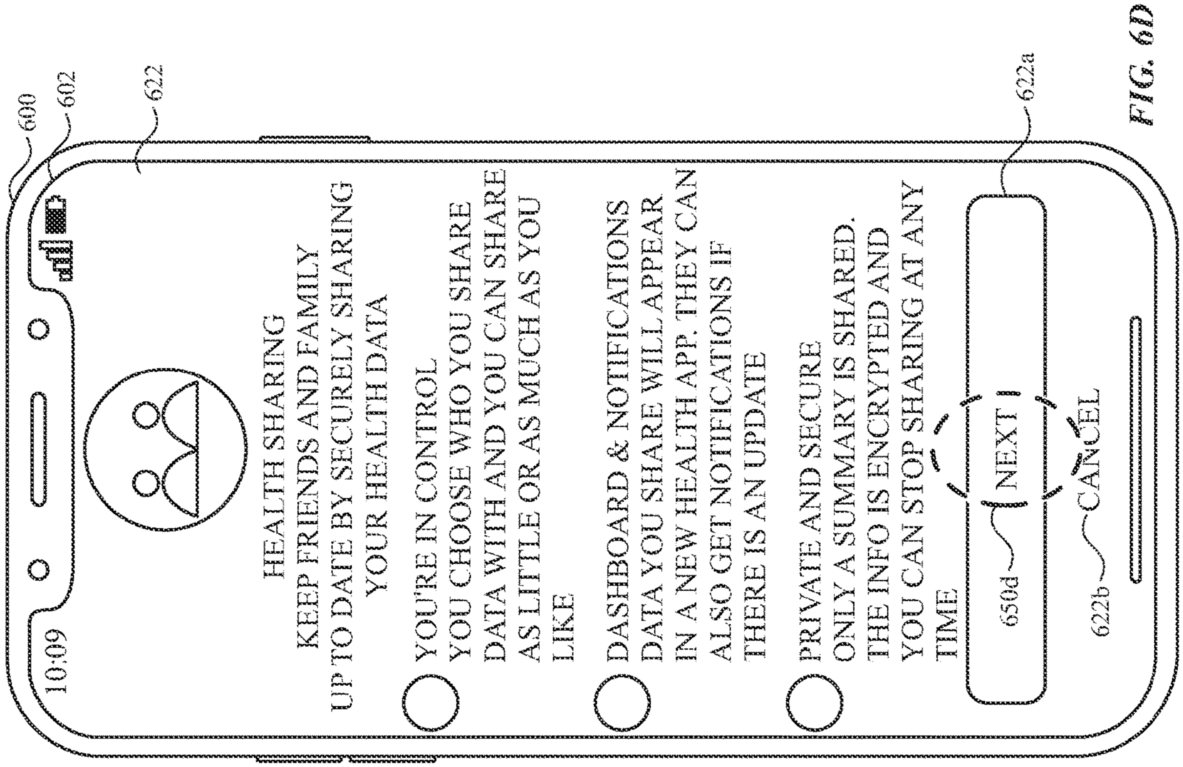
Figure 6C:
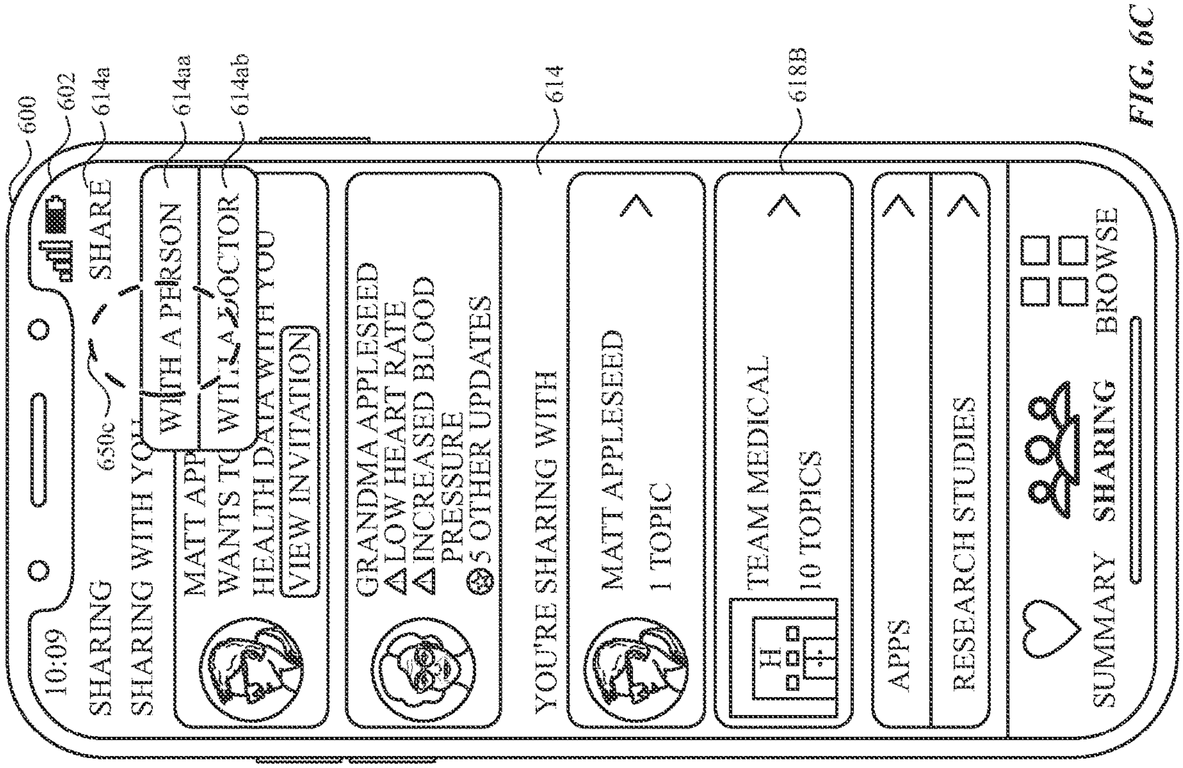
Figure 6F:
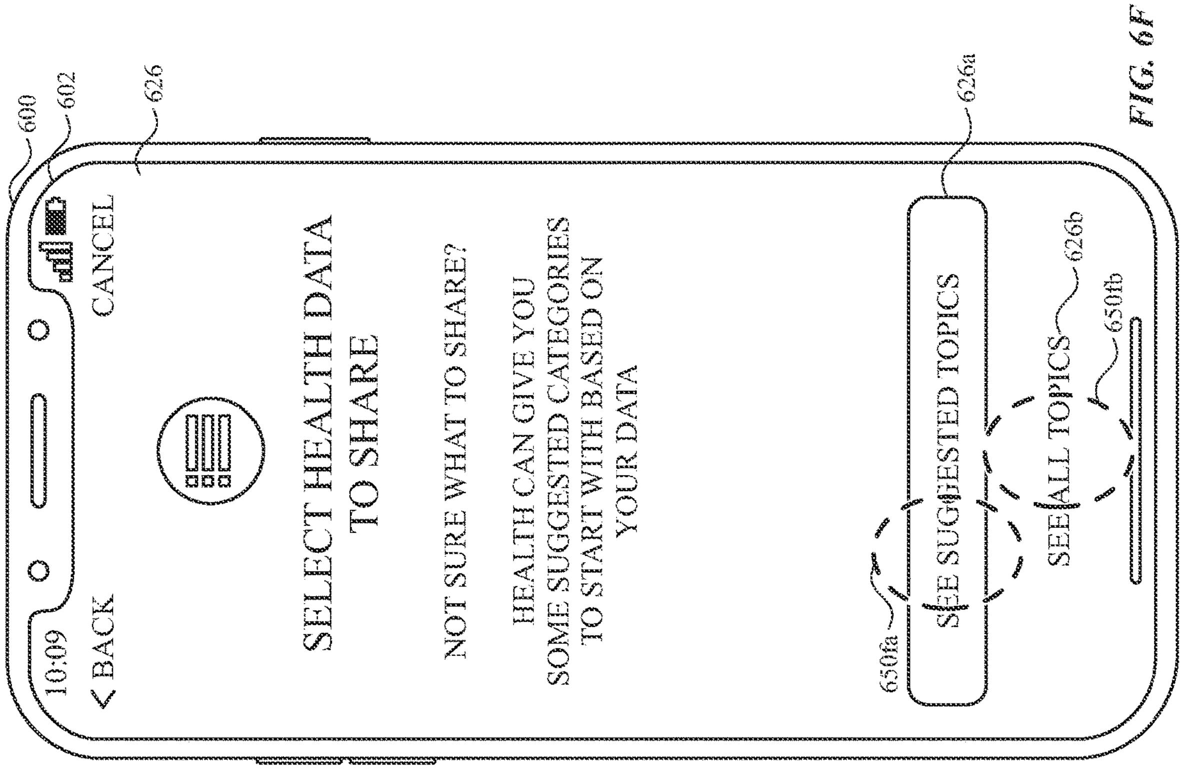

In FIG. 6D, in response to receiving tap input 650*c*, device 600 initiates a process for sharing health-related data associated with the primary user account and displays informational user interface 622. Informational user interface 622 includes an overview for sharing health-related data with other user accounts. Informational user interface 622 includes next affordance 622*a* and cancel affordance 622*b*. In some embodiments, selection of cancel affordance 622*b* cancels the process for sharing health-related data. Device 600 receives tap input 650*d* corresponding to selection of next affordance 622*a* and in response, displays contact selection user interface 624, as shown in FIG. 6E.

Figure 6E:
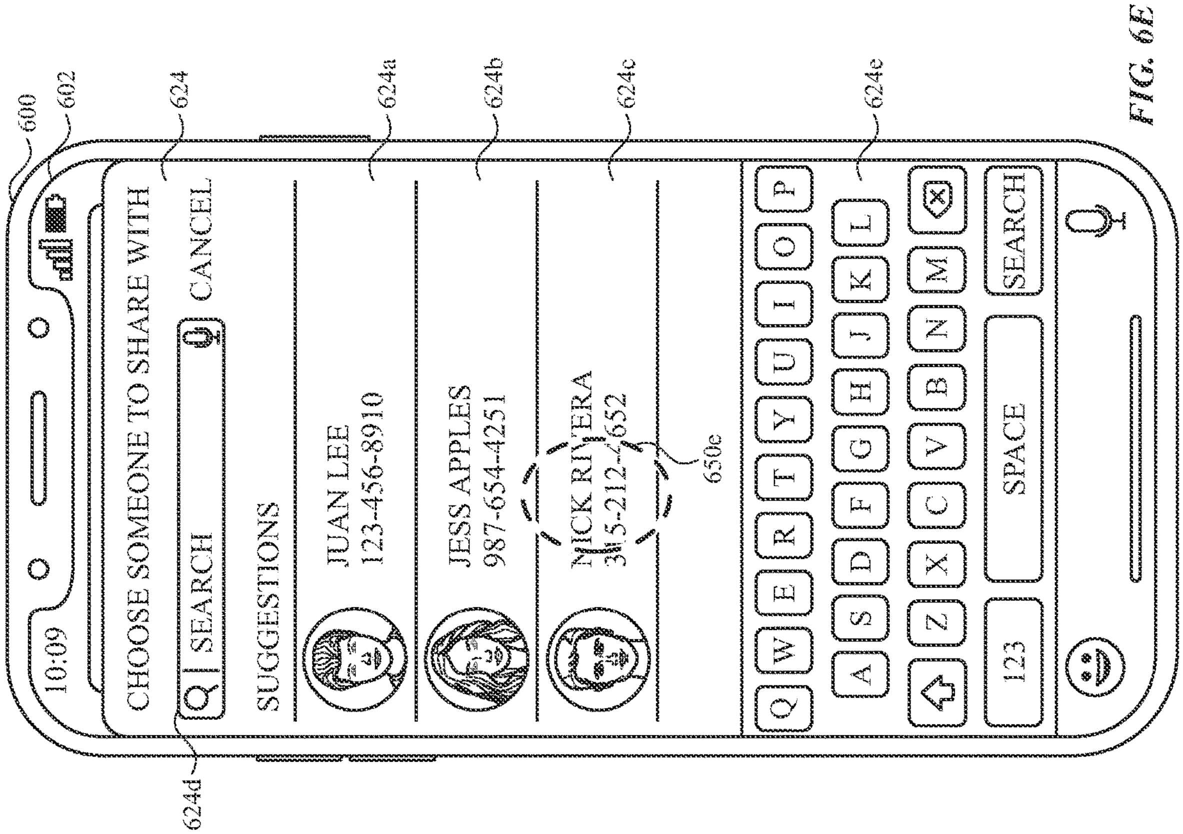
Figure 6H:
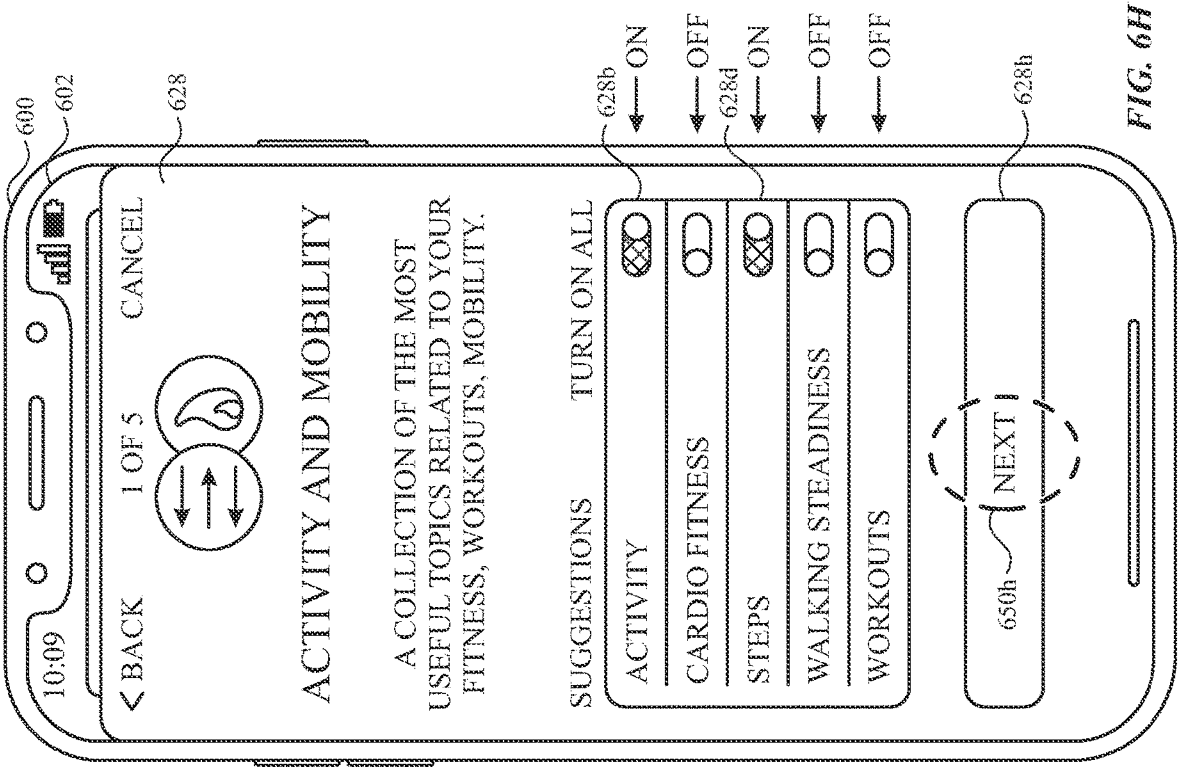

In FIG. 6E, device 600 displays, on touchscreen display 602, contact selection user interface 624. Contact selection user interface 624 contains suggested contacts 624*a*-624*c*. In some embodiments, suggested contacts are user accounts of family members associated with the primary user account via family account sharing, user accounts of people who frequently interact with the primary user account, or a combination thereof. In some embodiments, user accounts that are designated as colleagues are excluded from the suggested contacts. Contact selection user interface 624 also includes search bar 624*d*, in which device 600 can receive inputs at keyboard 624*e* to search for and display a particular contact. In FIG. 6E, device 600 detects tap input 650*e* corresponding to selection of suggested contact 624*c* (Nick Rivera) and in response, designates the user account of Nick Rivera to receive shared health-related data. In some embodiments, device 600 can receive additional inputs to designate more than one contact (e.g., user account) to receive shared health-related data. In some embodiments, additional instances of the process for creating an invitation to receive shared health-related data associated with the primary user account of device 600 must be completed to share health-related data with more than one contact.

Figure 6G:
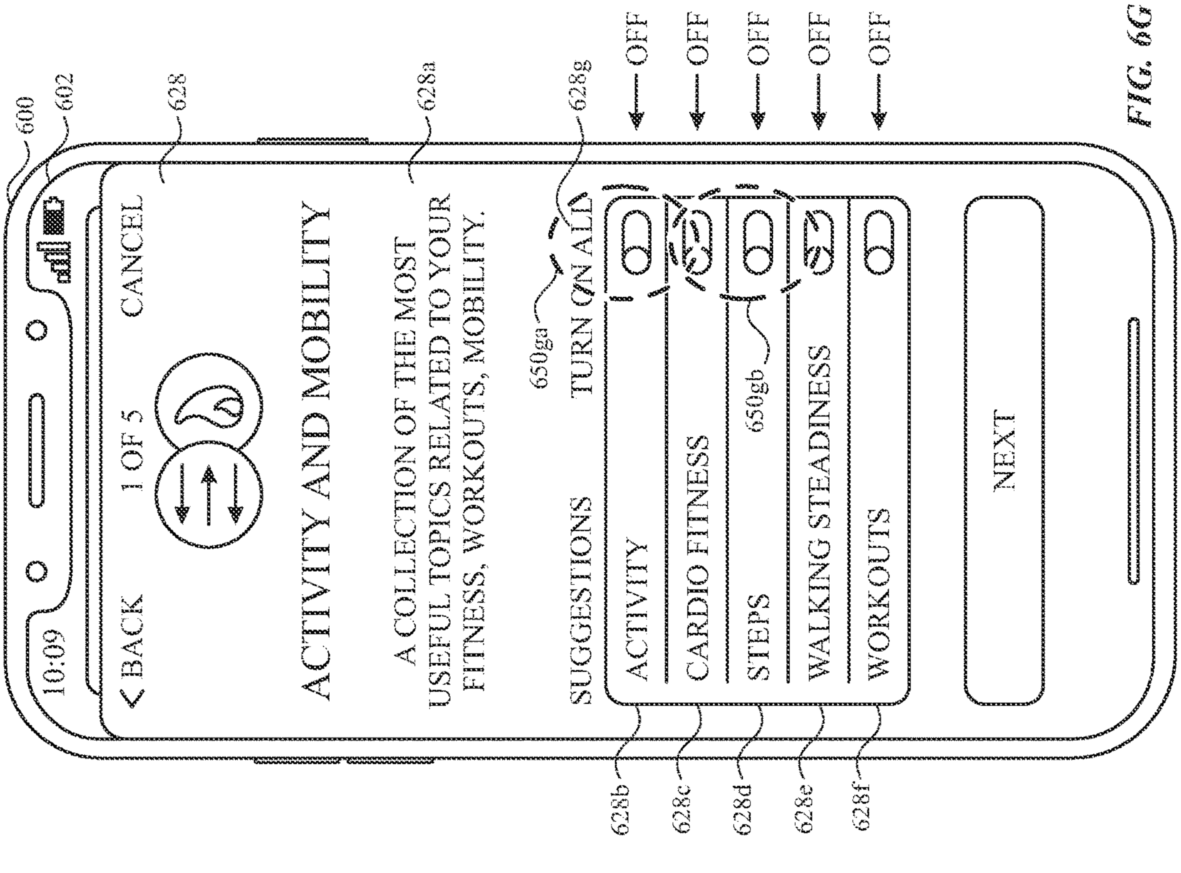

In FIG. 6F, after selection of suggested contact 624*c* for Nick Rivera, device 600 displays sharing introduction user interface 626. Sharing introduction user interface 626 includes a prompt for selecting the types of data for inclusion in a set of health-related data to be shared with the designated contact, Nick Rivera, selectable affordance "back" to return to the previous user interface, and selectable "cancel" affordance to cancel the process for sharing health-related data. Sharing introduction user interface 626 further includes suggested topics affordance 626*a* and see all affordance 626*b*. Device 600 receives tap input 650*fa* corresponding to selection of suggested topics affordance 626*a* and in response, displays data type selection user interface 628, as shown in FIG. 6G. Device 600 receives tap input 650*fb* corresponding to selection of see all affordance 626*b* and in response, displays all topics user interface 648, which is discussed further with respect to FIG. 6T.

In FIG. 6G, in response to detecting tap input 650*fa* selecting suggested topics affordance 626*a*, device 600 displays data type selection user interface 628. Data type selection user interface 628 includes informational section 628*a* and suggestion region containing data type affordances 628*b*-628*f*. Informational section 628*a* provides details about the category, Activity and Mobility, of the suggested data types (e.g., data types recommended by device 600 for sharing). Data type affordances 628*b*-628*f* each represent a health-related measurement pertaining to Activity and Mobility. In some embodiments, device 600 suggests data types for sharing based on the existence of user data (e.g., a data type that does not have any user data is not displayed as a suggestion). In some embodiments, device 600 suggests data types for sharing based on the recency of user data (e.g., a data type that contains user data older than a predetermined threshold period of time (e.g., older than six months, older than one year) is not displayed as a suggestion). In some embodiments, device 600 suggests data types for sharing based on frequency of user interaction with a data type (e.g., via review of the data type or via user data entry) (e.g., a data type used more frequently than other data types is displayed as a suggestion). In some embodiments, device 600 suggests data types for sharing based on a user designation that a data type is a "favorite" data type (e.g., data that has been specifically designated via user input (e.g., "pinned" data) and is therefore, in some embodiments, displayed in the "FAVORITES" section of health summary user interface 604 in FIG. 6A). In some embodiments, data type selection user interface 628 includes a "see more" affordance that, when selected, causes device 600 to display a listing of health-related data types relating to Activity and Mobility to be selected for inclusion in the set of shared health-related data. In some embodiments, in response to selection of the "see more" affordance, device 600 displays a listing of all health-related data types, including the data types relating to Activity and Mobility, to be selected for inclusion in the set of shared health-related data. In some embodiments, device 600 forgoes display of data type selection user interface 628 if user data related to Activity and Mobility is unavailable (e.g., the user data does not meet the at least one suggestion criteria previously described).

In FIG. 6G, data type affordances 628*b*-628*f* each contain a toggle in the "OFF" position, indicating that each data type is not currently included in the set of health-related data (e.g., health topics) for sharing with the designated contact. Device 600 detects tap input 650*ga* corresponding to selection of the toggle within data type affordance 628*b* for Activity and tap input 650*gb* corresponding to selection of the toggle within data type affordance 628*d* for Steps. In response to receiving tap inputs 650*ga* and 650*gb*, device 600 modifies the toggles in data type affordance 628*b* for Activity Ring and data type affordance 628*d* for Steps to be in the "ON" position, as shown in FIG. 6H. In some embodiments, device 600 detects a tap input at "TURN ON ALL" affordance 628*g* and in response, modifies the toggles to be in the "ON" position for all data type affordances 628*b*-628*f*.

In FIG. 6H, device 600 displays data type selection user interface 628 on touchscreen display 602. Data type selection user interface 628 includes data type affordance 628*b* for Activity and data type affordance 628*d* for Steps with toggles in the "ON" position, indicating that each of these data types are included in the set of health-related data for sharing. Device 600 detects tap input 650*h* corresponding to selection of next affordance 628*h*. In response to receiving tap input 650*h*, device 600 displays data type selection user interface 630, as shown in FIG. 6I.

Figure 6I:
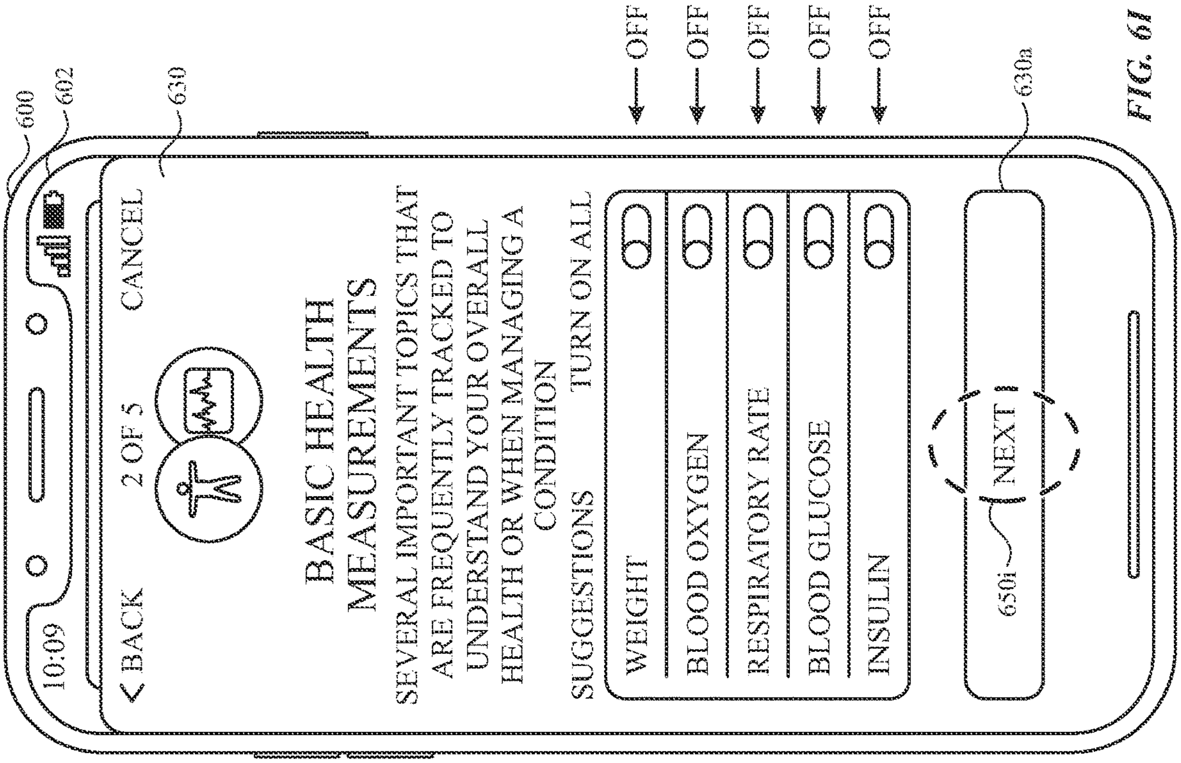

In FIG. 6I, device 600 displays, on touch screen display 602, data type selection user interface 630 for suggestion of data types relating to the category of Basic Health Measurements. Data type selection user interface 630 is analogous to data type selection user interface 628 in that it contains a set of data type affordances relating to the overarching category (e.g., Basic Health Measurements for data type selection user interface 630 and Activity and Mobility for data type selection user interface 628) that can be selected for inclusion in the set of health-related data for sharing. The data type affordances included in data type selection user interface 630 are suggested based on criteria analogous to those described with respect to data type selection user interface 628 in FIG. 6G. The toggles contained within the data type affordances of data type selection user interface 630 are shown in the "OFF" position, indicating that the data types are not included in the set of health-related data for sharing. In some embodiments, device 600 forgoes display of data type selection user interface 630 if user data related to Basic Health Measurements is unavailable (e.g., the user data does not meet the at least one suggestion criteria previously described with respect to FIG. 6G).

Figure 6J:
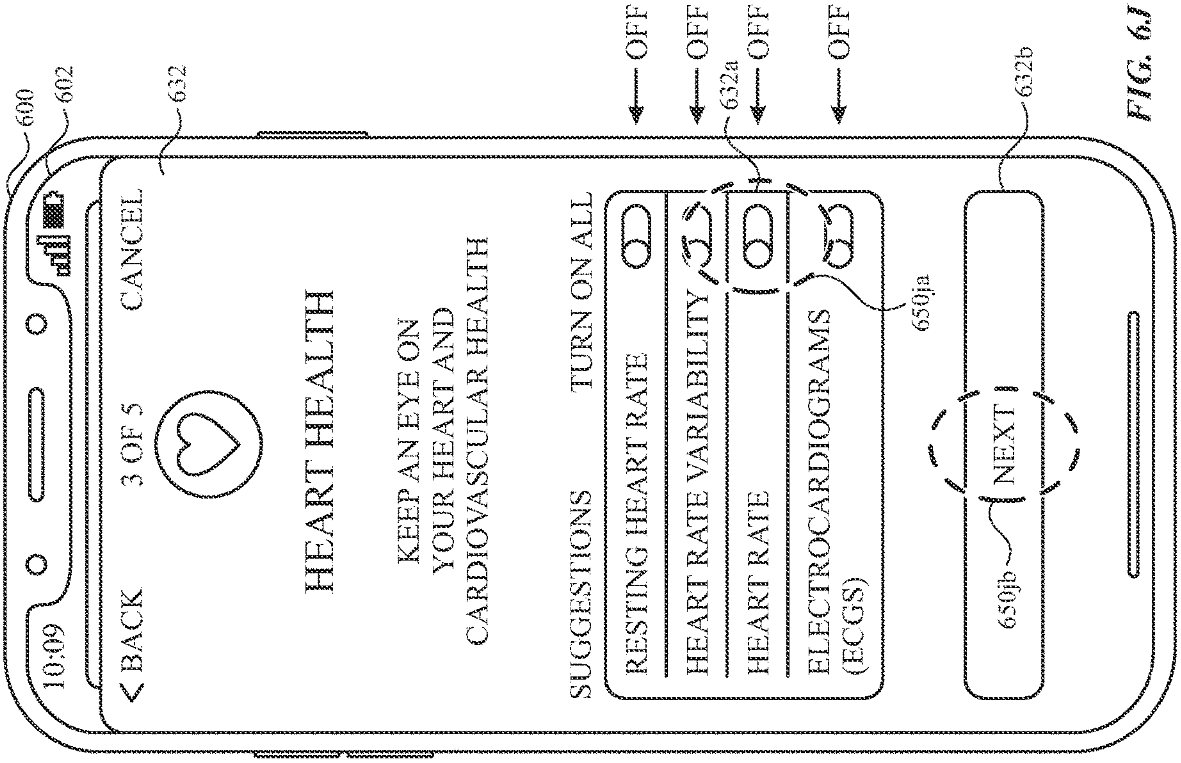
Figure 6L:
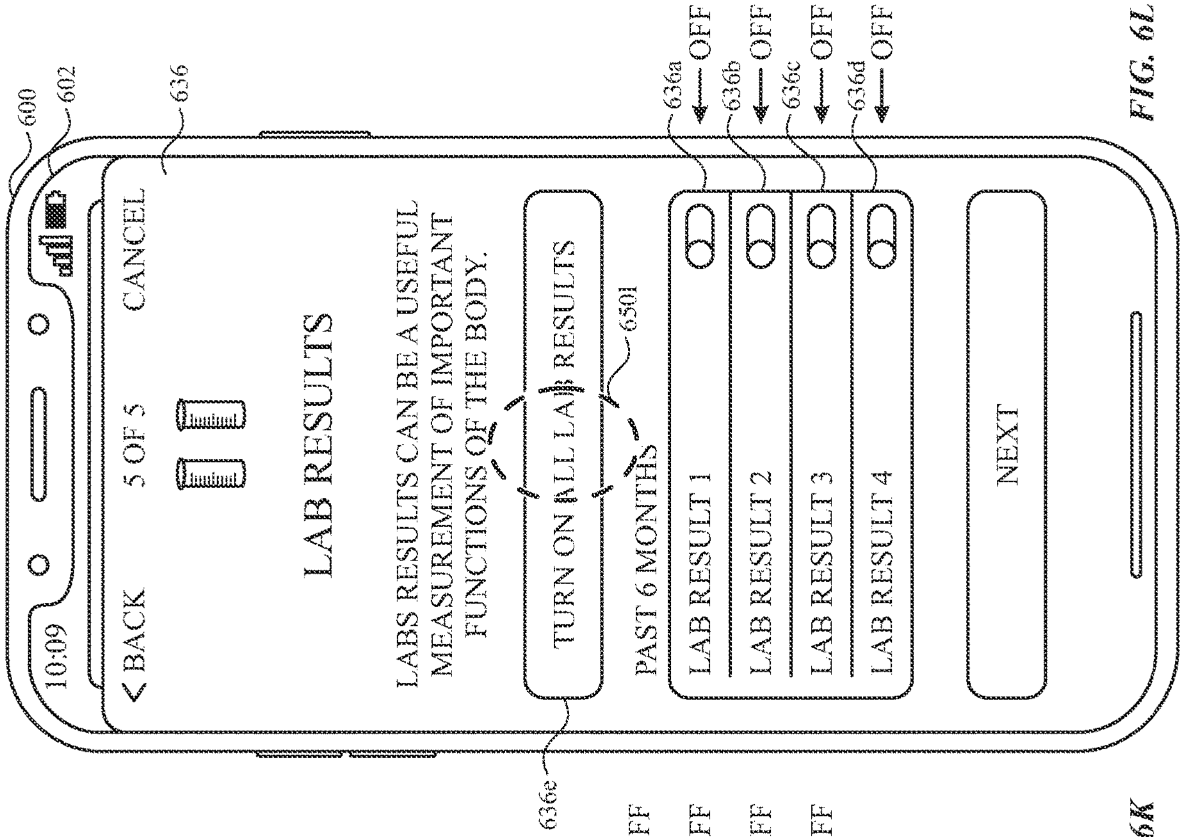

In FIG. 6I, device 600 receives tap input 650*i* corresponding to selection of next affordance 630*a*. In FIG. 6J, in response to detecting tap input 650*i*, device 600 displays, on touch screen display 602, data type selection user interface 632 for suggestion of data types relating to the category of Heart Health. Data type selection user interface 632 is analogous to data type selection user interface 628 in that it contains a set of data type affordances relating to the overarching category (e.g., Heart Health for data type selection user interface 632 and Activity and Mobility for data type selection user interface 628) that can be selected for inclusion in the set of health-related data for sharing. The data type affordances included in data type selection user interface 632 are suggested based on criteria analogous to those described with respect to data type selection user interface 628 in FIG. 6G. In some embodiments, device 600 forgoes display of data type selection user interface 632 if user data related to Heart Health is unavailable (e.g., the user data does not meet the at least one suggestion criteria previously described with respect to FIG. 6G).

In FIG. 6J, device 600 detects tap input 650*ja* corresponding to selection of the toggle contained within data type affordance 632*a* for Heart Rate to include heart rate measurements in the set of health-related data for sharing. In response to receiving tap input 650*ja*, device 600 updates the toggle within data type affordance 632*a* for Heart Rate from the "OFF" position to the "ON" position, similar to the toggle within data type affordance 628*d* in FIG. 6H. Device 600 further detects tap input 650*j* b, after detecting tap input 650*ja*, corresponding to selection of next affordance 632*b* and in response, device 600 displays data type selection user interface 634, as shown in FIG. 6K.

Figure 6K:
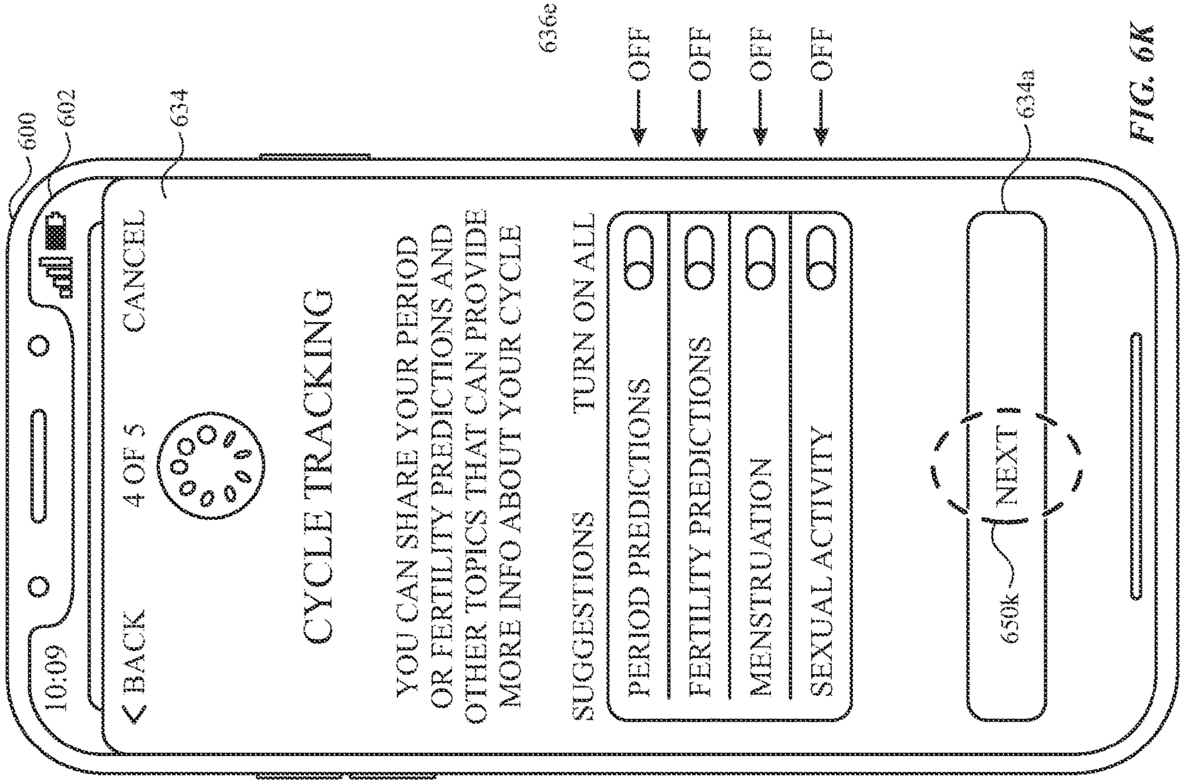

In FIG. 6K, device 600 displays, on touch screen display 602, data type selection user interface 634 for suggestion of data types relating to the category of Cycle Tracking (e.g., menstruation cycle). Data type selection user interface 634 is analogous to data type selection user interface 628 in that it contains a set of data type affordances relating to the overarching category (e.g., Cycle Tracking for data type selection user interface 632 and Activity and Mobility for data type selection user interface 628) that can be selected for inclusion in the set of health-related data for sharing. The data type affordances included in data type selection user interface 634 are suggested based on criteria analogous to those described with respect to data type selection user interface 628 in FIG. 6G. In some embodiments, device 600 forgoes display of data type selection user interface 634 if user data related to Cycle Tracking is unavailable (e.g., the user data does not meet the at least one suggestion criteria previously described with respect to FIG. 6G).

In FIG. 6K, device 600 receives tap input 650*k* corresponding to selection of next affordance 634*a*. In FIG. 6L, in response to detecting tap input 650*k*, device 600 displays, on touch screen display 602, lab results user interface 636. Lab results user interface 636 includes a lab results section containing lab result affordances 636*a*-363*d*. Lab result affordances 636*a*-636*d* correspond to specific instances in which a laboratory test (e.g., a blood test, an allergy test) was conducted and the results were received by device 600 (e.g., via data transmission from an external device, via data transmission from an application, or via manual user input). In some embodiments, device 600 displays a lab result affordance if the corresponding lab result meets a recency criteria (e.g., the laboratory test was conducted within the past six months). In some embodiments, device 600 displays a lab result affordance for each historical lab result associated with the primary user account. In some embodiments, device 600 receives an input corresponding to selection of the toggle within lab result affordance 636*a* and in response, updates the toggle from the "OFF" position to the "ON" position. In such embodiments, device 600 shares only the specific lab result corresponding to lab result affordance 636*a* when the toggle is in the "ON" position. In some embodiments, lab result affordances 636*a*-363*d* correspond to various types of laboratory test results. In such embodiments, in response to detecting an input corresponding to selection of a toggle to enable sharing of a type of laboratory test result, device 600 shares one or more lab results corresponding to the selected type of laboratory test result, including historical results of the selected type of laboratory test result, optionally dating back to a predetermined period of time (e.g., COVID-19 test results from the last 6 months; current and previous laboratory results for cholesterol level tests).

In FIG. 6L, while displaying lab results user interface 636, device 600 detects tap input 650*l* corresponding to selection of all affordance 636*e*. In some embodiments, device 600 detects inputs corresponding to selection of one or more lab result affordances 636*a*-363*d* to enable sharing of the one or more selected existing lab results prior to detecting tap input 650*l*. In response to receiving tap input 650*l*, device 600 displays all lab results user interface 638, as shown in FIG. 6M. In some embodiments, tap input 650*l* causes lab result affordances 636*a*-363*d* to be toggled, but does not cause display of all lab results user interface 638, until another input is received on the "next" affordance of lab results user interface 636 is selected.

In FIG. 6M, device 600 displays all lab results user interface 638 for enabling sharing of any future laboratory test results for the primary user account received by device 600. Device 600 receives tap input 650*ma* corresponding to selection of the toggle within automatically share affordance 638*a*. In response to receiving tap input 650*ma*, device 600 updates the toggle from the "OFF" position to the "ON" position and enables sharing of future laboratory test results received for the primary user account. In some embodiments, device 600 does not receive tap input 650*ma* and does not enable sharing of future laboratory test results received for the primary user account. Device 600 further receives tap input 650*m* b, after receiving tap input 650*ma*, corresponding to selection of next affordance 638*b* and in response, displays health alert user interface 640, as shown in FIG. 6N.

Figure 6N:
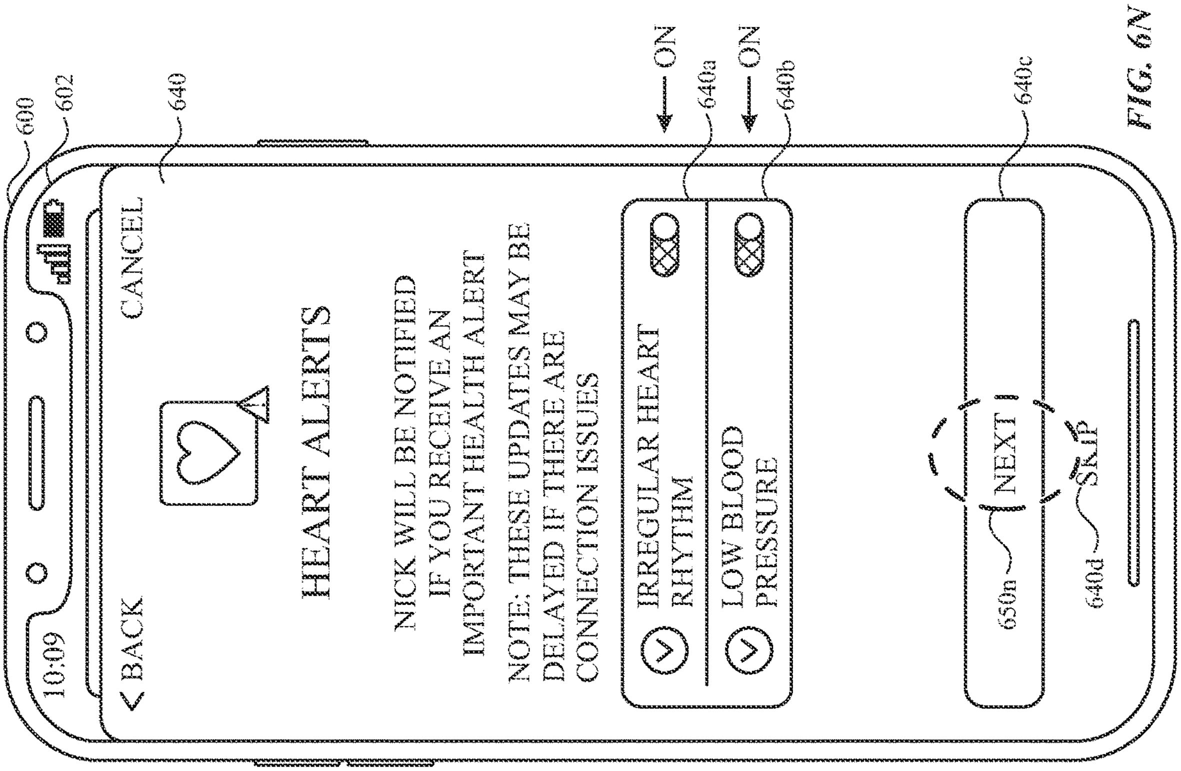
Figure 6M:
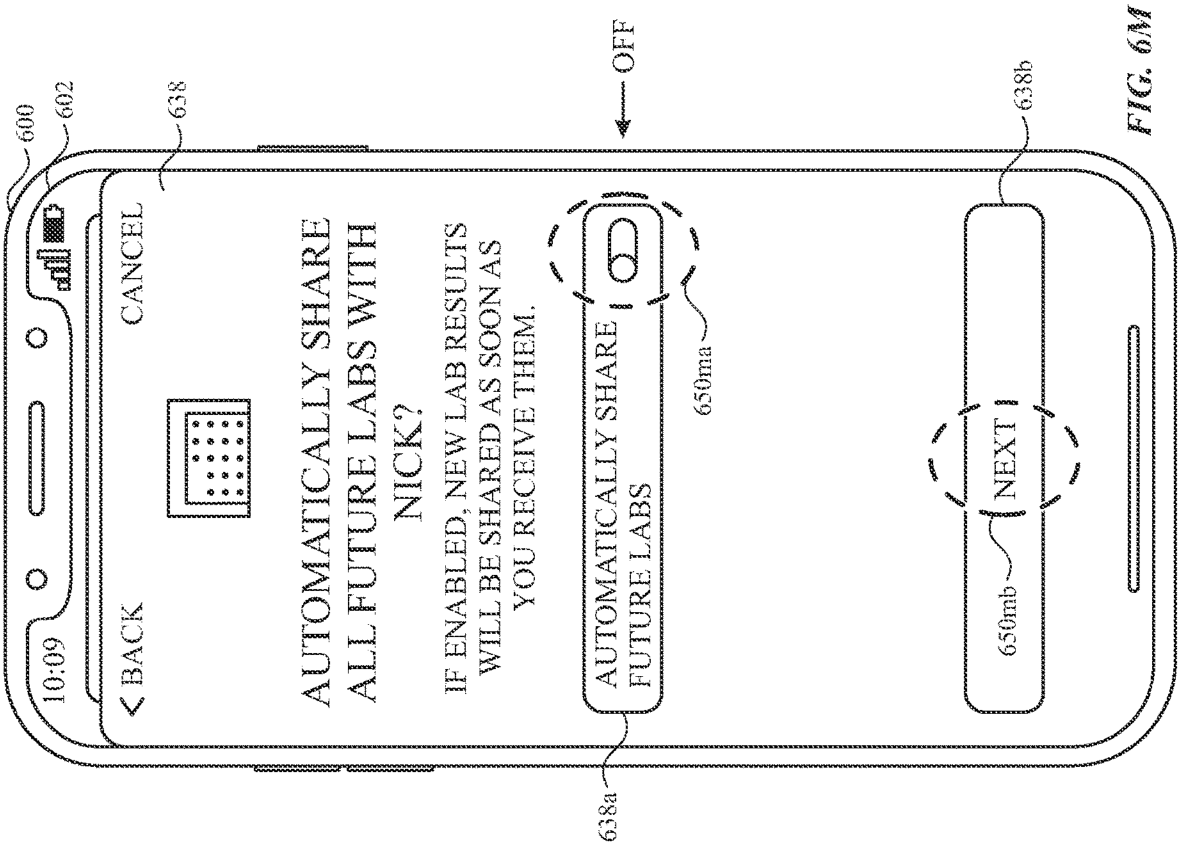
Figure 6P:
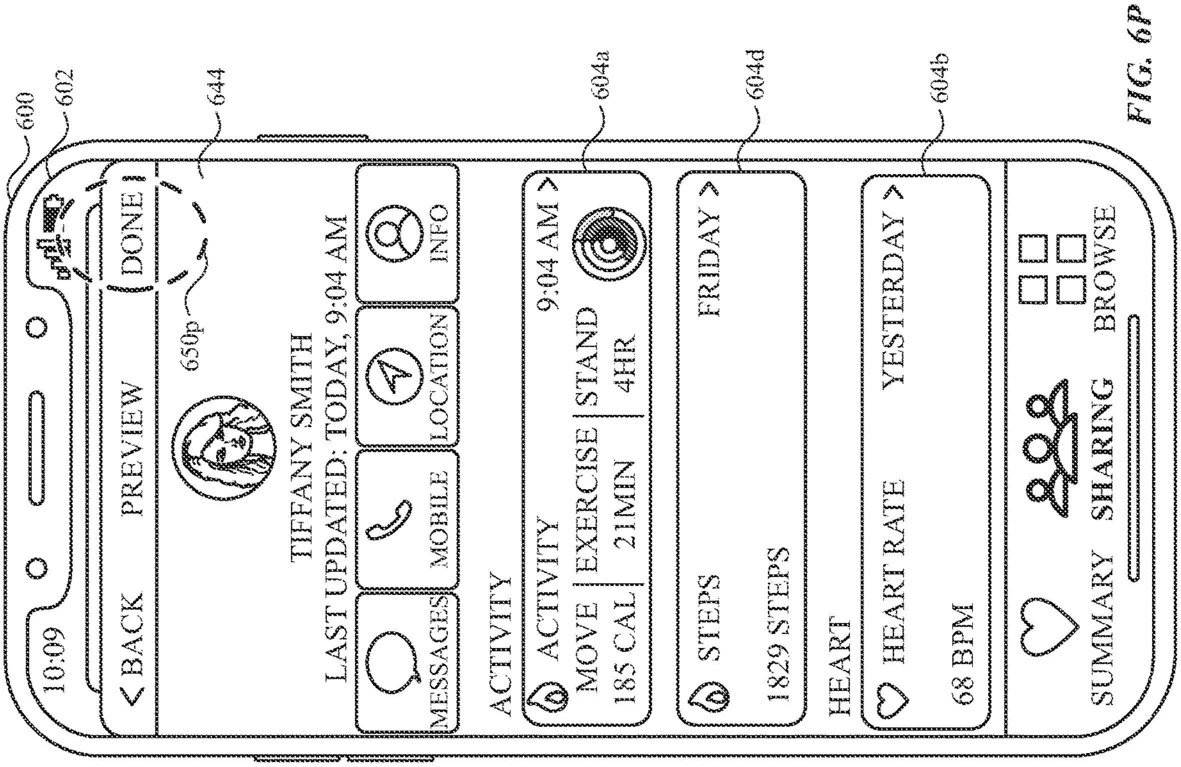

In FIG. 6N, device 600 displays, on touchscreen display 602, health alert user interface 640. Health alert user interface 640 includes an informational section detailing the type of content for sharing, including a warning about delayed delivery of alerts, alert affordance 640*a* for irregular heart rhythm alerts, and alert affordance 640*b* for low blood pressure alerts. In some embodiments, device 600 displays alert affordances corresponding to alert types that are enabled for the primary user account. In this example, device 600 outputs an alert after detecting irregular heart rhythms and/or low blood pressure. Each toggle within alert affordances 640*a*-640*b* are shown in the "ON" position for inclusion in the set of health-related data for sharing. In some embodiments, device 600 displays health alert user interface 640 with each toggle within alert affordances 640*a*-640*b* in the "OFF" position, and device 600 receives one or more inputs corresponding to selection of one or more toggles and in response, updates the selected toggle(s) to the "ON" position. In some embodiments, device 600 detects an input corresponding to selection of skip affordance 640*d* and forgoes inclusion of health alerts in the set of health-related data for sharing. Device 600 detects tap input 650*n* corresponding to selection of next affordance 640*c* and in response, displays summary user interface 642, as shown in FIG. 6O.

Figure 6O:
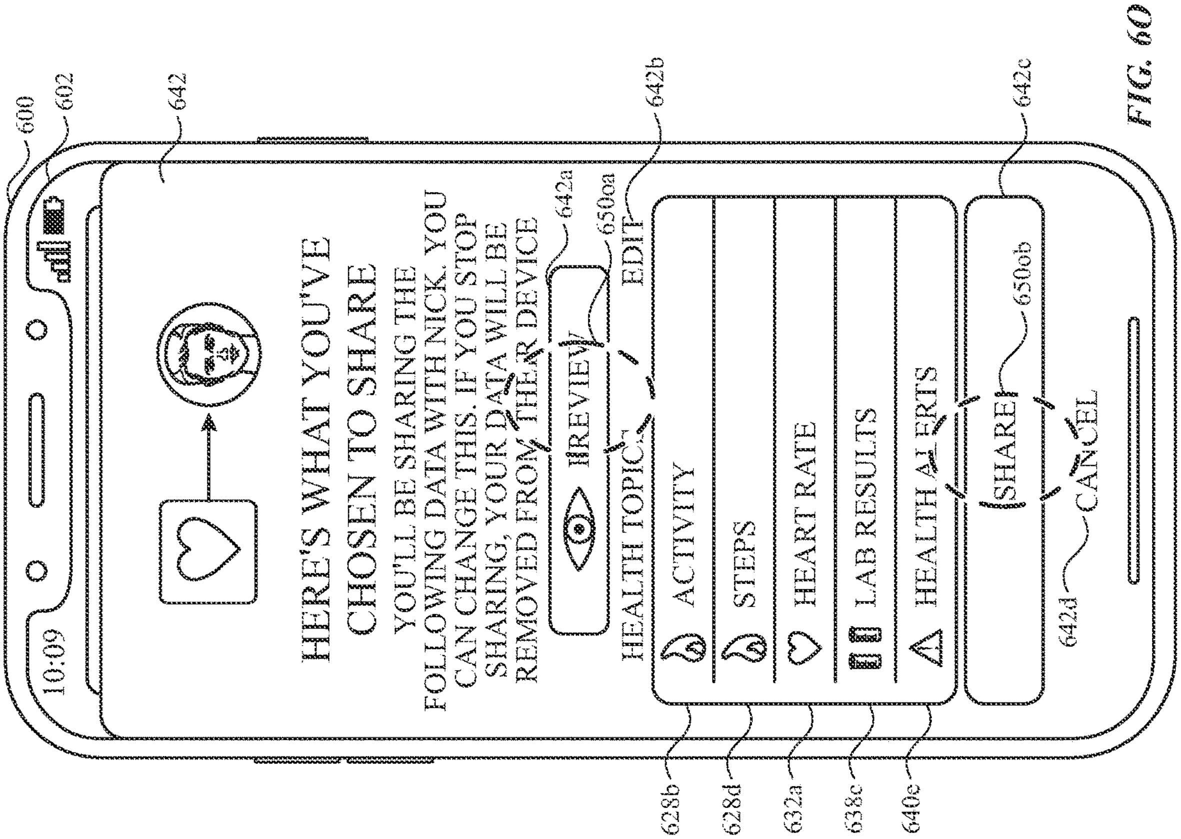

In FIG. 6O, device 600 displays summary user interface 642 that details the set of health topics selected for sharing.

Summary user interface 642 includes: data type affordance 628*b* for Activity, as selected in FIGS. 6G-6H; data type affordance 628*d* for Steps, as selected in FIGS. 6G-6H; data type affordance 632*a* for Heart Rate, as selected in FIG. 6J; lab results affordance 638*c*, corresponding to selection of automatically share affordance 638*a* in FIG. 6M; and alert affordance 640*e*, corresponding to alert affordances 640*a*-640*b* enabled for sharing in FIG. 6N. In some embodiments, if one or more laboratory test result are selected for sharing in FIG. 6L, summary user interface 642 includes one or more lab results affordance, similar to lab results affordance 638*c*, corresponding to each laboratory test result selected for sharing in FIG. 6L. In some embodiments, summary user interface 642 includes two alert affordances, similar to alert affordance 640*e*, corresponding to each alert affordance 640*a* for irregular heart rhythm alerts and alert affordance 640*b* for low blood pressure alerts, as enabled for sharing in FIG. 6N. In some embodiments, device 600 receives an input corresponding to selection of edit affordance 642*b* and in response, displays a user interface for editing (e.g., excluding one or more previously selected topics from the set for sharing; including one or more topics that were not previously selected in the set for sharing) the topics included in the set of health-related data for sharing.

In FIG. 6O, device 600 receives tap input 650*oa* corresponding to selection of preview affordance 642*a* shown on summary user interface 642. Device 600 also receives tap input 650*ob*, at a point in time after receiving input 650*oa*; the response to input 650*ob* is discussed in more detail below. In response to detecting tap input 650*oa*, device 600 displays preview user interface 644, as shown in FIG. 6P.

In FIG. 6P, device 600 displays, on touchscreen display 602, preview user interface 644 that previews the format and layout of health topics for sharing with designated contact Nick Rivera. In some embodiments, preview user interface 644 is an approximation of an interface that would be displayed on a device associated with the user account Nick Rivera, when viewing the shared health data of the Tiffany Smith account, once shared. Preview user interface 644 includes contact region 644*a* having primary user affordance 606 for Tiffany Smith, similar to primary user affordance 606 shown on health summary user interface 604 of FIG. 6A, along with various selectable affordances the designated contact (e.g., Nick Rivera) can use to contact Tiffany Smith. Preview user interface 644 further includes activity affordance 604*a*, steps affordance 604*d*, and heart rate affordance 604*b* containing metrics for the primary user, Tiffany Smith, that are analogous to those shown on health summary user interface 604 and discussed with respect to FIG. 6A. In some embodiments, device 600 receives a swipe input and in response, scrolls preview user interface 644 to show additional health topic affordances corresponding to highlights (e.g., highlight affordance 604*e* of FIG. 6A) and other health topics selected for sharing (e.g., laboratory test results and health alerts). Device 600 receives tap input 650*p* corresponding to selection of done affordance 644*b* and in response, ceases displaying preview user interface 644 and re-displays summary user interface 642 of FIG. 6O.

Figure 6Q:
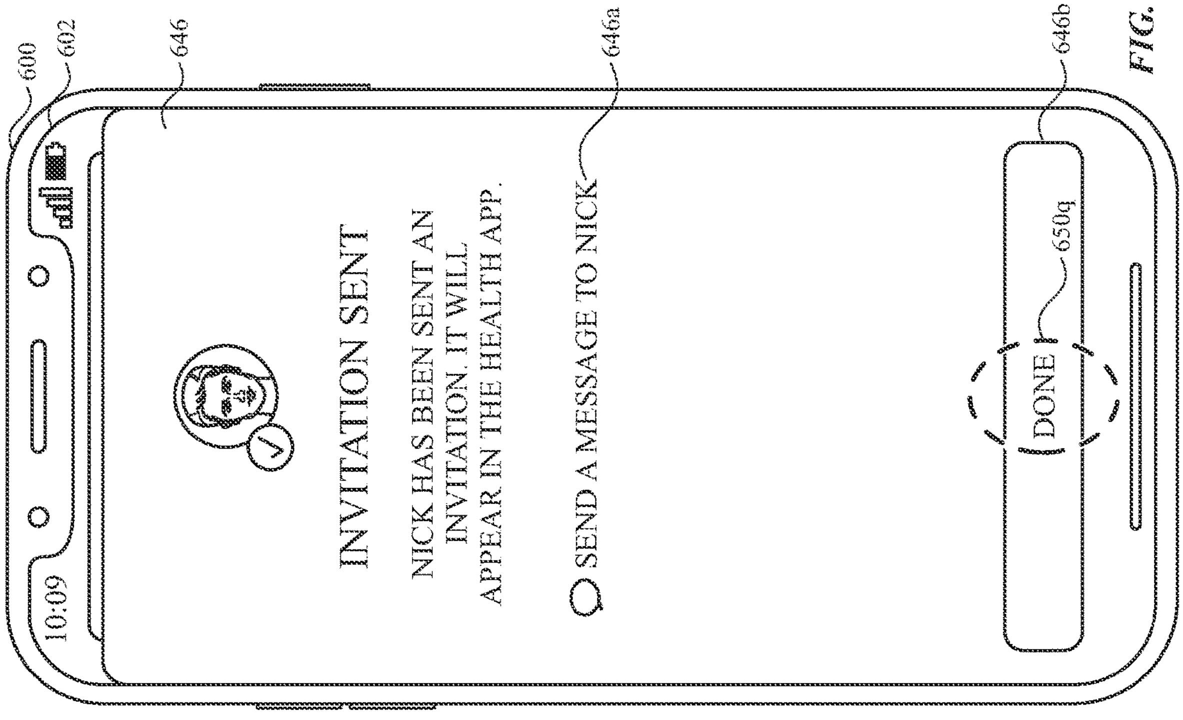

Returning to FIG. 6O, after device 600 ceases displaying preview user interface 644 and while device 600 is displaying summary user interface 642, device 600 receives tap input 650*ob* corresponding to selection of share affordance 642*c*. In response to detecting tap input 650*ob*, device 600 completes the process for sharing the set of health topics by sending the invitation to receive shared health-related data to designated contact Nick Rivera, as shown in FIG. 6Q. In some embodiments, in FIG. 6O, device 600 receives an input corresponding to selection of cancel affordance 642*d* to cancel the process for sharing health-related data, without sharing the health-related data.

In FIG. 6Q, in response to receiving selection of share affordance 642*c*, device 600 completes the process for sharing the set of health topics and displays completion user interface 646. Completion user interface 646 includes confirmation text detailing that the invitation to receive the set of health topics has been sent to designated contact Nick Rivera, as well as contact affordance 646*a* that, when selected, initiates a process for contacting Nick Rivera. Device 600 receives tap input 650*q* corresponding to selection of done affordance 646*b* and in response, returns to displaying health sharing user interface 614, as shown in FIG. 6R.

Figure 6R:
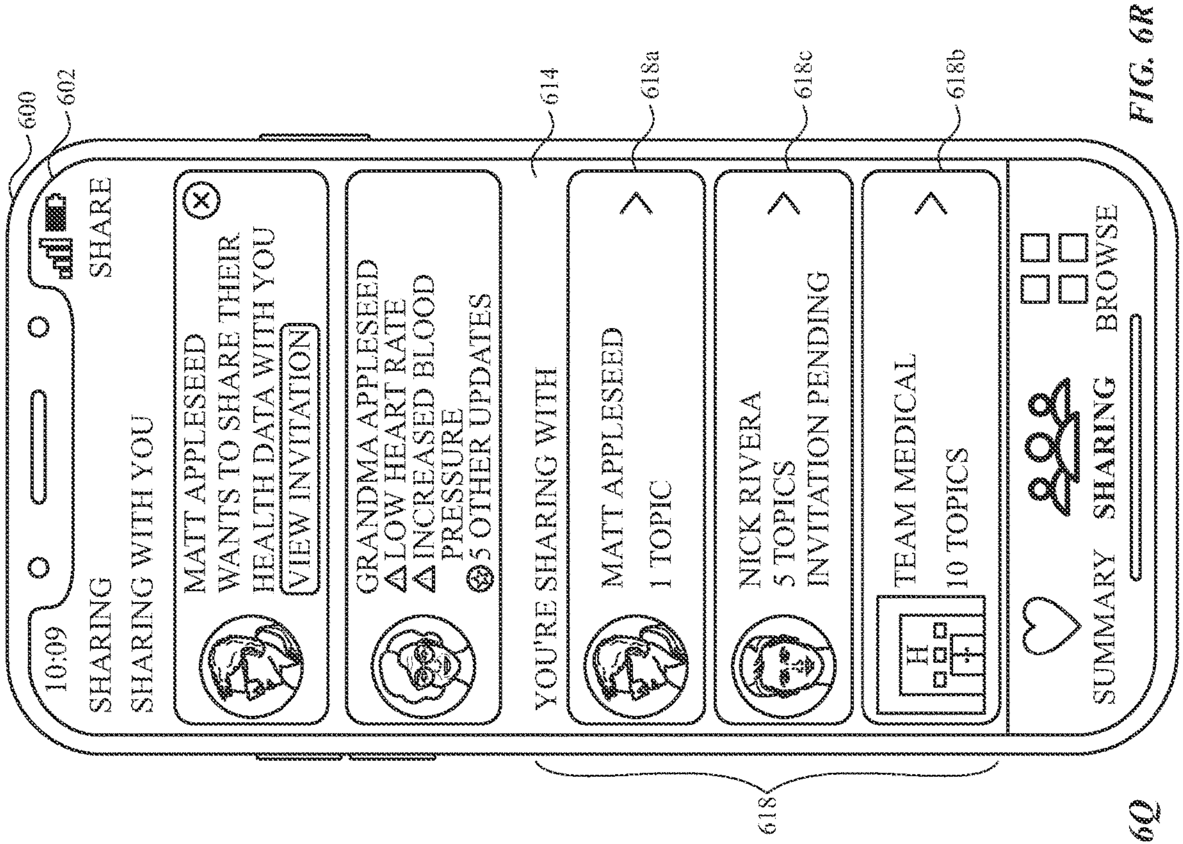

In FIG. 6R, device 600 displays health sharing user interface 614, now with fifth sharing affordance 618*c*, along with third sharing affordance 618*a* and fourth sharing affordance 618*b* as discussed with respect to FIG. 6B, in "You're Sharing with" section 618. Fifth sharing affordance 618*c* indicates that there is an invitation pending for Nick Rivera to receive five topics of shared health-related data associated with the primary user account of device 600 (e.g., Tiffany Smith). "You're Sharing with" section 618 shows the user accounts receiving shared health data, in alphabetical order, followed by medical institutions receiving shared health data. In some embodiments, "You're Sharing with" section 618 is organized with the most recent sharing relationship first, followed by older established sharing relationships.

Figure 6S:
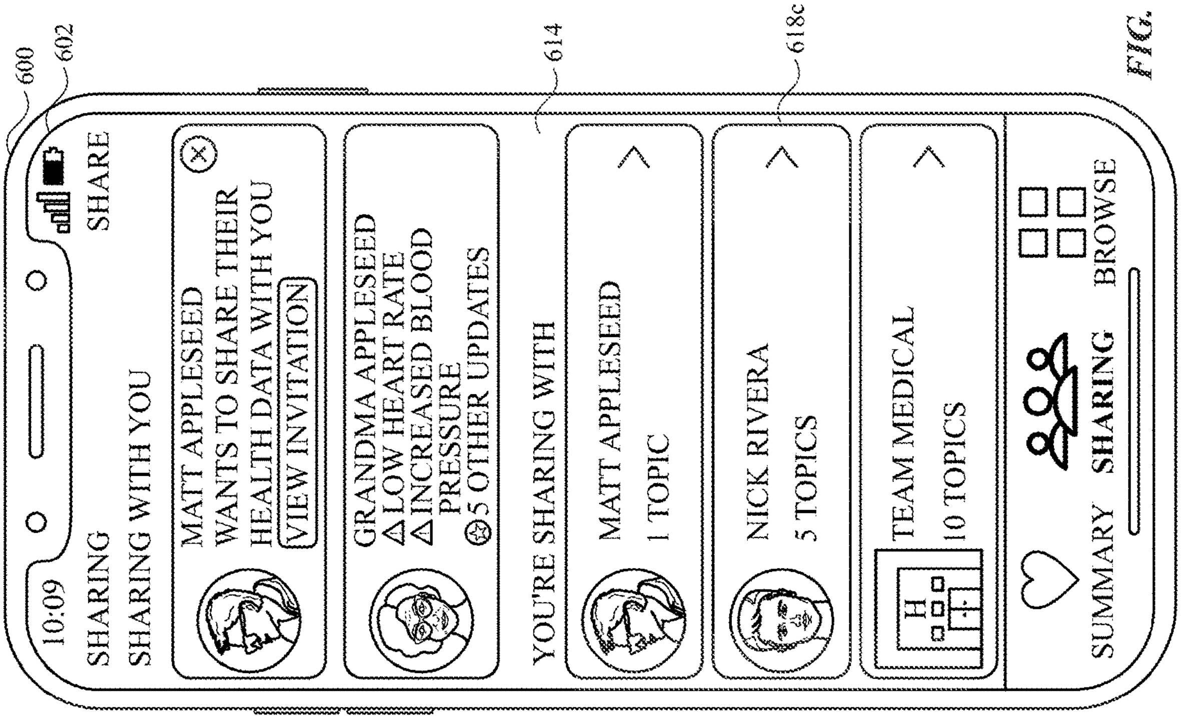

In FIG. 6S, device 600 continues displaying health sharing user interface 614 and now, Nick Rivera has accepted the invitation to receive shared health topics associated with the primary user account, Tiffany Smith. Fifth sharing affordance 618*c* no longer includes the "invitation pending" text and now indicates that Nick Rivera is receiving five topics of shared health-related data associated with the primary user account of device 600.

Turning now to FIG. 6T, device 600 displays all topics user interface 648 in response to receiving tap input 650*fb* corresponding to selection of see all affordance 626*b* in FIG. 6F. All topics user interface 648 includes all affordance 648*a*, which is shown in an emphasized state (e.g., selected state; a state with a border around affordance 648*a*), and existing data affordance 648*b*, which is shown in an inactive state (e.g., without a border). In some embodiments, device 600 receives an input corresponding to selection of existing data affordance 648*b* and in response, updates existing data affordance 648*b* to an emphasized state, updates all affordance 648*a* to an inactive state (e.g., all affordance 648*a* and existing data affordance 648*b* are mutually exclusive toggles), and displays a listing of health topics containing data entries corresponding to the user account of the primary user, without displaying health topics that do not contain data entries corresponding to the user account of the primary user. When all affordance 648*a* is shown in an emphasized state, as in FIG. 6T, all topics user interface 648 includes a listing of all health topics for sharing, including health topics without data entries corresponding to the user account of the primary user. In some embodiments, additional filter options are displayed, such as a recent data filter or a manually entered data filter, for providing health topics based on different criteria. In some embodiments, device 600 receives a swipe input and in response, scrolls all topics user interface 648 to reveal additional health topics for sharing. In some embodiments, device 600 receives one or more inputs corresponding to selection of one or more toggles within the data type rows to enable sharing of one or more health topics. In some embodiments, device 600 further receives an input corresponding to selection of the next affordance and in response, displays a summary user interface that details the set of health topics selected for sharing via all topics user interface 648, similar to summary user interface 642 of FIG. 6O.

FIG. 7 is a flow diagram illustrating a method for managing shared health-related data using a computer system in accordance with some embodiments. Method 700 is performed at a computer system (e.g., 100, 300, 500, 600) (e.g., a smart phone, a smart watch) that is in communication with a display generation component (e.g., 112, 340, 504, 602) (e.g., a display controller, a touch-sensitive display system; and/or a display (e.g., integrated or connected)) and one or more input devices (e.g., 112, 116, 350, 355, 359, 534, 536, 538, 602) (e.g. gyroscope, accelerometer, microphone, and/or a touch-sensitive surface). Some operations in method 700 are, optionally, combined, the orders of some operations are, optionally, changed, and some operations are, optionally, omitted.

As described below, method 700 provides an intuitive way for managing shared health-related data. The method reduces the cognitive burden on a user for managing shared health-related data, thereby creating a more efficient human-machine interface. For battery-operated computing devices, enabling a user to managing shared health-related data faster and more efficiently conserves power and increases the time between battery charges.

The computer system receives (702), via the one or more input devices (e.g., 602), a first set of one or more inputs (e.g., 650*b*, 650*b*) (e.g., tap inputs) that correspond to a request to initiate a process for sharing a set of health-related data (e.g., as initiated by selection of share affordance 614*a* of FIG. 6B) (e.g., a process for sharing health-related data associated with a first user account of a first user (e.g., belonging to the first user (e.g., that is associated with data pertaining to the first user); a user of the computer system)).

In response to receiving the first set of one or more inputs (704), the computer system displays (706), via the display generation component (e.g., 602), a first data selection user interface (e.g., 628, 630, 632) that includes: in accordance with a determination that a first data type (e.g., the suggestions listed on user interface 628 of FIG. 6G) satisfies a first set of criteria (708) (e.g., existence (e.g., a utilized data type via manual input or input via an external device that is in communication with the computer system (e.g., smart watch; blood glucose monitor, smart scale)); recency (e.g., data input within the last 6 months); enabled feature (e.g., health alerts)), a first selectable user interface object (e.g., the toggles within rows 628*b*-628*f* of FIG. 6G) that corresponds to the first data type (e.g., activity rings, weight, low heart rate) and that, when selected, modifies the sharing status (e.g., whether data of the first data type is shared or not shared) of the first data type in the process for sharing the set of health-related data. In some embodiments, in accordance with a determination that the first data type does not satisfy the first set of criteria, the computer system forgoes displaying the first selectable user interface object in the data selection user interface).

In response to receiving the first set of one or more inputs (704), the computer system displays (706), via the display generation component (e.g., 602), a first data selection user interface (e.g., 628, 630, 632) that includes: in accordance with a determination that a second data type (e.g., the suggestions listed on user interface 628 of FIG. 6G) (e.g., a data type different than the first data type) satisfies the first set of criteria (710), a second selectable user interface object (e.g., the toggles within rows 628*b*-628*f* of FIG. 6G) that corresponds to the second data type (e.g., steps, blood oxygen, high heart rate) and that, when selected, modifies the sharing status (e.g., whether data of the second data type is shared or not shared) (modifies without affecting the sharing status of the first data type) of the second data type in the process for sharing the set of health-related data. In some embodiments, in accordance with a determination that the second data type does not satisfy the first set of criteria, the computer system forgoes displaying the second selectable user interface object in the data selection user interface. In some embodiments, the first user and second user described in with respect to method 900 perform method 700 prior to displaying the first and second selectable user interface objects of method 900.). In some embodiments, including (or not including) a selectable user interface object in a data selection user interface based on a first set of criteria being met provides users with the potentially most relevant selectable user interface object candidates for selection, without the user having to search for those candidates. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set of criteria includes a criterion that is satisfied when the first data type includes user data that was created or modified within a predetermined time period (e.g., data within 604*a*, 604*b*, 604*c*, 604*d* of FIG. 6A) (e.g., user data from a recent period of time (e.g., 6 months; 1 year)). In some embodiments, displaying selectable user interface objects that correspond to data types that meet creation or modification criterion allows the user to quickly recognize potentially significant data types and reduces the number of inputs required to identify and display potentially significant data types. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the first selectable user interface object and/or displaying the second selectable user interface object (e.g., the toggles within 628*b* and 628*d* of FIG. 6G), the computer system receives a second set of one or more inputs (e.g., 650*ga* and 650*gb*, 650*ob*). In response to the second set of one or more inputs, the computer system: completes the process for sharing the set of health-related data (e.g., as indicated by user interface 646 of FIG. 6Q); and shares the set of health-related data with at least one external computer system (e.g., as indicated by 618*c* of FIG. 6R) (e.g., a smart phone, a smart watch that is associated with a different user than the user of the computer system) (e.g., sharing selected health-related data associated with a first user account of a first user (e.g., belonging to the first user (e.g., that is associated with data pertaining to the first user) with a second account of a second user (e.g., the second user selected by the first user)), wherein: in accordance with a determination that the second set of one or more inputs includes a first input (e.g., 650*ga*) that corresponds to selection of the first selectable user interface object that corresponds to the first data type, the set of health-related data that is shared includes shared data of the first data type (e.g., 628*b* in the HEALTH TOPICS section of FIG. 6O) (e.g., the first data type is shared with the selected contact); and in accordance with a determination that the second set of one or more inputs includes a second input (e.g., 650*gb*) that corresponds to selection of the second selectable user interface object that corresponds to the second data type, the set of health-related data that is shared includes shared data of the second data type (e.g., 628*d* in the HEALTH TOPICS section of FIG. 6O) (e.g., the second data type is shared with the selected contact). In some embodiments, in accordance with a determination that the second set of inputs did not include selection of the first selectable user interface object, the shared data does not include any data of the first type. In some embodiments, in accordance with a determination that the second set of inputs did not include selection of the second selectable user interface object, the shared data does not include any data of the second type. In some embodiments, the shared data includes data of both the first and second data types, when both are selected. In some embodiments, activating health-related data sharing via a set of one or more inputs ensures that information required to properly share the selected data types is received, thereby ensuring proper sharing and reducing errors. Ensuring proper activation of functions and reducing errors enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first type of data is selected from the group consisting of: user-entered data (e.g., the data types suggested on user interface 634 of FIG. 6K) (e.g., data entered manually via a software or hardware keyboard), data collected by one or more sensors (e.g., 168) that are in communication with the computer system (e.g., sensors that are integrated into the computer system, sensors that are wirelessly connected to the computer system), data transmitted by one or more external devices (e.g., 500) (e.g., a smart watch; a dedicated diagnostic device (e.g., a continuous glucose monitor, a sleep tracker)), and a combination thereof. In some embodiments, utilizing various methods for data collection provides the computer system with ample data for creating data entries pertaining to a data type, which enhances the operability of the computer system. Enhancing the operability of the device makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first data type and the second data type satisfy a first set of grouping criteria (e.g., relating to ACTIVITY AND MOBILITY of FIG. 6G) (e.g., both the first and second data types are categorized within a first genus of data (e.g., both data types are physical activity data types (e.g., total calories burned, total active minutes) or both data types are heart-related data types (e.g., EKG data or heart rate data))). In some embodiments, the first and second data types do not satisfy the second set of grouping criteria. After displaying the first data selection user interface (e.g., 628), the computer system displays a second user selection user interface (e.g., 630) that includes: a third selectable user interface object that corresponds to a third data type (e.g., the toggle within the WEIGHT row of FIG. 6I) and that, when selected, modifies the sharing status of the third data type in the process for sharing the set of health-related data, wherein the third data type satisfies a second set of grouping criteria but does not satisfy the first set of grouping criteria (e.g., relating to BASIC HEALTH MEASUREMENTS of FIG. 6I and not relating to ACTIVITY AND MOBILITY of FIG. 6G) (e.g., the third data type belongs in a second genus of data, but does not belong in the same genus of data as the first and second data types); and a fourth selectable user interface object that corresponds to a fourth data type (e.g., the toggle within the BLOOD OXYGEN row of FIG. 6I) and that, when selected, modifies the sharing status of the fourth data type in the process for sharing the set of health-related data, wherein the fourth data type satisfies the second set of grouping criteria but does not satisfy the first set of grouping criteria (e.g., relating to BASIC HEALTH MEASUREMENTS of FIG. 6I and not relating to ACTIVITY AND MOBILITY of FIG. 6G) (e.g., the fourth data type belongs to the same genus of data as the third data type, but does not belong in the same genus of data as the first and second data types). In some embodiments, displaying data types based on a grouping criteria enables the user to identify related data types without cluttering the user interface with unrelated data types. Providing improved visual feedback to the user without cluttering the user interface enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to displaying the first data selection user interface (e.g., 628), the computer system displays a fifth selectable user interface object (e.g., 626*b*) (e.g., a "see all data types" option). In some embodiments, the computer system receives a third set of one or more user inputs that includes an input (e.g., 650*fb*) corresponding to the fifth selectable user interface object. In response to receiving the third set of one or more user inputs, the computer system displays a third data selection user interface (e.g., 648) (e.g., an interface that presents data types belonging to a plurality of different data type categories (e.g., data types that belong to different general health categories)) that includes: a sixth selectable user interface object that corresponds to the first data type (e.g., the toggle within the ACTIVITY data type row of FIG. 6T) (e.g., a data type that satisfies the first set of grouping criteria) and that, when selected, modifies the sharing status of the first data type in the process for sharing the set of health-related data, and a seventh selectable user interface object that corresponds to the third data type (e.g., the toggle within the WEIGHT data type row of FIG. 6T) (e.g., a data type that satisfies the second set of grouping criteria but does not satisfy the first set of grouping criteria) and that, when selected, modifies the sharing status of the third data type in the process for sharing the set of health-related data. In some embodiments, displaying a user interface that includes data types that satisfy different grouping criteria enables the user to quickly select one or more data types for sharing without viewing multiple grouping-specific user interfaces. Providing additional control options without displaying multiple user interfaces enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first data selection user interface (e.g. 628) includes an eighth selectable user interface object (e.g., a "see all" affordance similar to 626*b*). The computer system receives a user input corresponding to the eighth selectable user interface object (e.g., a tap at 628*g* in FIG. 6G) (e.g., a "see all" option that enables display of all data types in a common data type category, even for data types that did not meet the criteria for initial display). In response to receiving the user input corresponding to the eighth selectable user interface object, the computer system displays a ninth user selectable user interface object (e.g., the toggle within CYCLING DISTANCE of FIG. 6T, on a user interface similar to 648 containing data types related to ACTIVITY AND MOBILITY of FIG. 6G) that corresponds to a fifth data type and that, when selected, modifies the sharing status of the fifth data type in the process for sharing the set of health-related data, wherein: the fifth data type satisfies the first set of grouping criteria (e.g., related to ACTIVITY AND MOBILITY of FIG. 6G) (e.g., the fifth data type belongs to the same data type genus as the first and second data types) (in some embodiments, and does not satisfy the second set of sharing criteria), and the fifth data type does not satisfy the first set of criteria (e.g., the fifth data type does not include any data that is recent). In some embodiments, displaying an option to view all data types, regardless of satisfying the first set of criteria, provides the user with additional controls for sharing various data types. Providing additional control options enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first selectable user interface object and the second selectable user interface object are independently selectable (e.g., by inputs 650*ga* and 650*gb*, respectively) to modify the sharing status of the respective type of data (e.g., as shown by the toggles of 628*b* and 628*d* in the ON position in FIG. 6H). In some embodiments, a user can select either the first data type, the second data type (without selecting the first), neither data type, or both data types for sharing as part of the set of health-related data. In some embodiments, the user can select a "turn on all" user interface object that enables sharing of all suggested data types displayed on the data selection user interface.

In some embodiments, after displaying the first selection user interface (In some embodiments, after displaying user interfaces for all other categories of health-data other than laboratory data) and before completing the process for sharing the set of health-related data, displaying a third data selection user interface (e.g., 636) (e.g., different from the first data selection user interface; different from the second data selection user interface) that includes: a first laboratory results selectable user interface object (e.g., the toggle within 636*a*) that corresponds to a first laboratory results data type (e.g., data from laboratory results that has been transmitted to the computer system from one or more testing laboratories) and that, when selected, modifies the sharing status of the first laboratory results data type in the process for sharing the set of health-related data; and a second laboratory results selectable user interface object (e.g., the toggle within 636*b*) that corresponds to a second laboratory results data type (e.g., data from laboratory results that has been transmitted to the computer system from one or more testing laboratories) and that, when selected, modifies the sharing status of the second laboratory results data type in the process for sharing the set of health-related data. In some embodiments, laboratory results are presented separately from other health-related data categories. In some embodiments, displaying more than one selectable user interface objects for laboratory results provides the system with the capability to enable sharing of multiple laboratory results from one user interface, thereby increasing the control options available to the user via the user interface. Providing additional control options enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first laboratory results selectable user interface object and the second laboratory results selectable user interface object are independently selectable (e.g., by tap inputs on the toggle within 636*a* and the toggle within 636*b* in FIG. 6L) to modify the sharing status of the respective type of laboratory results data. In some embodiments, a user can select either the first data type, the second data type (without selecting the first), neither data type, or both data types for sharing as part of the set of health-related data.

In some embodiments, the third data selection user interface (e.g., 636) includes a tenth selectable user interface object (e.g., 636*e*) (e.g., "share all" affordance). The computer system receives a user input (e.g., 650*l*) corresponding to selection of the tenth selectable user interface object (e.g., 636*e*); in response to the user input corresponding to selection of the tenth selectable user interface object, the computer system displays a confirmation user interface (e.g., 638) that includes a confirmation selectable user interface object (e.g., the toggle within 638*a*) that, when selected, modifies the sharing status for all laboratory results data types (e.g., sharing all current and future entries pertaining to laboratory data (e.g., lab results)). In some embodiments, selection of the confirmation selectable user interface object modifies the status for a plurality, but less than all, of laboratory results data types (e.g., future laboratory results without past laboratory results). In some embodiments, allowing the user to select a user interface object to modify the sharing status of all laboratory results reduces the number of inputs required to share all laboratory results. Providing additional control options without requiring additional user inputs enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after displaying the first data selection user interface (e.g., 628) and before completing the process for sharing the set of health-related data, the computer system displays a fourth data selection user interface (e.g., 640) (e.g., different from the first and second data selection user interface; different from the third data selection user interface) that includes a tenth selectable user interface object (e.g., 640*a*, 640*b*) (e.g., an "enable notifications" sharing affordance) that, when selected, modifies the sharing status (e.g., modifies whether such notifications are shared with a selected contact when the notification is provided at the computer system) for health-related notifications (e.g., fall detection, heart-related (e.g., abnormal heart rate or ECG data), cardio fitness, noise, and/or environmental hazard exposure notifications) of a first type that are provided at the computer system. In some embodiments, the fourth data selection user interface (e.g., 640) includes a plurality of objects that each correspond to a different type of notification (e.g., 640*a*, 640*b*). In some embodiments, allowing the user to select a user interface object to modify the sharing status of health-related notifications reduces the number of inputs and user interfaces required to share health-related notifications. Providing additional control options without requiring additional user inputs and user interfaces enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to displaying the first data selection user interface (e.g., 628), the computer system displays a contact selection user interface (e.g., 624) that includes: a first contactable user selectable user interface object that satisfies a set of contact grouping criteria (e.g., 624*c*) (e.g., a set of criteria that includes a criterion that is satisfied when the first contact has a user account that shares a family account with the first user of the computer system; a criterion that is satisfied when the first contact has a user account that is in frequent contact with the first user of the computer system) (e.g., family, relatives, important people who are not work-related) and that, when selected (e.g., by input 650*e*), designates a first contactable user (e.g., NICK RIVERA of 624*c*) as a recipient for the set of health-related data; and a second contactable user selectable user interface object (e.g., 624*a*, 624*b*) that satisfies the set of contact grouping criteria and that, when selected, designates a second contactable user (e.g., a contact for a user that is stored in a contacts database accessible to the computer system) as a recipient for the set of health-related data. In some embodiments, a third contactable user that is accessible to the computer system that does not meet the set of contact grouping criteria is not included in the contact selection user interface. In some embodiments, displaying contactable user selectable user interface objects that satisfy a set of contact grouping criteria allows the user to quickly recognize potentially significant contactable users and reduces the number of inputs required to identify and display potentially significant contactable users. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the process for sharing the set of health-related data includes designating a single contactable user (e.g., NICK RIVERA of 624*c*) to receive the set of health-related data (e.g., per single iteration of the process. In some embodiments, the process can be re-initiated for a second iteration to designate a different contactable user to also receive the set of health-related data). In some embodiments, both the first contactable user (e.g., 624*c*) and the second contactable user (e.g., 624*a*, 624*b*) cannot be, via the contact selection user interface (e.g., 624), concurrently designated as recipients for the set of health-related data. In some embodiments, selection of the first contactable user selectable user interface object de-selects the second contactable user selectable user interface object, if that object is currently selected, and vice versa.

In some embodiments, prior to completing the process for sharing the set of health-related data, the computer system displays a summary user interface (e.g., 642), wherein the summary user interface includes indications of the data types (e.g., 628*b*, 628*d*, 632*a*, 638*c*, 640*e* of FIG. 6O) that have been selected to be included in the set of health-related data for sharing upon completion of the process for sharing the set of health-related data. In some embodiments, a list/summary of the types of data and/or notifications that will be shared on completion of the sharing process is displayed prior to the start of sharing. In some embodiments, displaying a summary user interface that includes indications of the selected data types for sharing provides enhanced feedback to the user to ensure proper sharing, thereby reducing errors. Providing improved feedback and reducing errors enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the summary user interface includes an eleventh selectable user interface object (e.g., 642*a*) (e.g., a "preview" affordance). In some embodiments, the computer system receives an input (e.g., 650*oa*) corresponding to the eleventh selectable user interface object (e.g., 642*a*) and in response receiving the input corresponding to the eleventh selectable user interface object, the computer system displays a preview user interface (e.g., 644), wherein the preview user interface includes a graphical preview of the set of health-related data (e.g., 604*a*, 604*d*, 604*b* of FIG. 6P) as it would be presented to a designated recipient of the set of health-related data after completion of the process for sharing the set of health-related data. In some embodiments, the graphical preview includes one or more visual characteristics (e.g., a color, a pattern of colors) that is based on the data types that have been selected for sharing via the process. In some embodiments, displaying a preview user interface that includes a graphical preview of the selected data types as it would be presented to a designated recipient provides enhanced feedback to the user to ensure proper sharing of health-data prior to completing the share process, thereby reducing errors. Providing improved feedback and reducing errors enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the summary user interface (e.g., 642) includes a twelfth selectable user interface object (e.g., 642*b*) (e.g., an "edit" affordance) that when selected, enables modification (e.g., removal or addition of data types) of the data types that have been selected to be included in the set of health-related data for sharing upon completion of the process for sharing the set of health-related data. In some embodiments, providing a selectable user interface object for modifying the selected data types for sharing enables the user to edit the set of health-related data prior to sharing, thereby reducing errors. Providing additional control options and reducing errors enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, during the process for sharing the set of health-related data or after completion of the process for sharing the set of health-related data, the computer system displays a thirteenth user selectable user interface object (e.g., an affordance on user interface 642) that, when selected, initiates a process to request health-related data (e.g., request sharing of health-related data) from a second designated recipient of the set of health-related data (e.g., from the contact selected to receive the set of health-data corresponding to the first user account of the first user of the computer system).

In some embodiments, the computer system completes the process for sharing the set of health-related data. In some embodiments, completion of the process for sharing the set of health-related data causes a first set of health-related data to be shared with a third designated recipient (e.g., NICK RIVERA as selected in FIG. 6E and shown by 618*c* within 618 of FIG. 6R); and completing a second process for sharing a second set of health-related data (e.g., re-initiating and completing the process after completing it a first time), wherein: the second process for sharing the second set of health-related data causes the second set of health-related data to be shared with a fourth designated recipient (e.g., MATT APPLESEED as shown by 618*a* within 618 of FIG. 6R), and the first set of health-related data includes different (e.g., more data types, less data types) data types than those includes in the second set of health-related data.

Note that details of the processes described above with respect to method 700 (e.g., FIG. 7) are also applicable in an analogous manner to the methods described below. For example, method 900 optionally includes one or more of the characteristics of the various methods described above with reference to method 700. For example, the method 700 is performed prior to display of the first and second selectable user interface objects described with respect to method 900. For brevity, these details are not repeated below.

FIGS. 8A-8P illustrate exemplary user interfaces for managing shared health-related data, in accordance with some embodiments. The user interfaces in these figures are used to illustrate the processes described below, including the processes in FIG. 9.

In FIG. 8A, device 600 displays, on touchscreen display 602, lock screen user interface 802 in the unlocked (e.g., after successfully completing authentication (e.g., face authentication)) state, revealing the content of health notification 802*a*. In some embodiments, device 600 is in the locked state and displays lock screen user interface 802 with a limited-content health notification. In the unlocked state, health notification 802*a* includes information regarding Grandma Appleseed's new change in shared health data (e.g., a weight change) and user affordance 804 with Grandma Appleseed's contact photo (e.g., caller ID photo). In some embodiments, device 600 outputs a notification when a sharing contact (e.g., Grandma Appleseed) creates a new data entry after a predetermined period of time (e.g., first weight entry in six weeks). In some embodiments, device 600 outputs a notification when a sharing contact (e.g., Grandma Appleseed) has a change in pattern of data entry (e.g., Grandma Appleseed has daily data entries for Steps, but has not generated a data entry for Steps in two days). In some embodiments, device 600 outputs a notification when the data of a sharing contact (e.g., Grandma Appleseed) follows a trend (e.g., increase, decrease, remains steady) over a predetermined period of time (e.g., weight has decreased over a six month period; heart rate has increased over a four week period).

Figure 8B:
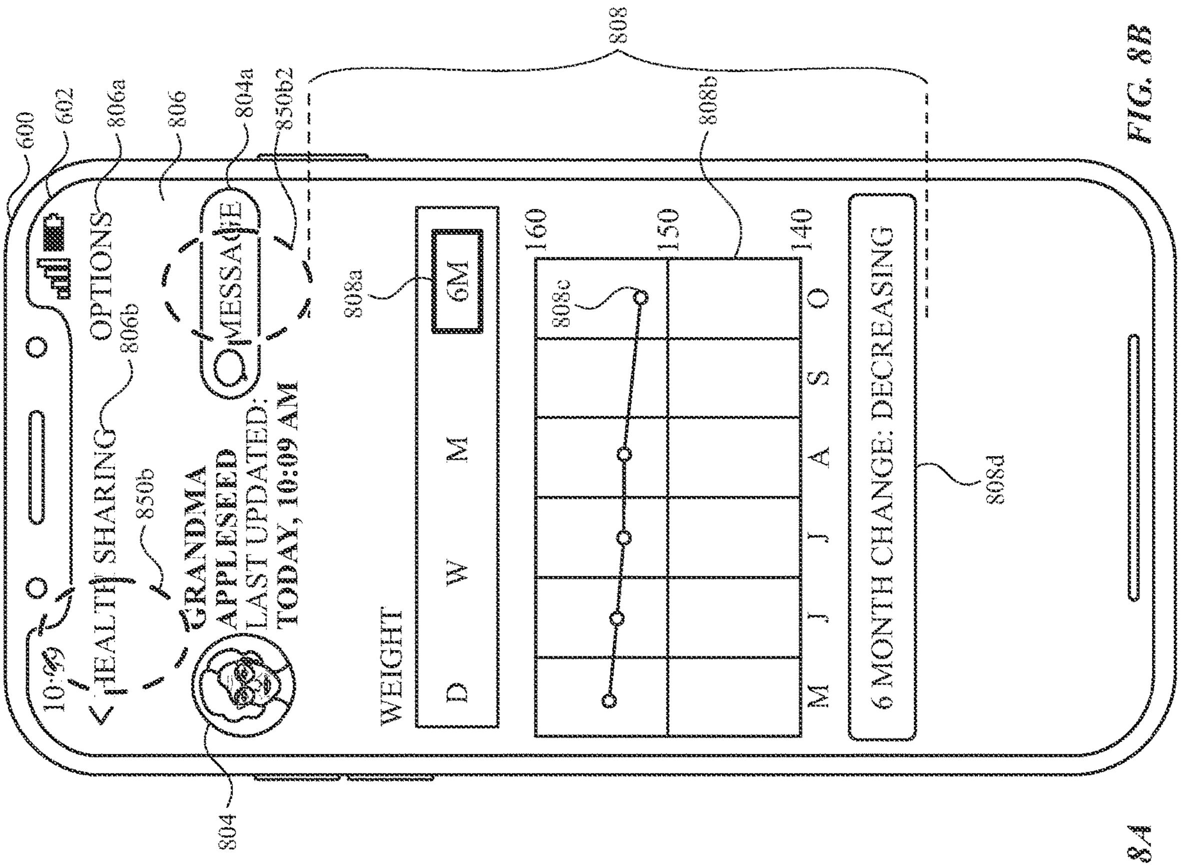
FIGS. 8A-8P illustrate exemplary user interface related to managing and viewing shared health-related data using a computer system, in accordance with some embodiments.
Figure 8A:
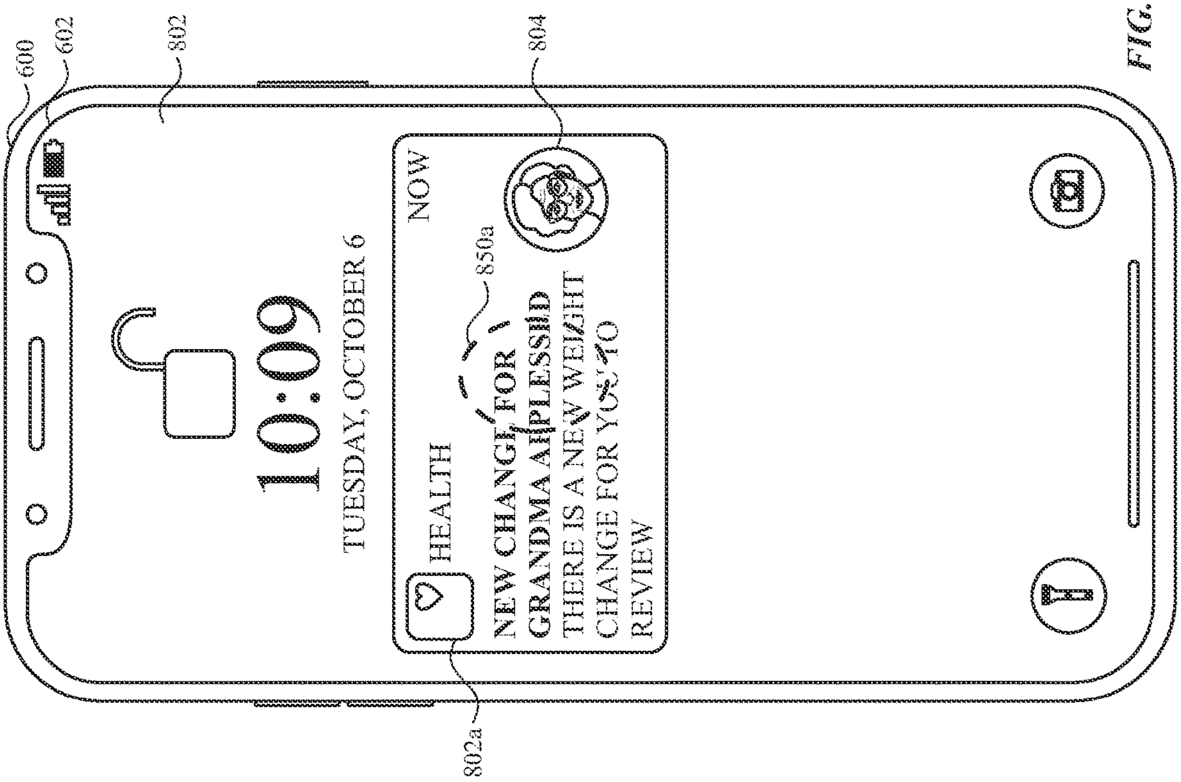

In FIG. 8A, device 600 detects tap input 850*a* corresponding to selection of health notification 802*a* and in response, displays health data user interface 806, as shown in FIG. 8B. In FIG. 8B, device 600 displays health data user interface 806 that includes user affordance 804 and health data region 808. Health data user interface 806 includes user affordance 804 with Grandma Appleseed's contact photo to indicate that the health information shown in health data region 808 pertains to Grandma Appleseed's user account.

In FIG. 8B, on health data user interface 806, health data region 808 shows timeframe affordance 808*a* set at six months (e.g., "6M"), graph 808*b* having data point 808*c*, and trend indication 808*d*. In some embodiments, timeframe affordance 808*a* is set to day (e.g., "D"), week (e.g., "W"), or month (e.g., "M") and the x-axis for time in graph 808*b* is updated accordingly. Data point 808*c* corresponds to the latest weight measurement received by device 600 for Grandma Appleseed. Trend indication 808*d* explains that Grandma Appleseed's weight measurements have decreased for the past six month period.

In FIG. 8B, health data user interface 806 includes options affordance 806*a*. In some embodiments, device 600 receives an input corresponding to options affordance 806*a* and in response, displays an options user interface for modifying settings (e.g., notification settings) relating to receiving shared health data from Grandma Appleseed.

In FIG. 8B, health data user interface 806 also includes contact affordance 804*a* that, when selected, initiates a message for sending to Grandma Appleseed. Device 600 detects tap input 850*b*2 corresponding to selection of contact affordance 804*a* and in response, device 600 displays new message user interface 807 on touchscreen display 602, as shown in FIG. 8B1. New message user interface 807 indicates that the message will be sent to Grandma Appleseed and includes message draft region 807*a* that is prepopulated with weight graph 808*b*. Message draft region 807*a* further includes trend indication 808*d*. In some embodiments, device 600 detects user inputs corresponding to keyboard 807*b* to compose a message (e.g., relating to weight graph 808*b* and/or trend indication 808*d*) for inclusion with weight graph 808*b* and trend indication 808*d* when the message is sent. In some embodiments, device 600 detects a user input corresponding to selection of send affordance 807*c* to send the message containing weight graph 808*b* and trend indication 808*d* to Grandma Appleseed. In some embodiments, device 600 receives notifications similar health notification 802*a* of FIG. 8A, pertaining to other user accounts and/or other trends based on shared data types, and, via the process described with respect to FIG. 8B and FIG. 8B1, initiates a message conversation with the pertinent user account regarding the health notification.

Figure 8C:
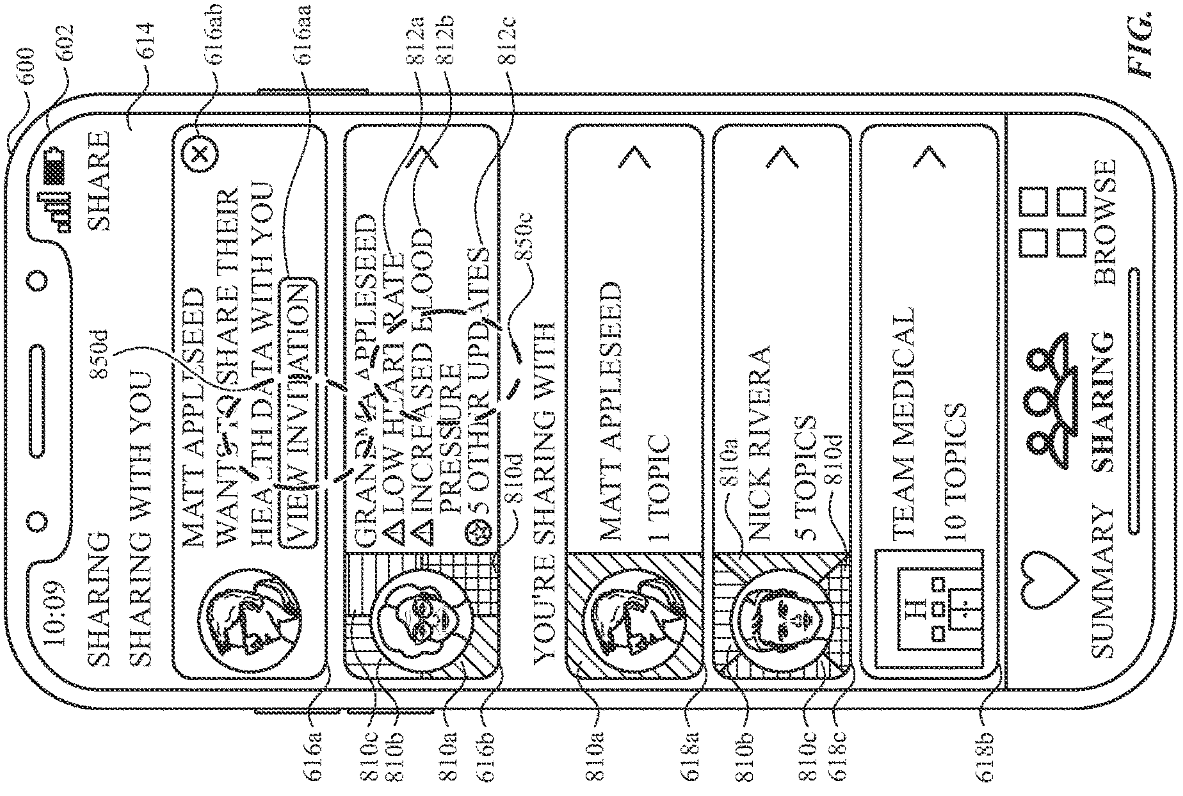

Turning back to FIG. 8B, device 600 detects tap input 850*b* corresponding to selection of health sharing affordance 806*b* and in response, device 600 displays health sharing user interface 614, as shown in FIG. 8C. In FIG. 8C, device 600 displays, on touchscreen display 602, health sharing user interface 614 that includes: first sharing affordance 616*a* as an invitation for receiving Matt Appleseed's shared health-related data; second sharing affordance 616*b* for receiving Grandma Appleseed's shared health-related data; third sharing affordance 618*a* for sharing health-related data with Matt Appleseed; fifth sharing affordance 618*c* for sharing health-related data with Nick Rivera (e.g., via initiating sharing the set of health-related data discussed with respect to FIGS. 6A-6T); and fourth sharing affordance 618*b* for sharing health-related data with Team Medical.

In FIG. 8C, sharing affordances 616*b*, 618*a*, and 618*c* each include a set of one or more colors (as indicated by hatching) that represent the overarching categories of health topics being shared. Notably, first sharing affordance 616*a* does not include colors because health-related data is not yet being received from Matt Appleseed. In some embodiments, first sharing affordance 616*a* includes colors as a preview to the categories of health topics selected for sharing. In second sharing affordance 616*b* corresponding to Grandma Appleseed, four colors (as indicated by hatching) are shown. First color 810*a* represents activity and mobility-related health topics (e.g., activity, workouts, steps, topics detailed with respect to FIG. 6G); second color 810*b* represents heart-related health topics (e.g., heart rate, cardio fitness level, topics detailed with respect to FIG. 6J); third color 810*c* represents Laboratory Results (e.g., COVID-19 test results, blood platelet count results, topics detailed with respect to FIG. 6L); fourth color 810*d* represents Health Alerts (e.g., irregular heart beat alert, low blood pressure alert, fall detection alert, low blood oxygen alert, topics detailed with respect to FIG. 6N). In some embodiments, other colors represent other health categories, such as basic health measurements (e.g., weight, height, topics detailed with respect to FIG. 6I), hearing-related (e.g., environmental sound levels, headphone audio levels), and/or cycle tracking-related (e.g., menstruation, topics detailed with respect to FIG. 6K). In this example, sharing affordances show a maximum of four colors (as indicated by hatching) representing various overarching categories corresponding to health topics that are shared with the primary user account of device 600 or shared from the primary user account of device 600. In some embodiments, the colors are selected based on the overarching categories having the highest number of health topics selected for sharing (e.g., the colors shown represent categories having the most shared topics). In some embodiments, the colors are selected based on the overarching categories having the most active health topics selected for sharing. Third sharing affordance 618*a* indicates that one topic is being shared with Matt Appleseed and includes first color 810*a*, indicating that the one shared topic is an activity and mobility-related data type. In some embodiments, third sharing affordance 618*a* indicates that two (or more) health topics (e.g., cardio fitness and steps) are being shared with Matt Appleseed, yet still includes only first color 810*a* for activity and mobility-related data types, indicating that the two (or more) topics are activity and mobility-related data types.

In FIG. 8C, fifth sharing affordance 618*c* for sharing health-related data with Nick Rivera includes first color 810*a*, second color 810*b*, third color 810*c*, and fourth color 810*d*, which are the same as those in second sharing affordance 616*b* for receiving health-related data from Grandma Appleseed. For visual distinction, the formation of colors 810*a*-810*d* in fifth sharing affordance 618*c* is different from the formation of 810*a*-810*d* second sharing affordance 616*b*. In some embodiments, the colors within sharing affordances animate within the sharing affordance so each sharing affordance is visually distinct and unique, even if the same colors are included (e.g., because the same overarching health categories of health topics are being shared).

In FIG. 8C, in addition to the colors discussed above, second sharing affordance 616*b* for receiving health-related data from Grandma Appleseed includes first notification 812*a*, second notification 812*b*, and third notification 812*c*. First notification 812*a* and second notification 812*b* indicate health alerts (e.g., low heart rate, increased blood pressure) corresponding to Grandma Appleseed. In some embodiments, when initiating sharing with the primary user account of device 600, Grandma Appleseed enabled sharing of health alerts, similar to the health alerts discussed with respect to FIG. 6N. Third notification 812*c* indicates that there are five additional updates pertaining to health data for Grandma Appleseed. In some embodiments, if Grandma Appleseed has three or fewer updates, a notification corresponding to each update is detailed within second sharing affordance 616*b*. In some embodiments, notifications contained within sharing affordances are ranked by importance (e.g., health alerts displayed before a new data entry update). In some embodiments, additional updates that are ranked as less important are grouped into a single notification, such as third notification 812*c*.

Figure 8D:
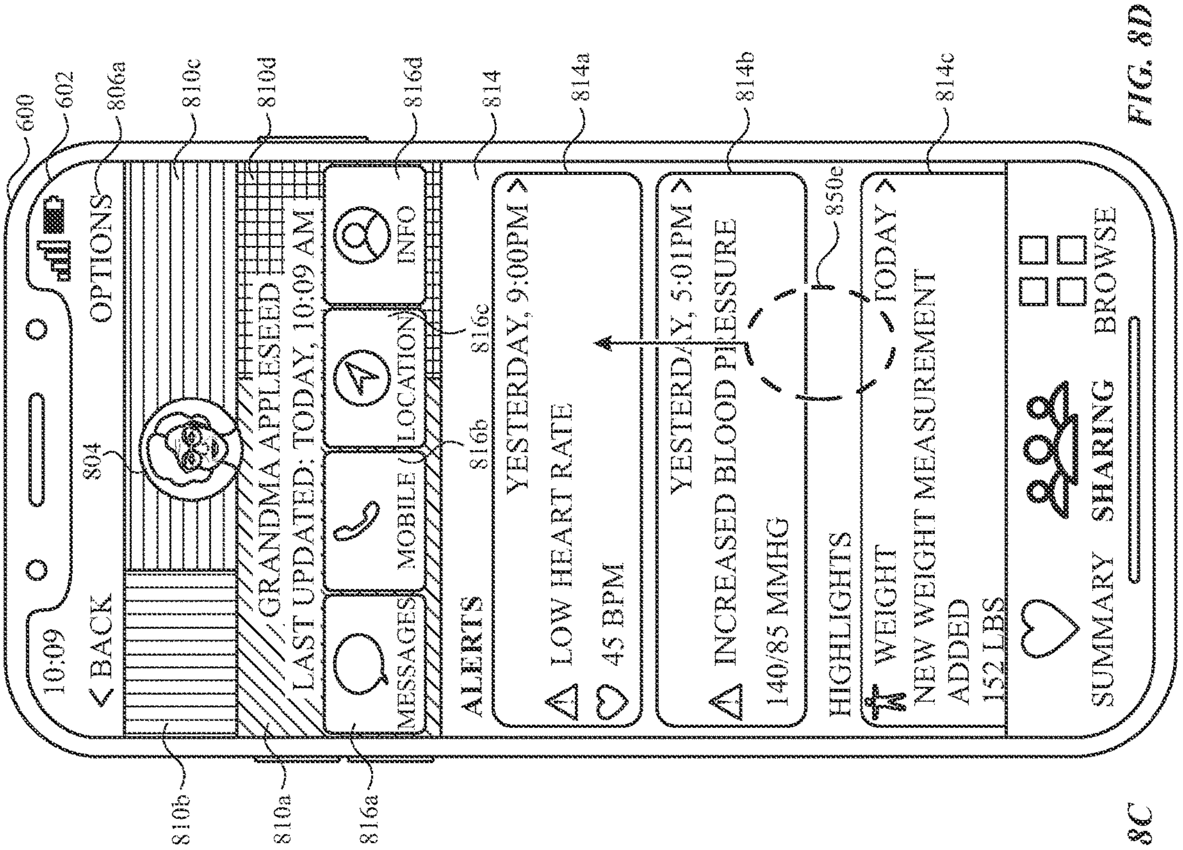
Figure 8F:
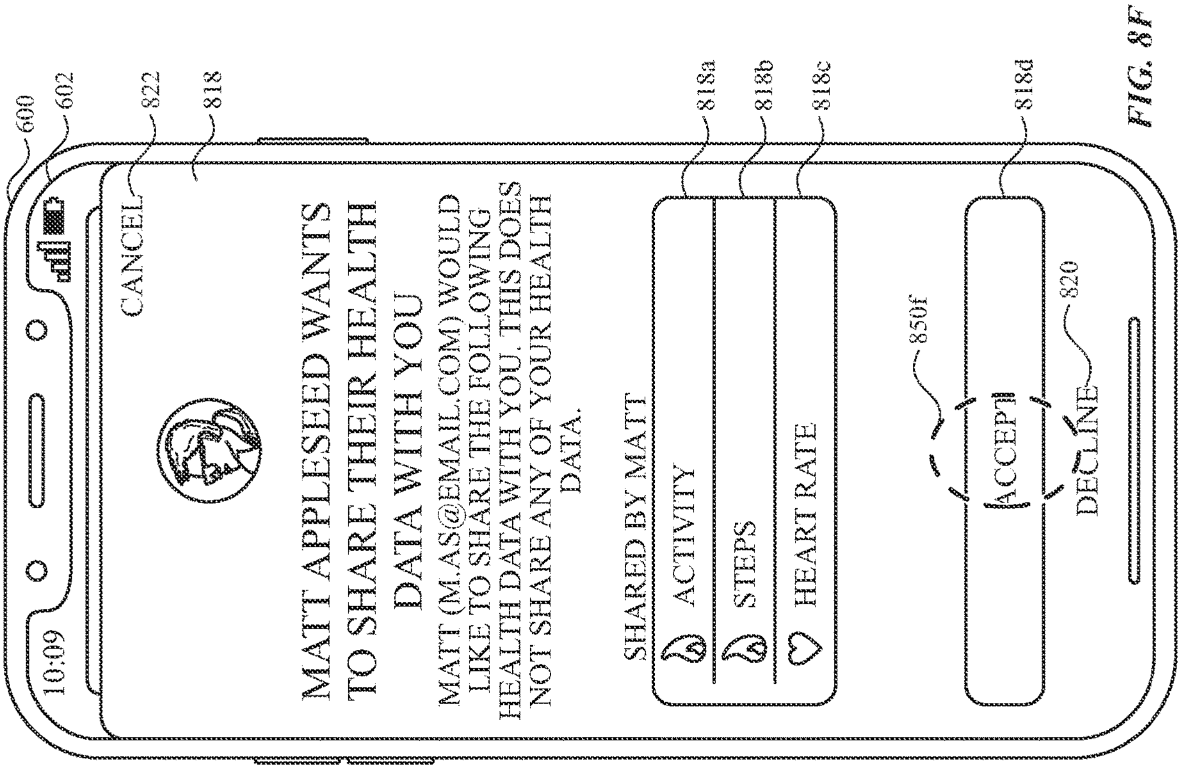

In FIG. 8C, device 600 detects tap input 850*c* corresponding to selection of second sharing affordance 616*b* and in response, displays shared data user interface 814, as shown in FIG. 8D. In FIG. 8C, device 600 detects tap input 850*d* corresponding to selection of view invitation affordance 616*aa* within first sharing affordance 616*a* and in response, displays invitation user interface 816, as shown in FIG. 8F. In some embodiments, device 600 receives an input corresponding to selection of dismiss affordance 616*a* b within first sharing affordance 616*a* and in response, declines the invitation for receiving Matt Appleseed's shared health data. In some embodiments, prior to displaying first sharing affordance 616*a*, Matt Appleseed initiated a process for sharing a set of health-related user data, similar to the process described with respect to FIGS. 6A-6T, and selected Tiffany Smith (e.g., the primary user account of device 600) as the designated recipient.

In FIG. 8D, in response to receiving tap input 850*c*, device 600 displays shared data user interface 814 for reviewing health data shared by Grandma Appleseed with the primary user account of device 600. Shared data user interface 814 includes user affordance 804 with Grandma Appleseed's contact photo (e.g., caller ID photo) to indicate the health data shown is associated with Grandma Appleseed. In some embodiments, device 600 receives an input corresponding to options affordance 806*a* and in response, displays an options user interface for modifying settings (e.g., notification settings) relating to receiving shared health data from Grandma Appleseed. Shared data user interface 814 further includes message affordance 816*a* and call affordance 816*b* that, when selected, initiate a message or phone call, respectively, with Grandma Appleseed. In some embodiments, if Grandma Appleseed shares location with the primary user account of device 600 and device 600 receives an input corresponding to selection of location affordance 816*c*, device 600 displays a location user interface showing the location of Grandma Appleseed. In some embodiments, device 600 receives an input corresponding to selection of contact affordance 816*d* and in response, displays a contact user interface for Grandma Appleseed.

In FIG. 8D, shared data user interface 814 includes first color 810*a*, second color 810*b*, third color 810*c*, and fourth color 810*d* (all represented by hatching) to indicate the overarching categories of the health topics shared by Grandma Appleseed. The health topics shared by Grandma Appleseed are shown on shared data user interface 814, which spans FIG. 8D and FIG. 8E. Grandma Appleseed's shared health topics include: health alerts, as indicated by alert affordance 814*a* for low heart rate (which corresponds to first notification 812*a* of FIG. 8C) and alert affordance 814*b* for increased blood pressure (which corresponds to second notification 812*b* of FIG. 8C); weight, as indicated by weight affordance 814*c*; steps, as indicated by steps affordance 814*d*; blood oxygen, as indicated by oxygen affordance 814*e*; heart rate, as indicated by heart rate affordance 814*f*; and laboratory results, as indicated by blood test affordance 814*g*. In some embodiments, device 600 detects an input corresponding to selection of a health topic affordance and in response, displays a health data user interface detailing historical data entries for the health topic, similar to health data user interface 806 of FIG. 8B. Device 600 detects swipe input 650*e* and in response, scrolls shared data user interface 814 to show additional health topic affordances, as shown in FIG. 8E.

Figure 8E:
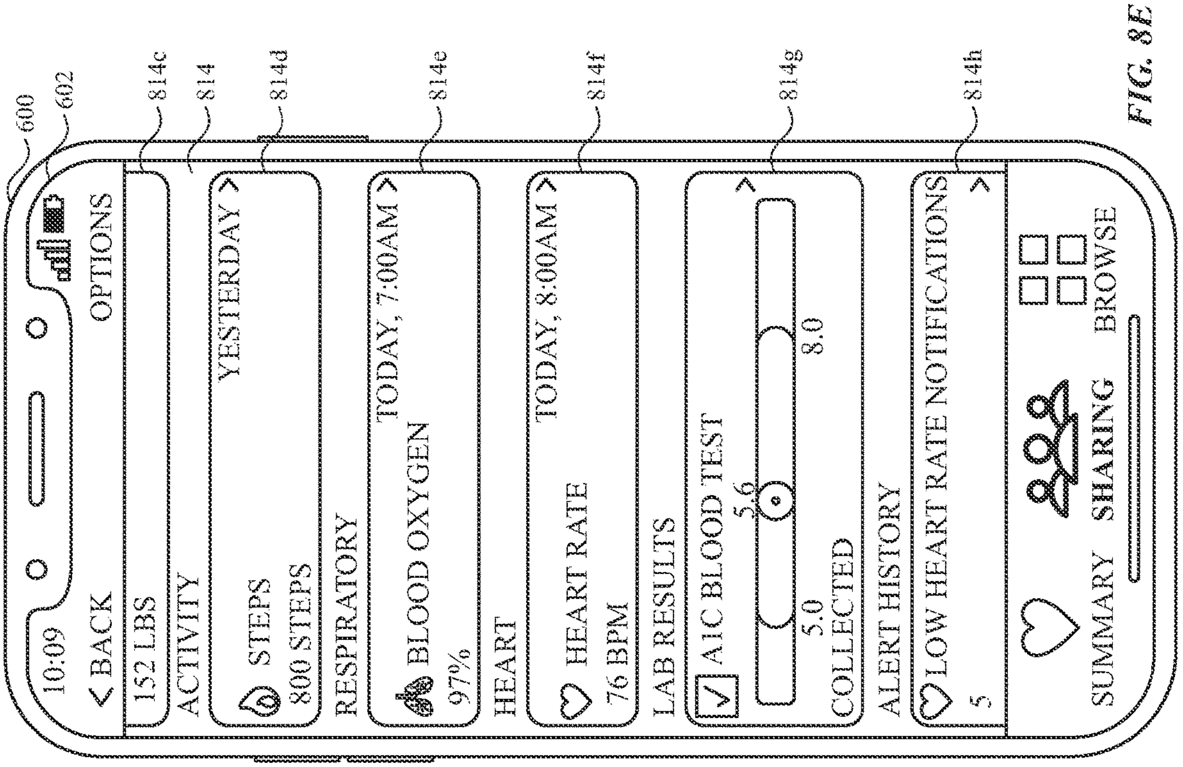

In FIG. 8E, shared data user interface 814 further includes alert history affordance 814*h* that indicates Grandma Appleseed has received five low heart rate alerts (e.g., notifications) in the past. In some embodiments, device 600 detects an input corresponding to selection of alert history affordance 814*h* and in response, displays an alert history user interface that catalogs past health alerts associated with low heart rate for Grandma Appleseed.

Turning now to FIG. 8F, device 600 displays, on touchscreen display 602, invitation user interface 818 in response to receiving tap input 650*d* at FIG. 8C. Invitation user interface 818 contains informational text along with the health data topics selected for sharing from Matt Appleseed. The data types selected for sharing with the primary user account of device 600 are activity 818*a*, steps 818*b*, and heart rate 818*c*. In some embodiments, device 600 receives an input corresponding to cancel affordance 822 and in response, device 600 ceases display of invitation user interface 818 and returns to displaying health sharing user interface 614, as in FIG. 8C. In some embodiments, device 600 receives an input corresponding to selection of decline affordance 820 and in response, device 600 does not enable receipt of Matt Appleseed's shared health data, ceases display of invitation user interface 818, and returns to displaying health sharing user interface 614, as in FIG. 8C, without first sharing affordance 616*a*.

Figure 8G:
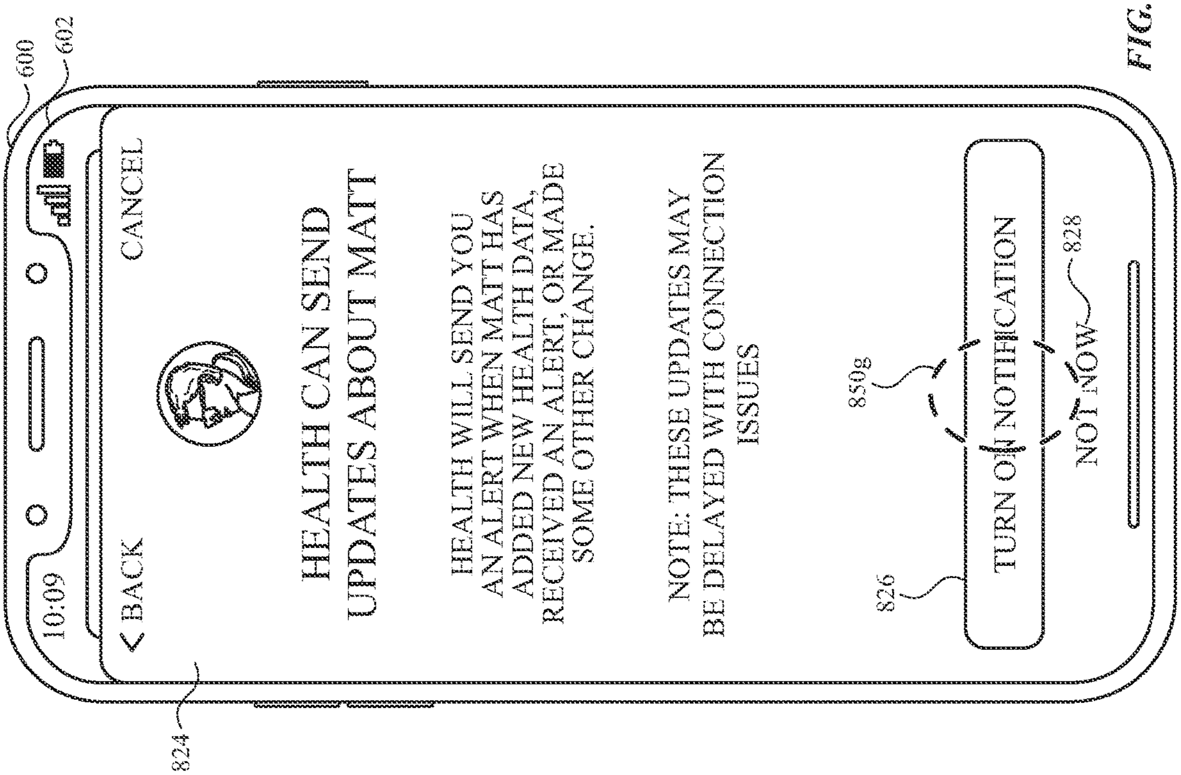

In FIG. 8F, device 600 receives tap input 850*f* corresponding to selection of accept affordance 818*d* and in response, enables receipt of Matt Appleseed's shared health data. In FIG. 8G, in addition to enabling receipt of Matt Appleseed's shared health data, device 600 displays notification set up user interface 624 for enabling notifications related to Matt Appleseed's health data, similar to health notification 802*a* of FIG. 8A. In some embodiments, notifications for the health application must be enabled prior to enabling (e.g., receiving) notifications specific to health sharing. Notification set up user interface 624 includes informational text detailing that notifications may not be delivered immediately due to a lack of connection (e.g., either the sender or receiver does not have cellular service, Wi-Fi, Bluetooth). Device 600 detects tap input 650*g* corresponding to selection of enable notifications affordance 826 and in response, device 600 enables display of notifications relating to shared health data from Matt Appleseed. In some embodiments, device 600 detects an input corresponding to selection of not now affordance 828 and in response, device 600 forgoes enabling of notifications relating to shared health data from Matt Appleseed while continuing to receive shared health data from Matt Appleseed.

Figure 8H:
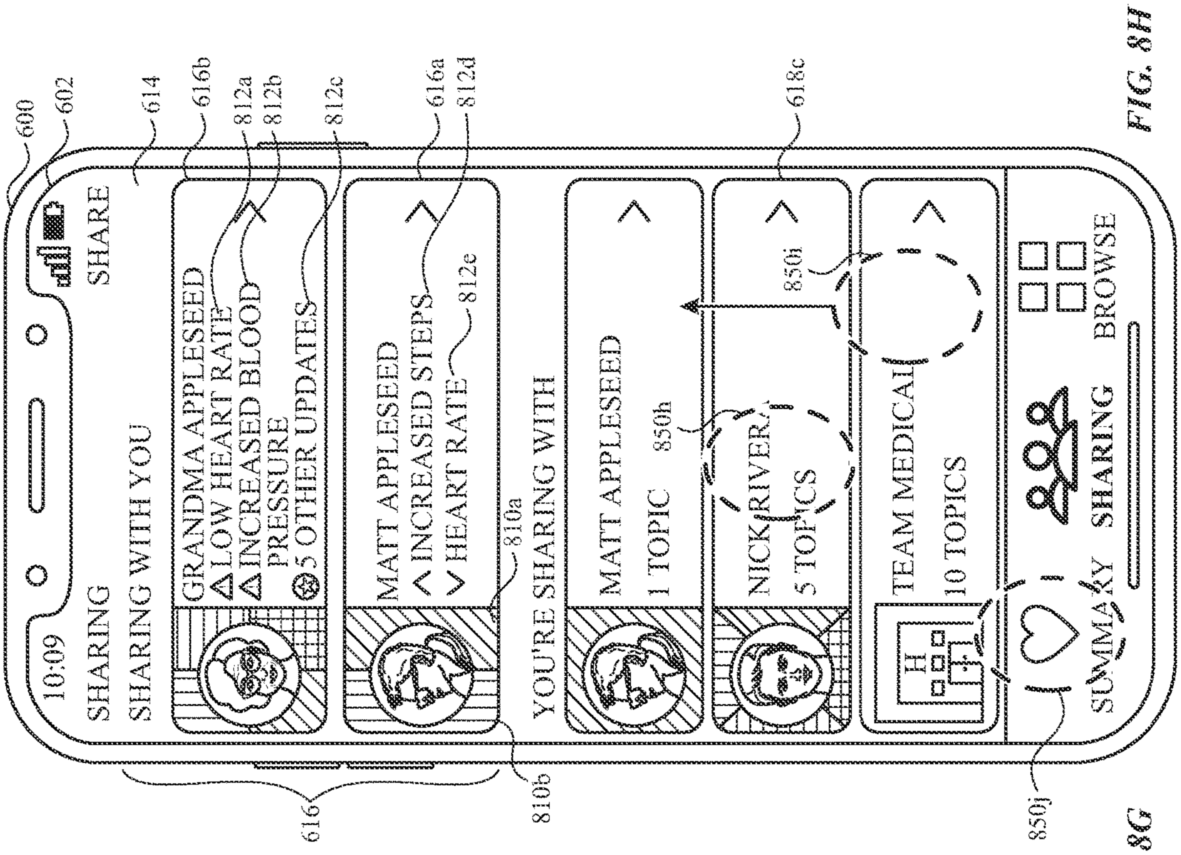

In FIG. 8H, device 600 displays health sharing user interface 614 after accepting the invitation to receive shared health data from Matt Appleseed (in some embodiments, in response to input 850*g*). First sharing affordance 616*a* for Matt Appleseed and second sharing affordance 616*b* for Grandma Appleseed are shown in alphabetical order in "Sharing with You" section 616. In some embodiments, the sharing affordances are arranged based on recency of establishing the sharing relationship (e.g., first sharing affordance 616*a* is listed before second sharing affordance 616*b*). In some embodiments, sharing affordances can be rearranged to accommodate preferences of the primary user of device 600.

In FIG. 8H, first sharing affordance 616*a* for Matt Appleseed contains first color 810*a* (as indicated by hatching) corresponding to activity and mobility-related health topics (e.g., activity 816*a* and steps 816*b* of FIG. 8F) and second color 810*b* (as indicated by hatching) corresponding to heart-related health topics (e.g., heart rate 816*c* of FIG. 8F). In some embodiments, the colors representing categories are sized based on the number of health topics being shared from that category (e.g., first color 810*a* is shown in two thirds of the region around the contact photo, representing two of three shared topics, while second color 810*b* is shown in one third of the region around the contact photo).

In FIG. 8H, first sharing affordance 616*a* for Matt Appleseed contains fourth notification 812*d*, indicating Matt Appleseed's steps have increased, and fifth notification 812*e*, indicating Matt Appleseed's heart rate has decreased. In some embodiments, when there are more updates than space for display, trend updates similar to fourth notification 812*d* and fifth notification 812*e* are grouped as "other updates," similar to third notification 812*c*. In some embodiments, health alerts such as first notification 812*a* and second notification 812*b* are prioritized for display over trend updates. In some embodiments, after reviewing Grandma Appleseed's shared health data in FIGS. 8D and 8E, first notification 812*a*, second notification 812*b*, and third notification 812*c* are no longer shown within second sharing affordance 616*b* for Grandma Appleseed (e.g., notifications are cleared after reviewing a sharing user's health data).

Figure 8I:
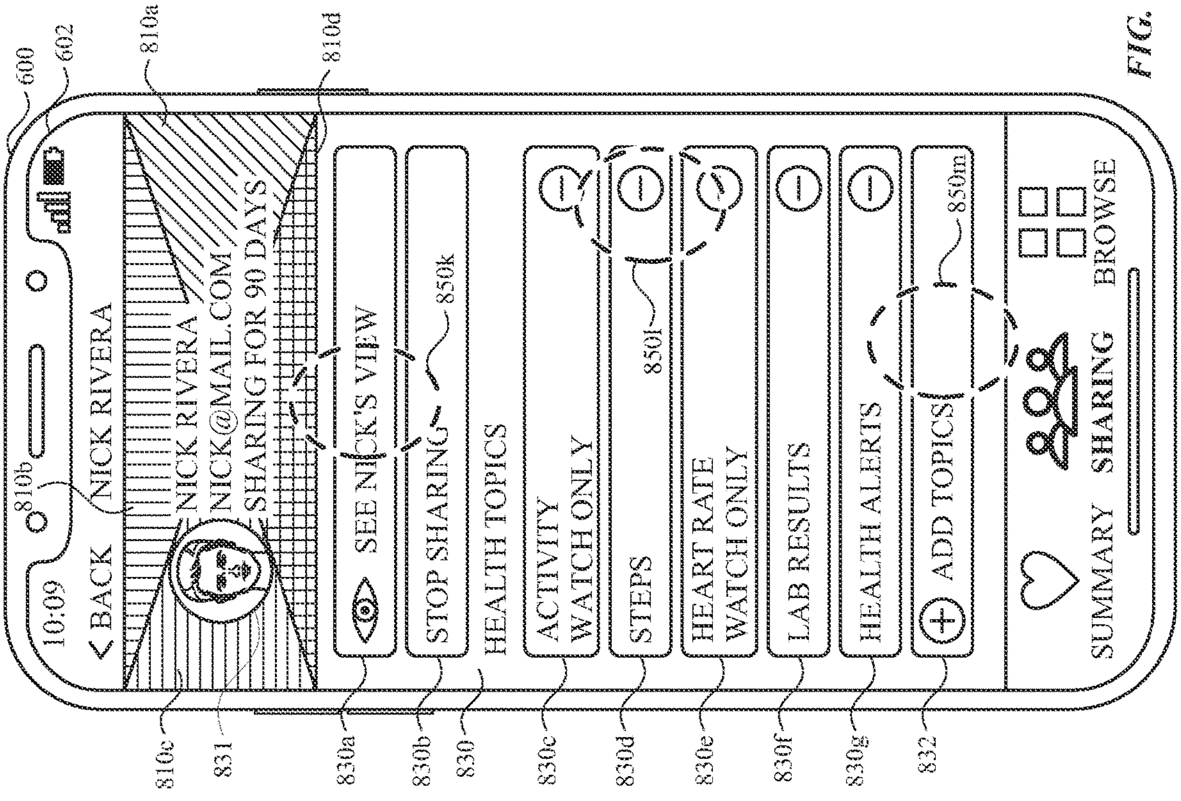
Figure 8J:
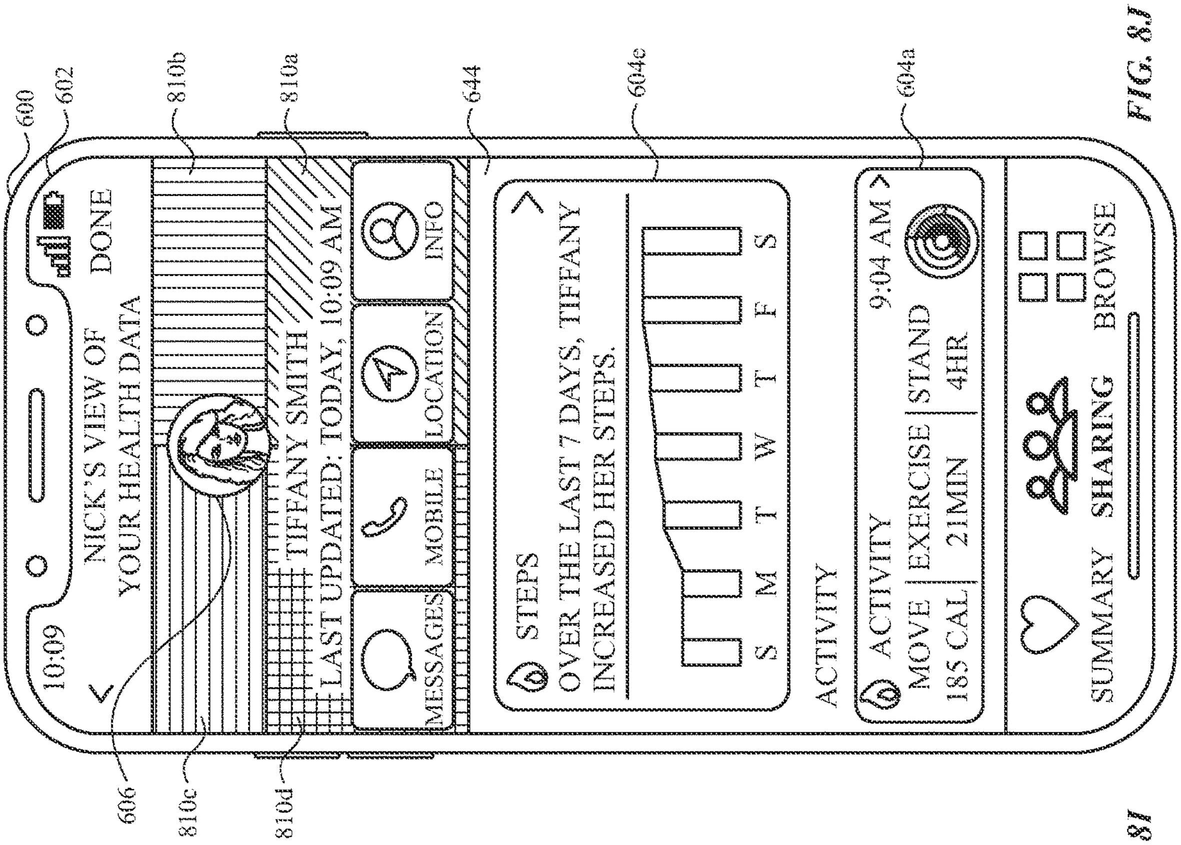
Figure 8L:
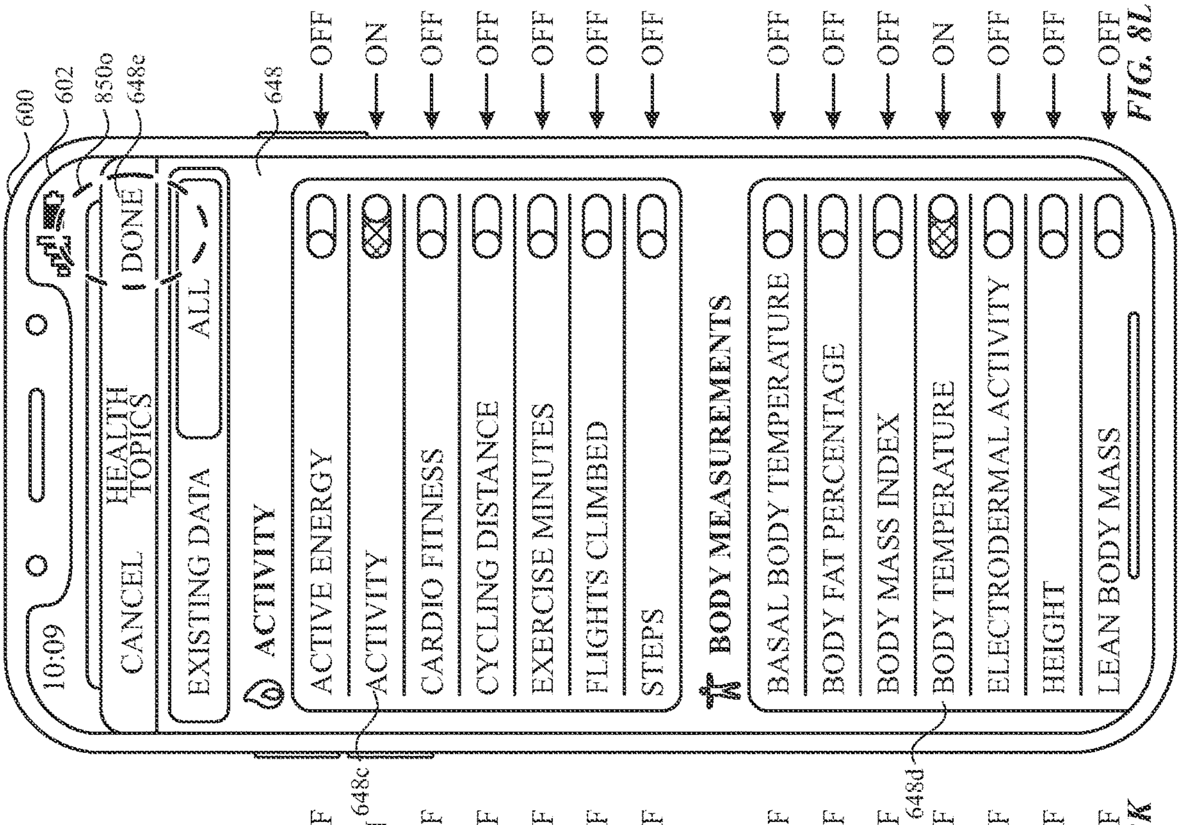
Figure 8K:
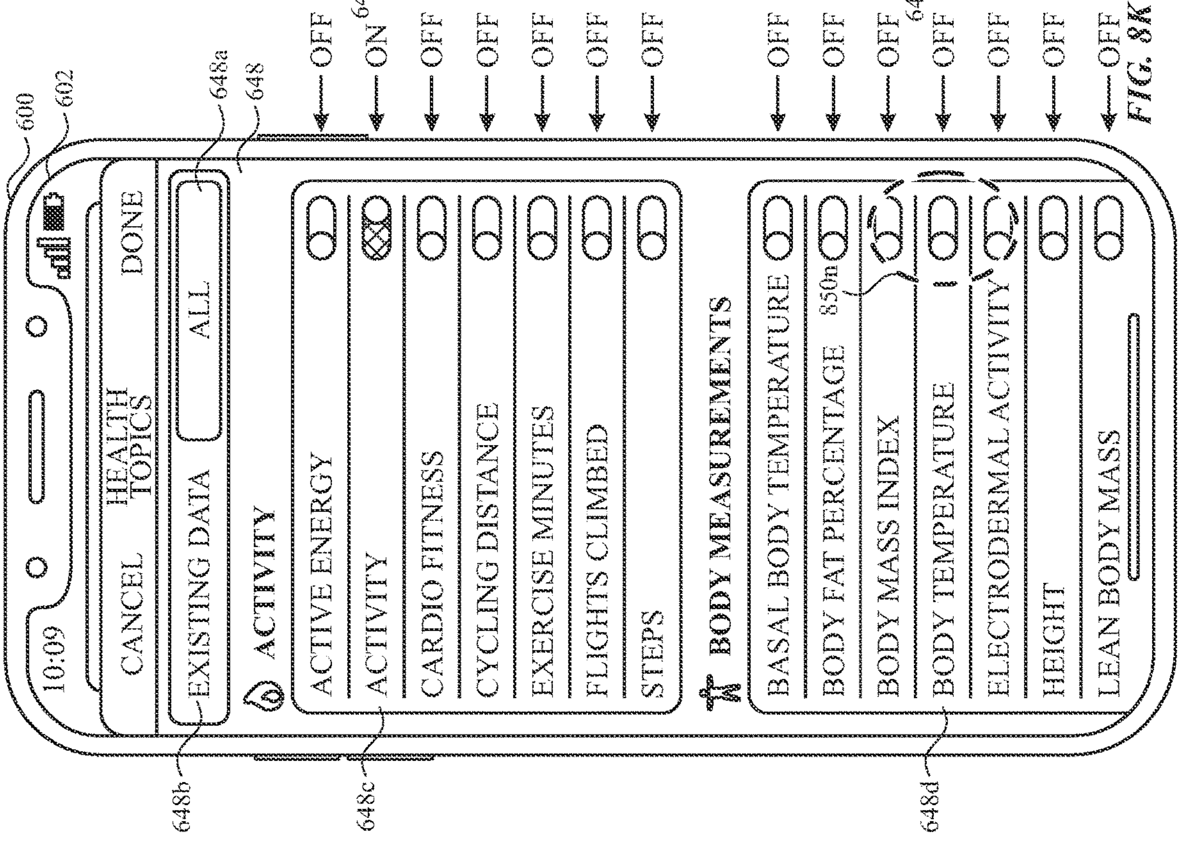
Figure 8N:
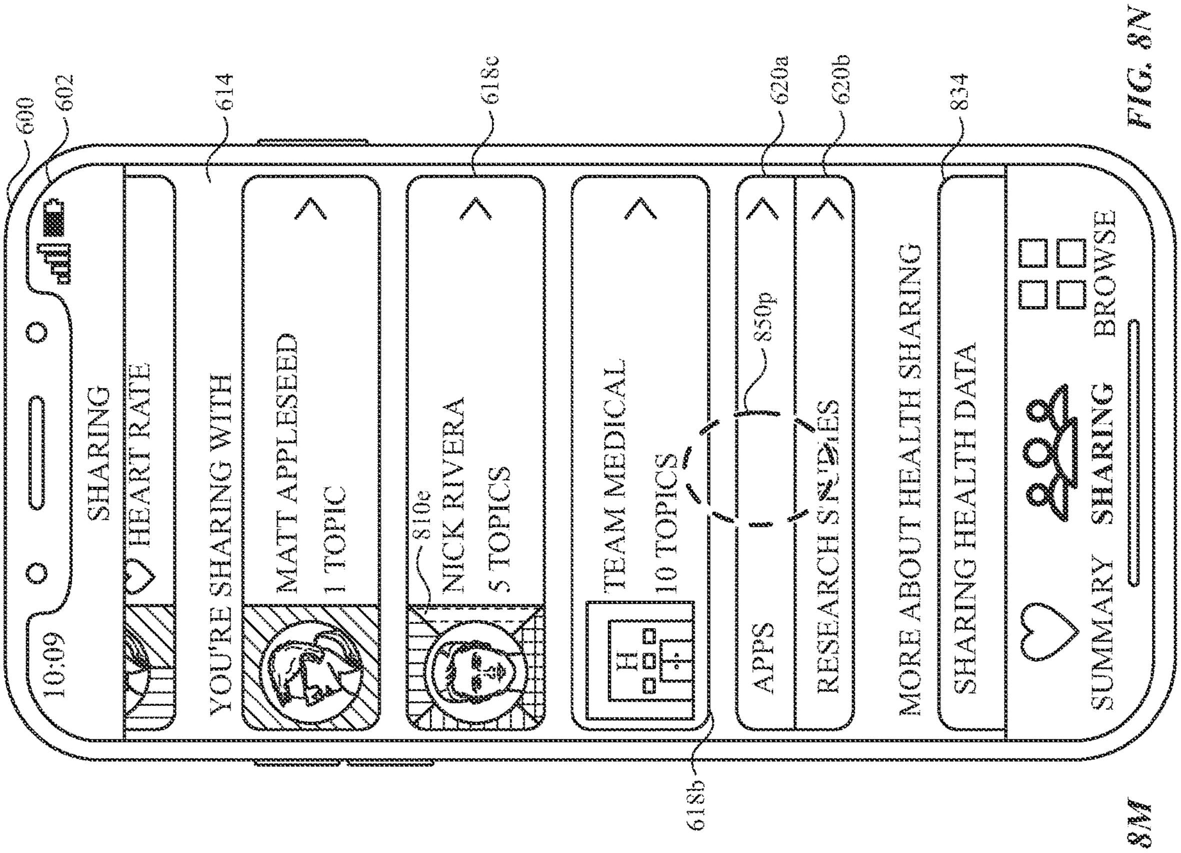

In FIG. 8H, device 600 detects tap input 850*h* corresponding to selection of fifth sharing affordance 618*c* for Nick Rivera and in response, displays sharing management user interface 830, as shown in FIG. 8I. In FIG. 8H, device 600 receives swipe input 850*i* and in response, scrolls health sharing user interface 614 to display additional portions of health sharing user interface 614, as shown in FIG. 8N. In FIG. 8H, device detects tap input 850*j* corresponding to selection of summary affordance 608 and in response, displays summary user interface 604, as shown in FIG. 8P.

In FIG. 8I, in response to receiving tap input 850*h*, device 600 displays sharing management user interface 830 for reviewing and modifying health data associated with the primary user account shared from device 600 to Nick Rivera, as indicated by user affordance 831 with Nick Rivera's contact photo and text indicating that health data has been shared for 90 days. Sharing management user interface 830 includes preview affordance 830*a* as well as stop affordance 830*b* that, when selected, causes device 600 to cease sharing of the set of health-related data shared from device 600 to Nick Rivera. Device 600 detects tap input 850*k* corresponding to selection of preview affordance 830*a* and in response, displays preview user interface 644, which will be discussed further with respect to FIG. 8J.

In FIG. 8I, sharing management user interface 830 includes first color 810*a*, second color 810*b*, third color 810*c*, and fourth color 810*d* (all represented by hatching) to indicate the overarching categories of the health topics shared with Nick Rivera. Sharing management user interface 830 further includes health topics section with affordances corresponding to the data types originally selected for sharing with Nick Rivera, as discussed in FIG. 6O. Activity affordance 830*c* indicates that the activity data is collected via watch (e.g., an external device in communication with device 600) and contains a removal affordance to remove activity from the health topics shared with Nick Rivera. Unlike activity affordance 830*c*, steps affordance 830*d* does not explicitly describe the device with which data is collected. In some embodiments, the absence of an indication of an external device for data collection of a particular health topic means that data for the health topic is collected by device 600. Sharing management user interface 830 further includes heart rate affordance 830*e* with a "WATCH ONLY" indication that indicates that data for the heart rate health topic is collected by, and only available with, an external smart watch. Activity affordance 830*c* includes a similar "WATCH ONLY" indication, while lab results affordance 830*f* and health alerts affordance 830*g* do not include the "WATCH ONLY" indication because the data related to lab results and health alerts can be collected by an external smart watch and/or other methods (e.g., manual entry from the user; collected via sensors of device 600; imported from other health and wellness applications; collected by devices configured to communicate with device 600).

Figure 8M:
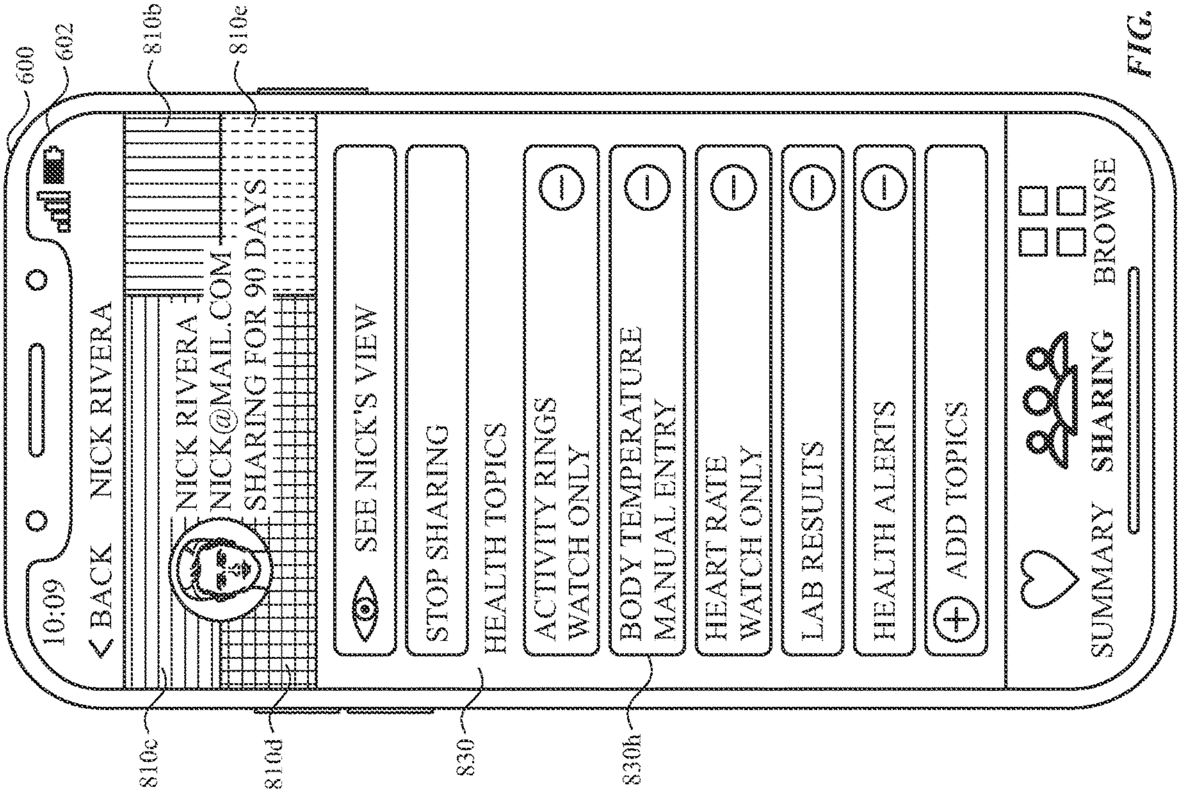
Figure 8P:
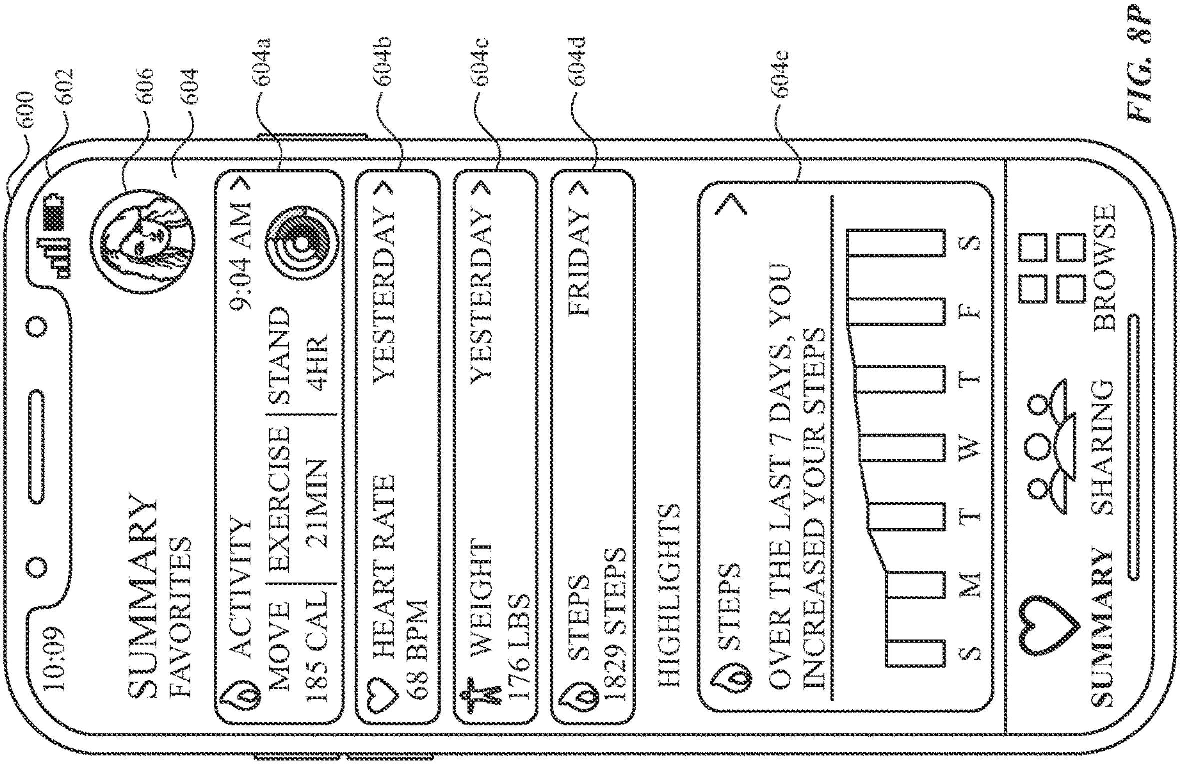

In FIG. 8I, device 600 detects tap input 850*l* corresponding to selection of the removal affordance within steps affordance 830*d* and in response, device 600 ceases sharing of health data relating to steps with Nick Rivera, as shown in FIG. 8M. Device 600 also detects tap input 850*m* corresponding to selection of add topics affordance 832 and in response, displays all topics user interface 648, as shown in FIG. 8K.

Turning now to FIG. 8J, in response to receiving tap input 850*k* corresponding to selection of preview affordance 830*a* in FIG. 8I, device 600 displays preview user interface 644. Preview user interface 644 is analogous to that described with respect to FIG. 6P and includes primary user affordance 606 to indicate that preview user interface 644 is showing Tiffany Smith's health data. Preview user interface 644 includes first color 810*a*, second color 810*b*, third color 810*c*, and fourth color 810*d* (all represented by hatching) to indicate the overarching categories of the health topics that Tiffany Smith (e.g., the primary user account of device 600) is sharing with Nick Rivera. The colors on preview user interface 644 have animated to be in a different arrangement than shown on sharing management user interface 830 of FIG. 8I.

In FIG. 8J, preview user interface 644 includes highlight affordance 604*e* before other health data affordances, such as activity affordance 604*a*. In some embodiments, highlight affordance 604*e* is shown after other health data affordances. In some embodiments, device 600 receives an input to scroll preview user interface 644 and in response, displays additional health data affordances corresponding to additional health topics shared with Nick Rivera. Highlight affordance 604*e* and activity affordance 604*a* are the same health data affordances shown on health summary user interface 604, which is discussed further with respect to FIG. 8P. In some embodiments, device 600 receives an input corresponding to the "DONE" affordance and in response, ceases display of preview user interface 644 and returns to displaying sharing management user interface 830 of FIG. 8I.

Turning now to FIG. 8K, device 600 displays all topics user interface 648 in response to tap input 850*m* corresponding to selection of add topics affordance 832 in FIG. 8I. All topics user interface 648 is analogous to that described with respect to FIG. 6T. All topics user interface 648 includes all affordance 648*a*, which is shown in an emphasized state (e.g., selected state), and existing data affordance 648*b*, which is shown in an inactive state. In some embodiments, device 600 receives an input corresponding to selection of existing data affordance 648*b* and in response, updates existing data affordance 648*b* to an emphasized state and displays a listing of health topics containing data entries corresponding to the user account of the primary user.

In FIG. 8K, all topics user interface 648 includes activity affordance 648*c* with the toggle shown in the "ON" position, indicating that activity is a data topic being shared by device 600. In some embodiments, device 600 detects a swipe input and in response, scrolls all topics user interface 648 to display additional data topic affordances, such as an affordance for heart rate having the toggle in the "ON" position. Device 600 detects tap input 850*n* corresponding to selection of the toggle within body temperature affordance 648*d*. In response to receiving tap input 850*n*, device 600 updates the toggle from the "OFF" position to the "ON" position, as shown in FIG. 8L.

In FIG. 8L, device 600 displays all topics user interface 648 with body temperature affordance 648*d* showing the toggle in the "ON" position, indicating that body temperature data entries are enabled for sharing with Nick Rivera from the primary user account of device 600. In some embodiments, device 600 receives an input corresponding to selection of the toggle within activity affordance 648*c* and in response, disables sharing of health data related to activity and updates the toggle to an "OFF" position. Device 600 detects tap input 650 corresponding to selection of done affordance 648*e* and in response, dismisses (e.g., ceases to display) all topics user interface 648.

In FIG. 8M, after dismissing all topics user interface 648, device 600 displays sharing management user interface 830 with an updated health topics section that includes body temperature affordance 830*h* and does not include steps affordance 830*d*, which was removed from the shared health topics in FIG. 8I. Body temperature affordance 830*h* includes notation that data entries for body temperature are manually entered into device 600. Sharing management user interface 830 now includes fifth color 810*e*, along with second color 810*b*, third color 810*c*, and fourth color 810*d* (all represented by hatching) to indicate the updated overarching categories of the health topics that Tiffany Smith (e.g., the primary user account of device 600) is now sharing with Nick Rivera. The colors 810*b*-810*e* have additionally animated to a new formation on sharing management user interface 830.

Turning now to FIG. 8N, device 600 displays health sharing user interface 614 in response to receiving swipe input 850*i* to scroll health sharing user interface 614 up in FIG. 8H. Fifth sharing affordance 618*c* for sharing health-related data with Nick Rivera is updated to include fifth color 810*e* (represented by hatching). Health sharing user interface 614 includes apps affordance 620*a* and research studies affordance 620*b*, analogous to that described with respect to FIG. 6B. Device 600 detects tap input 850*p* corresponding to selection of apps affordance 620*a* and in response, displays apps user interface 836 with applications that are receiving health-related data associated with the primary user account of device 600 in FIG. 8O. In some embodiments, device 600 detects an input corresponding to selection of research studies affordance 620*b* and in response, displays a user interface containing research studies that are receiving health-related data associated with the primary user account of device 600, similar to apps user interface 836 of FIG. 8O. In some embodiments, the primary user associated with device 600 previously enrolled in research studies and selected health-related data for sharing with the research studies. In some embodiments, device 600 detects an input corresponding to selection of info affordance 834 and in response, displays an informational user interface about sharing health-related data.

Figure 8O:
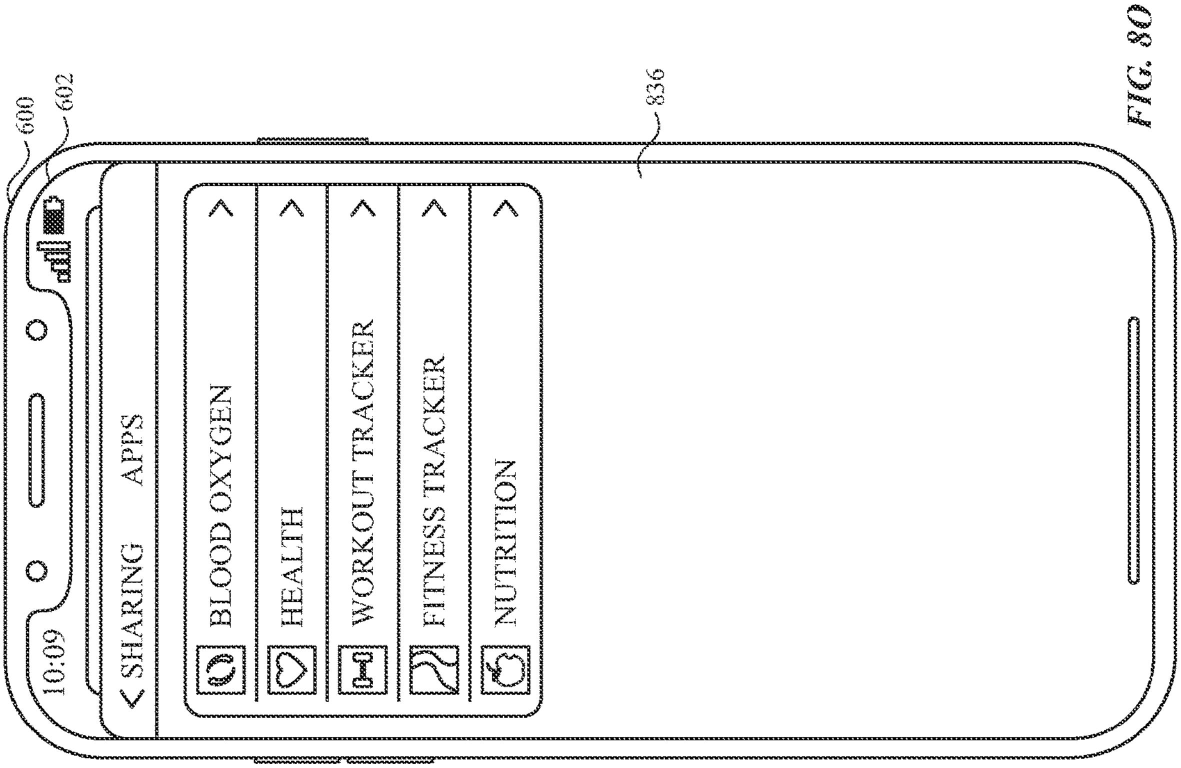

In FIG. 8O, device 600 displays apps user interface 836 with selectable application affordances corresponding to the applications receiving health data associated with the primary user account of device 600. In some embodiments, device 600 receives an input corresponding to selection of an application affordance and in response, displays an applications settings user interface for modifying the health data shared with the application.

Turning now to FIG. 8P, device 600 displays health summary user interface 604 in response to detecting tap input 850*j* corresponding to selection of summary affordance 608 FIG. 8H. Health summary user interface 604 includes primary user affordance 606, which indicates that the health data displayed on health summary user interface 604 is associated with the user account of the primary user of device 600 (e.g., Tiffany Smith). Activity affordance 604*a* and highlight affordance 604*e* shown on health summary user interface 604 are the same as those shown in preview user interface 644 for viewing Tiffany Smith's health topics being shared with Nick Rivera in FIG. 8J. Health summary user interface 604 includes additional health topic affordances (e.g., heart rate affordance 604*b*, weight affordance 604*c*, and steps affordance 604*d*) that are not shown in preview user interface 644 of FIG. 8J because these health topics are not included in the set of health-related data types selected for sharing with Nick Rivera.

FIG. 9 is a flow diagram illustrating method displaying user interfaces for shared health-related data using a computer system in accordance with some embodiments. Method 900 is performed at a computer system (e.g., 100, 300, 500, 600) (e.g., a smart phone, a smart watch) that is in communication with a display generation component (e.g., 112, 340, 504, 602) (e.g., a display controller, a touch-sensitive display system; and/or a display (e.g., integrated or connected)), wherein the computer system is associated with a first user account of a first user (e.g., belonging to the first user (e.g., that is associated with data pertaining to the first user)). In some embodiments, the computer system is only associated with a single user account for health data (e.g., a logged in account), at any given time. Some operations in method 900 are, optionally, combined, the orders of some operations are, optionally, changed, and some operations are, optionally, omitted.

As described below, method 900 provides an intuitive way for displaying user interfaces for shared health-related data. The method reduces the cognitive burden on a user for viewing shared health-related data, thereby creating a more efficient human-machine interface. For battery-operated computing devices, enabling a user to view shared health-related data faster and more efficiently conserves power and increases the time between battery charges.

The computer system (e.g., 600) displays (902), via the display generation component (e.g., 602), a health data sharing user interface (e.g., 614) that includes a plurality of selectable graphical user interface objects that include: a first selectable user interface object (904) (e.g., 616*b*) that corresponds to a second user account of a second user (e.g., GRANDMA APPLESEED of 616*b*) (e.g., different from the user of the computer system; the user of a second computer system) that is sharing a first set of health-related data (e.g., the data types 814*a*-814*h* shown on user interface 814) (e.g., medical and/laboratory data related to the health of a user; one or more types of data relating to health; health data specific to the second user; health data that does not include data for the first user) with the first user account (e.g., the user of the computer system); and a second selectable user interface object (906) (e.g., 618*c*) that corresponds to a third user account of a third user (e.g., NICK RIVERA of 618*c*) (e.g., different from the user of the computer system; the user of the second computer system; the user of a third computer system) that is receiving a second set of health-related data (e.g., the health topics listed on user interface 642; 830*c*-830*g* of FIG. 8I) (e.g., medical and/laboratory data related to the health of a user; one or more types of data relating to health; health data specific to the first user; health data that does not include data for the second and/or third user) from the first user account. In some embodiments, the second set of health-related data is different from the first set of health-related data. In some embodiments, the second user account and the third user account are the same. In some embodiments, the second user account and the third user account are different. In some embodiments, method 700 is used (e.g., at the computer system) to set up the health-related data sharing relationships for the second user account to the first user account and the first user account to the third user account. In some embodiments, displaying selectable user interface objects that correspond to accounts of users that are sharing health-related data with the computer system and/or receiving health-related data from the computer system provides the user with visual feedback for sharing statuses. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the health data sharing user interface (e.g., 614) includes: a fourth selectable user interface object (e.g., 616*a* of FIG. 8H) that corresponds to a fourth user account of fourth user (e.g., MATT APPLESEED of 616*a*) (e.g., different from the user of the computer system and the second user) that is sharing a third set of health-related data (e.g., as detailed by 818*a*, 818*b*, 818*c* of FIG. 8F) (e.g., medical and/laboratory data related to the health of a user; one or more types of data relating to health; health data specific to the second user; health data that does not include data for the first user) with the first user account (e.g., the user of the computer system). In some embodiments, displaying a selectable user interface object that corresponds to an account of a user that is sharing health-related data with the computer system provides the user with visual feedback of the account sharing with the user. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the health data sharing user interface (e.g., 614) includes: a fourth selectable user interface object (e.g. 618*a*) that corresponds to a fifth user account of a fifth user (e.g., MATT APPLESEED of 618*a*) (e.g., different from the user of the computer system and the third user) that is receiving a fourth set of health-related data (e.g., "1 TOPIC" as indicated by 618*a* of FIG. 8C) (e.g., medical and/laboratory data related to the health of a user; one or more types of data relating to health; health data specific to the first user; health data that does not include data for the second and/or third user) from the first user account. In some embodiments, method 700 is used (e.g., at the computer system) to set up the health-related data sharing relationships for the fifth user account. In some embodiments, displaying a selectable user interface object that corresponds to an accounts of a user that is receiving health-related data from the computer system provides the user with visual feedback of the account the user is sharing with. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the health data sharing user interface (e.g., 614) includes: in accordance with a determination that the first set of health-related data includes health-related notification data that satisfies a set of notification display criteria (e.g., the notification is recent, the notification is unread), a health-related notification indication (e.g., 812*a*, 812*b*) (e.g., a notification of a change in health status of the second user (e.g., health alert (e.g., low heart rate)) associated with the second user; in accordance with a determination that the first set of health-related data includes health-related data (e.g., laboratory results data; physiological data) that satisfies a set of recency criteria (e.g., the data was generated within a predetermining period of time (e.g., 1 day, 1 week, 1 month), the data was received after the health data sharing user interface was last displayed), a recent health-data indication (e.g., 812*c*) (e.g., a graphical object that presents the new data) associated with the second user; and in accordance with a determination that the first set of health-related data includes health-related data (e.g., laboratory results data; physiological data) that satisfies a set of change criteria (e.g., the data corresponds to a change to an existing health-related value (e.g., a physiological parameter (e.g., weight, blood glucose level, blood pressure; additional exercise (e.g., calories burned, steps taken)), a changed health-data indication (e.g., 812*d*, 812*e*) (e.g., a graphical object that presents the changed data (in some embodiments, that includes a comparison to the previous value for the data (e.g., a trend comparison that compares a value of the data for a first period of time to the value of the data for a second period of time)) associated with the second user. In some embodiments, displaying health-related notification indications provides the user with feedback as to whether health-related data being shared by another user satisfies a set of criteria. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system receives a set of one or more inputs (e.g., including an input at 806*a* in FIG. 8B and/or 8D to display an options user interface; 850*g* in FIG. 8G) (in some embodiments, the set of one or more inputs includes at least one input received while displaying a configuration user interface); in response to receiving the set of one or more input inputs, the computer system modifies (e.g., enabling or disabling) the display configuration (e.g., a configuration that controls whether indications of the indication type are displayed or not) of an indication type selected from the group consisting of: an indication type that corresponds to the health-related notification indication (e.g., 812*a*, 812*b*), an indication type that corresponds to the recent health-data indication (e.g., 802*a*), and an indication type that corresponds to the changed health-data indication (e.g., 812*c*, 812*d*, 812*e*). In some embodiments, modifying display configuration of indication types via a set of one or more inputs provides the user with additional controls for enhancing visual feedback. Providing additional control of the content displayed enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the indications are organized by the indication type and/or the recency of the data related to the indication.

In some embodiments, indications included in the health data sharing user interface are organized by the type of indication (e.g., 812*a* and 812*b* shown at the top of 616*b* in FIG. 8H) (e.g., any health-related notification indications first, then any recent health-data indications, then any changed health-data indications). In some embodiments, indications can occupy no more than a predetermined maximum amount (e.g., lines, area) of the user interface.

In some embodiments, a first indication (e.g., 812*d*, 812*c*) (e.g., a single, first indication) is indicative of a plurality of instances of data that satisfied the set of notification display criteria, the set of recency criteria, and/or the set of changed health-data indication. In some embodiments, after a maximum number of discrete (e.g., 1-to-1 indications) indications are displayed, additional data that satisfies the criteria are grouped into a single indication (e.g., a single indication of "10 other updates"). In some embodiments, providing an indication that is indicative of a plurality of instances of data that satisfy a set of criteria reduces the amount of indications provided to the user, thereby decluttering the user interface. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of change criteria includes a criterion that is satisfied when the first set of health-related data (e.g., steps data corresponding to 812*d*; heart rate data corresponding to 812*e*; steps data corresponding to 604*e*) includes data that indicates that a first health-related parameter (e.g., a health-related measurement or value (e.g., heart rate, calories burned, blood glucose level, body weight) experienced a threshold amount of change (e.g., the difference in the height of the bars between Sunday and Saturday in 604*e*) (e.g., decreased or increased (e.g., on average, in the aggregate, on a recurring basis (e.g., each day for a period of days)) by a minimum amount) for at least a threshold amount of time (e.g., "7 DAYS" as in 604*e*) (e.g., 5 days, a week, a month, six months, a year). In some embodiments, the health data sharing user interface includes a trend indication that shows significant changes in a health-related parameter for a user sharing their data with the user of the computer system. In some embodiments, providing indications for data that meet a threshold criteria provides the user with feedback as to the portions of health-data that are potentially significant, without cluttering the user interface with data that does not meet the threshold criteria. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, when the first set of health-related data includes data that indicates that a health-related parameter experienced a threshold amount of change, an indication was also provided to the second user at an external computer system associated with the second user.

In some embodiments, the set of change criteria includes a criterion that is satisfied when the average value (in some embodiments, the median value, the mode value, a noise-corrected mean value) for a second health-related parameter for a first time period (e.g., "THE LAST 7 DAYS" as in 604*e*) in the first set of health-related data has a difference from the average value for the second health-related parameter for a second time period (e.g., the 7 days prior to "THE LAST 7 DAYS" as in 604*e*) (e.g., a time period of the same length as the first time period, a time period that is different in length from the first time period, a time period that is consecutive with the first time period (e.g., immediately before or after), a time period that, together with the first time period, equals a predetermined length/time window (e.g., a 4 week time window (or a 26 week time window) wherein the first and second time periods are sub-portions of the time window that add up, together, to the whole window) that is greater than a first predetermined amount of difference (e.g., a clinically and/or empirically determined value that is significant (e.g., clinically significant)). In some embodiments, if a user experiences a significant change between a first sub-period (e.g., a pre-period) and a second sub-period (e.g., a post-period) of a predetermined time window (e.g., a 4 week window, a 26 week window) changed health-data indication can be issued/provided. In some embodiments, the pre- and post-periods are determined based on the most significant single change (e.g., most significant one day change) in the predetermined time window. In some embodiments, providing indications for data that meet an average value criterion provides the user with feedback as to the portions of health-data that are potentially significant, without cluttering the user interface with data that does not meet the average value criterion. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, a difference of the average value between the first and second time periods that is less than the first determined amount of difference but is greater than a second amount of difference satisfies a criterion of the set of change criteria if (e.g., when, in accordance with a determination) the difference of the average value between the first and second time periods, for a third health-related parameter (e.g., a different parameter that is clinically correlated to the second health-related parameter (e.g., calories burned in a day and number of steps taken in the day), is greater than the first determined amount of difference. Thus, in some embodiments, a more "relaxed" difference/change notification threshold can result in a change notification for a given health-related parameter if a correlated health-related parameter met the "unrelaxed" threshold. In some embodiments, notifications based on the relaxed threshold being met for a health-related parameter also indicate the correlated health-related parameter that satisfied the "unrelaxed" threshold.

In some embodiments, the first selectable user interface object (e.g., 616*b*) has a first visual characteristic (e.g., colors represented by hatching 810*a*-810*e*) (e.g., a color and/or color pattern of the object, a shape of the object, a size of the object) that: in accordance with a determination that a first set of visual characteristic display criteria are satisfied, wherein the first set of visual characteristic display criteria includes a criterion that is satisfied when the first set of health-related data includes a first data type (e.g., 814*d*) (e.g., physical activity data, heart-related data, blood glucose data), the first visual characteristic includes a first value (e.g., a particular color (e.g., red, blue, green) or pattern of colors (red with blue, green with orange)) of the first visual characteristic. In some embodiments, in accordance with a determination that the first set of health-related data does not include the first data type, the first visual characteristic does not include the first value of the first visual characteristic. In some embodiments, the first selectable user interface object (e.g., 616*b*) has a first visual characteristic (e.g., colors represented by hatching 810*a*-810*e*) (e.g., a color and/or color pattern of the object, a shape of the object, a size of the object) that: in accordance with a determination that a second set of visual characteristic display criteria are satisfied, wherein the second set of visual characteristic display criteria includes a criterion that is satisfied when the first set of health-related data includes a second data type (e.g., 814*a*, 814*f*) (e.g., different than the first data type), the first visual characteristic includes a second value (e.g., 810*b*) (e.g., a particular color (e.g., red, blue, green) or pattern of colors (red with blue, green with orange)) of the first visual characteristic. In some embodiments, displaying selectable user interface objects that have visual characteristics based on the set of health-related data provides the user with feedback regarding the data types included in the set of health-related data. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set (in some embodiments, also the second set) of visual characteristic display criteria includes a criterion that is met when the first visual characteristic does not include (e.g., already include) more than a predetermined number (e.g., 3, 4, 5, 6) of other values (e.g., other colors) of the first visual characteristic (e.g., 4 colors indicated by 810*a*-810*d* of 616*b*; 4 colors indicated by 810*b*-810*e* in FIG. 8M). In some embodiments, the second user interface object can include a predetermined maximum number of values for a characteristic (e.g., no more than 4 colors that each correspond to a type of data that is being shared).

In some embodiments, the first visual characteristic includes the predetermined number of values of the first visual characteristic (e.g., 4 colors indicated by 810*a*-810*d* of 616*b*; 4 colors indicated by 810*b*-810*e* in FIG. 8M) and the included values of the first visual characteristic correspond to the most frequently used (e.g., most frequently selected for sharing, most frequently collected/available) data types in the second set of health-related data. In some embodiments, limiting the values of the first visual characteristic provides the user with feedback regarding the data types included in the set of health-related data that are potentially significant, without cluttering the display with additional visual characteristic values. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first visual characteristic of the first selectable user interface object includes the first value and the second value of the first visual characteristic (e.g., 4 colors indicated by 810*a*-810*d* of 616*b;* 4 colors indicated by 810*b*-810*e* in FIG. 8M). In some embodiments, the computer system animates, over time, display of the first visual characteristic of the first selectable user interface object through at least a first visual state and a second visual state (e.g., the change in position of 810*a*-810*d* in FIG. 8I to FIG. 8J). In some embodiments, the first selectable user interface object and a fifth selectable user interface object, which corresponds to a sixth user account of sixth user that is sharing health-related data, has a second visual characteristic that includes the same values (e.g., the first and second values) of that visual characteristic as included in the first visual characteristic of the first selectable user interface object (e.g., both the first and fifth selectable user interface objects include the same pattern of colors), wherein the objects are animated such that the visual states do not align at least one point in time (e.g., while the objects have the same pattern of colors, the patterns are animated through states asynchronously so that objects are visually distinguishable). In some embodiments, animating the display of the visual characteristics for a selectable user interface object provides the user with feedback regarding the data types included in the set of health-related data, while being visually distinguishable from another set of health-related data. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system receives, from an external computer system (e.g., the computer system associated with MATT APPLESEED in 616*a*), data indicating that a sixth user is requesting to share a fifth set of health-related data (e.g., 818*a*-818*c*) with the first user, and in response to receiving the data indicating that the sixth user is requesting to share the fifth set of health-related data with the first user, the computer system displays a notification (e.g., 616*a* FIG. 8C) indicating the sixth user is requesting to share a fifth set of health-related data with the first user. In some embodiments, the notification includes a selectable user interface object that, when selected, initiates a process for accepting the sixth user's request to share. In some embodiments, displaying a notification indicating another user is requesting to share a set of health-related data provides the user with visual feedback about the sharing status of the other user. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system accepts the request (in some embodiments, based on a set of inputs that includes an input received while the notification is displayed) to share the fifth set of health-related data with the first user (e.g., via input 850*d* at 616*aa* and input 850*f* at 818*d*), wherein accepting the request includes enabling (e.g., approving) one or more subsequent notifications (e.g., via input 850*g* at 826) corresponding to the fifth set of health-related data (e.g., future health-related notifications associated with the sixth user). In some embodiments, enabling one or more notifications corresponding to a set of health-related data provides the user with visual feedback regarding health-related data from another user that is potentially significant. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after accepting the request, the computer system displays an option to enable sharing of the first user's health-related data with the sixth user, similar to as described in method 700.

In some embodiments, the computer system receives a first set of one or more user inputs (e.g., 850*c*) that includes an input corresponding to the first selectable user interface object (e.g., 616*b*), and in response to receiving the first set of one or more user inputs, the computer system displays, via the display generation component (e.g., 602), a shared health data user interface (e.g., 814) that corresponds to the first set of health-related data and that includes: a first set of one or more user interface objects (e.g., 814*a*-814*g*) that represent the first set of health-related data (e.g., views of the health data of the second user); and a second set of one or more user interface objects that represent previously received notifications based on the first set of health-related data (e.g., 814*h*) (e.g., a history of health-related alerts relating to the second user). In some embodiments, displaying a shared health data user interface that includes user interface objects that represent the set of shared health-related data provides the user with visual feedback regarding data types being shared by another user. Displaying the shared health data user interface that includes user interface objects that represent previously received notifications relating to the set of shared health-related data provides the user with visual feedback regarding historic health-related data shared by another user that was potentially significant. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the shared health data user interface (e.g., 814) that corresponds to the second user (e.g., GRANDMA APPLESEED as shown on 814 of FIG. 8D) includes a contact selectable user interface object (e.g.,

816*a*-816*d*) that, when selected, initiates a process for contacting (e.g., by phone, by text, by email) the second user. In some embodiments, providing a selectable user interface object that initiates a process for contacting on the shared health data user interface minimizes the number of inputs required to contact the other user. Reducing the number of inputs needed to perform an operation the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system receives a second set of one or more user inputs that includes an input (e.g., 850*h*) corresponding to the second selectable user interface object (e.g., 618*c*), and in response to receiving the second set of one or more user inputs, the computer system displays, via the display generation component (e.g., 602), a sharing health data user interface (e.g., 830) that corresponds to the second set of health-related data (e.g., 830*c*-830*g*) from the first user account.

In some embodiments, the sharing health data user interface (e.g., 830) includes a sharing preview selectable user interface object (e.g., 830*a*) that, when selected (e.g., by input 850*k*), provides a preview (e.g., 644) of the second set of health-related data that is being shared with the third user. In some embodiments, the preview is visually formatted in a manner that is similar to how the second set of health-related data would be presented to the third user on a computer system of the third user. In some embodiments, displaying a preview of the set of health-related data that is being shared with another user provides the user with visual feedback regarding the display of their health-related data from the other user's perspective. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the preview of the second set of health-related data includes at least a plurality of graphical objects representing the data in the second set of health-related data (e.g., 604*e*, 604*a* in FIG. 8J).

In some embodiments, the sharing health data user interface (e.g., 830) includes a modification selectable user interface object (e.g., 832) that, when selected, initiates a process for modifying (e.g., adding, removing) the data included in the second set of health-related data (e.g., as shown by the change in toggle position of 648*c* and 648*d* in FIGS. 8K-8L) (e.g., modifying the types of data that are included in the second set of health-related data). In some embodiments, providing a selectable user interface object for modifying the data included in the shared set of health-related data provides the user more control of the computer system and data being shared. Providing additional control options enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the health data sharing user interface (e.g., 614) includes an indication (e.g., 620*a*, 618*b*) of an application (e.g., an application installed on the computer system; an application corresponding to a medical provider group) that is receiving a sixth set of health-related data from the first user account (e.g., from the first user). In some embodiments, the health data sharing user interface includes an indication of one or more research studies that are receiving health-related data from the first user account. In some embodiments, displaying an indication of an application that is receiving health-related data from the computer system provides the user with visual indication of the sharing status of their health-related data. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 900 (e.g., FIG. 9) are also applicable in an analogous manner to the methods described above. For example, method 700 optionally includes one or more of the characteristics of the various methods described above with reference to method 900. For example, the selectable user interface objects of method 900 are displayed after initiating sharing of health-related data via method 700. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve management of health-related data. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to monitor conditions related to health and general wellness. Accordingly, use of such personal information enables users to view and understand their own health-related data over time, as well as health-related data permitted for sharing by other users in accordance with the methods described above. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of managing health-related data, the present technology can be configured to allow users to select to "opt in" or "opt out" of participation in the collection of personal information data during registration for services or anytime thereafter. In another example, users can select not to provide health-related data to other selected users and/or medical institutions. In yet another example, users can select to limit the length of time health-related data is maintained or entirely prohibit the development of a baseline health profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, health-related features can be surfaced to users by inferring preferences based on non-personal information data or a bare minimum amount of personal information, such as the content being requested by the device associated with a user, other non-personal information available to the computer system, or publicly available information.

What is claimed is:

1. A computer system configured to communicate with a display generation component, a plurality of sensors for collecting health-related data including a first sensor for collecting a first type of health-related data and a second sensor for collecting a second type of health-related data, and one or more input devices, comprising:

one or more processors; and memory storing one or more programs configured to be executed by the one or more processors, the one or more programs including instructions for:

receiving, via the one or more input devices, a first set of one or more inputs that correspond to a request to initiate a process for sharing a set of health-related data;

in response to receiving the first set of one or more inputs:

displaying, via the display generation component, a first data selection user interface that includes:

in accordance with a determination that a first data type satisfies a first set of criteria, wherein the first set of criteria includes a criterion that is satisfied based on a frequency of user interaction with the first data type, a first selectable user interface object that corresponds to the first data type and that, when selected, modifies a sharing status of the first data type in the process for sharing the set of health-related data; and in accordance with a determination that a second data type satisfies a second set of criteria, a second selectable user interface object that corresponds to the second data type and that, when selected, modifies the sharing status of the second data type in the process for sharing the set of health-related data;

during the process for sharing the set of health-related data and before completing the process for sharing the set of health-related data, displaying a second data selection user interface that includes a third selectable user interface object that, when selected, modifies the sharing status for health-related notifications of a first type of health event that are provided at the computer system, wherein the computer system is enabled to output the health-related notifications of the first type of health event after detecting health events corresponding to the first type of health event;

receiving a second set of one or more inputs that includes an input corresponding to the third selectable user interface object;

in response to receiving the second set of one or more inputs, enabling the computer system to share statuses for health-related notifications of the first type of health event;

after completing the process for sharing the set of health-related data, detecting, via the first sensor and/or the second sensor of the plurality of sensors for collecting health-related data, the first type of health event; and in response to detecting the first type of health event:

outputting a first health-related notification corresponding to the first type of health event; and sharing a status of the first health-related notification with one or more external devices.

2. The computer system of claim 1, wherein the first set of criteria includes a criterion that is satisfied when the first data type includes user data that was created or modified within a predetermined time period.

3. The computer system of claim 1, the one or more programs further including instructions for:

while displaying the first selectable user interface object and/or displaying the second selectable user interface object, receiving a third set of one or more inputs;

in response to receiving the third set of one or more inputs:

completing the process for sharing the set of health-related data; and sharing the set of health-related data with at least one external computer system, wherein:

in accordance with a determination that the second set of one or more inputs includes a first input that corresponds to selection of the first selectable user interface object that corresponds to the first data type, the set of health-related data that is shared includes shared data of the first data type; and in accordance with a determination that the second set of one or more inputs includes a second input that corresponds to selection of the second selectable user interface object that corresponds to the second data type, the set of health-related data that is shared includes shared data of the second data type.

4. The computer system of claim 1, wherein:

the first data type is selected from the group consisting of: user-entered data, data collected by one or more sensors that are in communication with the computer system, data transmitted by one or more external devices, and a combination thereof.

5. The computer system of claim 1, wherein the first data type and the second data type satisfy a first set of grouping criteria, the one or more programs further including instructions:

after displaying the first data selection user interface, displaying a second user selection user interface that includes:

a fourth selectable user interface object that corresponds to a third data type and that, when selected, modifies the sharing status of the third data type in the process for sharing the set of health-related data, wherein the third data type satisfies a second set of grouping criteria but does not satisfy the first set of grouping criteria; and a fifth selectable user interface object that corresponds to a fourth data type and that, when selected, modifies the sharing status of the fourth data type in the process for sharing the set of health-related data, wherein the fourth data type satisfies the second set of grouping criteria but does not satisfy the first set of grouping criteria.

6. The computer system of claim 5, the one or more programs further including instructions for:

prior to displaying the first data selection user interface, displaying a sixth selectable user interface object;

receiving a fourth set of one or more user inputs that includes an input corresponding to the sixth selectable user interface object; and in response to receiving the fourth set of one or more user inputs, displaying a third data selection user interface that includes:

a seventh selectable user interface object that corresponds to the first data type and that, when selected, modifies the sharing status of the first data type in the process for sharing the set of health-related data; and an eighth selectable user interface object that corresponds to the third data type and that, when selected, modifies the sharing status of the third data type in the process for sharing the set of health-related data.

7. The computer system of claim 5, wherein the first data selection user interface includes an ninth selectable user interface object, the one or more programs further including instructions for:

receiving a user input corresponding to the ninth selectable user interface object; and in response to receiving the user input corresponding to the ninth selectable user interface object:

displaying a tenth selectable user interface object that corresponds to a fifth data type and that, when selected, modifies the sharing status of the fifth data type in the process for sharing the set of health-related data, wherein:

the fifth data type satisfies the first set of grouping criteria; and the fifth data type does not satisfy the first set of criteria.

8. The computer system of claim 1, wherein the first selectable user interface object and the second selectable user interface object are independently selectable to modify the sharing status of the respective data type.

9. The computer system of claim 1, the one or more programs further including instructions for:

after displaying the first data selection user interface and before completing the process for sharing the set of health-related data, displaying a third data selection user interface that includes:

a first laboratory results selectable user interface object that corresponds to a first laboratory results data type and that, when selected, modifies the sharing status of the first laboratory results data type in the process for sharing the set of health-related data; and a second laboratory results selectable user interface object that corresponds to a second laboratory results data type and that, when selected, modifies the sharing status of the second laboratory results data type in the process for sharing the set of health-related data.

10. The computer system of claim 9, wherein the first laboratory results selectable user interface object and the second laboratory results selectable user interface object are independently selectable to modify the sharing status of the respective type of laboratory results data.

11. The computer system of claim 9, wherein the third data selection user interface includes a eleventh selectable user interface object, the one or more programs further including instructions for:

receiving a user input corresponding to selection of the eleventh selectable user interface object; and in response to the user input corresponding to selection of the eleventh selectable user interface object, displaying a confirmation user interface that includes a confirmation selectable user interface object that, when selected, modifies the sharing status for all laboratory results data types.

12. The computer system of claim 1, the one or more programs further including instructions for:

prior to displaying the first data selection user interface, displaying a contact selection user interface that includes:

a first contactable user selectable user interface object that satisfies a set of contact grouping criteria and that, when selected, designates a first contactable user as a recipient for the set of health-related data; and a second contactable user selectable user interface object that satisfies the set of contact grouping criteria and that, when selected, designates a second contactable user as a recipient for the set of health-related data.

13. The computer system of claim 12, wherein:

the process for sharing the set of health-related data includes designating a single contactable user to receive the set of health-related data; and both the first contactable user and the second contactable user cannot be, via the contact selection user interface, concurrently designated as recipients for the set of health-related data.

14. The computer system of claim 1, the one or more programs further including instructions for:

prior to completing the process for sharing the set of health-related data, displaying a summary user interface, wherein the summary user interface includes indications of the data types that have been selected to be included in the set of health-related data for sharing upon completion of the process for sharing the set of health-related data.

15. The computer system of claim 14, wherein the summary user interface includes an eleventh selectable user interface object, the one or more programs further including instructions for:

receiving an input corresponding to the eleventh selectable user interface object; and in response receiving the input corresponding to the eleventh selectable user interface object, displaying a preview user interface, wherein the preview user interface includes a graphical preview of the set of health-related data as it would be presented to a designated recipient of the set of health-related data after completion of the process for sharing the set of health-related data.

16. The computer system of claim 14, wherein the summary user interface includes a twelfth selectable user interface object that when selected, enables modification of the data types that have been selected to be included in the set of health-related data for sharing upon completion of the process for sharing the set of health-related data.

17. The computer system of claim 1, the one or more programs further including instructions for:

during the process for sharing the set of health-related data or after completion of the process for sharing the set of health-related data, displaying a thirteenth user selectable user interface object that, when selected, initiates a process to request health-related data from a second designated recipient of the set of health-related data.

18. The computer system of claim 1, the one or more programs further including instructions for:

completing the process for sharing the set of health-related data, wherein the process for sharing the set of health-related data causes a first set of health-related data to be shared with a third designated recipient; and completing a second process for sharing a second set of health-related data, wherein:

the second process for sharing the second set of health-related data causes the second set of health-related data to be shared with a fourth designated recipient; and the first set of health-related data includes different data types than those includes in the second set of health-related data.

19. A non-transitory computer-readable storage medium storing one or more programs configured to be executed by one or more processors of a computer system that is in communication with a display generation component, a plurality of sensors for collecting health-related data including a first sensor for collecting a first type of health-related data and a second sensor for collecting a second type of health-related data, and one or more input devices, the one or more programs including instructions for:

receiving, via the one or more input devices, a first set of one or more inputs that correspond to a request to initiate a process for sharing a set of health-related data;

in response to receiving the first set of one or more inputs:

displaying, via the display generation component, a first data selection user interface that includes:

in accordance with a determination that a first data type satisfies a first set of criteria, wherein the first set of criteria includes a criterion that is satisfied based on a frequency of user interaction with the first data type, a first selectable user interface object that corresponds to the first data type and that, when selected, modifies a sharing status of the first data type in the process for sharing the set of health-related data; and in accordance with a determination that a second data type satisfies a second set of criteria, a second selectable user interface object that corresponds to the second data type and that, when selected, modifies the sharing status of the second data type in the process for sharing the set of health-related data;

during the process for sharing the set of health-related data and before completing the process for sharing the set of health-related data, displaying a second data selection user interface that includes a third selectable user interface object that, when selected, modifies the sharing status for health-related notifications of a first type of health event that are provided at the computer system, wherein the computer system is enabled to output the health-related notifications of the first type of health event after detecting health events corresponding to the first type of health event;

in response to receiving the second set of one or more inputs, enabling the computer system to share statuses for health-related notifications of the first type of health event;

after completing the process for sharing the set of health-related data, detecting, via the first sensor and/or the second sensor of the plurality of sensors for collecting health-related data, the first type of health event; and in response to detecting the first type of health event:

outputting a first health-related notification corresponding to the first type of health event; and sharing a status of the first health-related notification with one or more external devices.

20. A method, comprising:

at a computer system that is in communication with a display generation component, a plurality of sensors for collecting health-related data including a first sensor for collecting a first type of health-related data and a second sensor for collecting a second type of health-related data, and one or more input devices:

receiving, via the one or more input devices, a first set of one or more inputs that correspond to a request to initiate a process for sharing a set of health-related data;

in response to receiving the first set of one or more inputs:

displaying, via the display generation component, a first data selection user interface that includes:

in accordance with a determination that a first data type satisfies a first set of criteria, wherein the first set of criteria includes a criterion that is satisfied based on a frequency of user interaction with the first data type, a first selectable user interface object that corresponds to the first data type and that, when selected, modifies a sharing status of the first data type in the process for sharing the set of health-related data; and in accordance with a determination that a second data type satisfies a second set of criteria, a second selectable user interface object that corresponds to the second data type and that, when selected, modifies the sharing status of the second data type in the process for sharing the set of health-related data;

during the process for sharing the set of health-related data and before completing the process for sharing the set of health-related data, displaying a second data selection user interface that includes a third selectable user interface object that, when selected, modifies the sharing status for health-related notifications of a first type of health event that are provided at the computer system, wherein the computer system is enabled to output the health-related notifications of the first type of health event after detecting health events corresponding to the first type of health event;

receiving a second set of one or more inputs that includes an input corresponding to the third selectable user interface object;

after completing the process for sharing the set of health-related data, detecting, via the first sensor and/or the second sensor of the plurality of sensors for collecting health-related data, the first type of health event; and in response to detecting the first type of health event:

outputting a first health-related notification corresponding to the first type of health event; and sharing a status of the first health-related notification with one or more external devices.

21. The computer system of claim 1, wherein the first data type corresponds to a first health-related measurement and the second data type corresponds to a second health-related measurement.

22. The non-transitory computer-readable storage medium of claim 19, wherein the first set of criteria includes a criterion that is satisfied when the first data type includes user data that was created or modified within a predetermined time period.

23. The non-transitory computer-readable storage medium of claim 19, the one or more programs further including instructions for:

while displaying the first selectable user interface object and/or displaying the second selectable user interface object, receiving a third set of one or more inputs;

in response to receiving the third set of one or more inputs:

completing the process for sharing the set of health-related data; and sharing the set of health-related data with at least one external computer system, wherein:

in accordance with a determination that the second set of one or more inputs includes a first input that corresponds to selection of the first selectable user interface object that corresponds to the first data type, the set of health-related data that is shared includes shared data of the first data type; and in accordance with a determination that the second set of one or more inputs includes a second input that corresponds to selection of the second selectable user interface object that corresponds to the second data type, the set of health-related data that is shared includes shared data of the second data type.

24. The non-transitory computer-readable storage medium of claim 19, wherein:

the first data type is selected from the group consisting of: user-entered data, data collected by one or more sensors that are in communication with the computer system, data transmitted by one or more external devices, and a combination thereof.

25. The non-transitory computer-readable storage medium of claim 19, wherein the first data type and the second data type satisfy a first set of grouping criteria, the one or more programs further including instructions:

after displaying the first data selection user interface, displaying a second user selection user interface that includes:

a fourth selectable user interface object that corresponds to a third data type and that, when selected, modifies the sharing status of the third data type in the process for sharing the set of health-related data, wherein the third data type satisfies a second set of grouping criteria but does not satisfy the first set of grouping criteria; and a fifth selectable user interface object that corresponds to a fourth data type and that, when selected, modifies the sharing status of the fourth data type in the process for sharing the set of health-related data, wherein the fourth data type satisfies the second set of grouping criteria but does not satisfy the first set of grouping criteria.

26. The non-transitory computer-readable storage medium of claim 25, the one or more programs further including instructions for:
prior to displaying the first data selection user interface, displaying a sixth selectable user interface object;
receiving a fourth set of one or more user inputs that includes an input corresponding to the sixth selectable user interface object; and
in response to receiving the fourth set of one or more user inputs, displaying a third data selection user interface that includes:
a seventh selectable user interface object that corresponds to the first data type and that, when selected, modifies the sharing status of the first data type in the process for sharing the set of health-related data; and
an eighth selectable user interface object that corresponds to the third data type and that, when selected, modifies the sharing status of the third data type in the process for sharing the set of health-related data.

27. The non-transitory computer-readable storage medium of claim 25, wherein the first data selection user interface includes an ninth selectable user interface object, the one or more programs further including instructions for:
receiving a user input corresponding to the ninth selectable user interface object; and
in response to receiving the user input corresponding to the ninth selectable user interface object:
displaying a tenth selectable user interface object that corresponds to a fifth data type and that, when selected, modifies the sharing status of the fifth data type in the process for sharing the set of health-related data, wherein:
the fifth data type satisfies the first set of grouping criteria; and
the fifth data type does not satisfy the first set of criteria.

28. The non-transitory computer-readable storage medium of claim 19, wherein the first selectable user interface object and the second selectable user interface object are independently selectable to modify the sharing status of the respective data type.

29. The non-transitory computer-readable storage medium of claim 19, the one or more programs further including instructions for:
after displaying the first data selection user interface and before completing the process for sharing the set of health-related data, displaying a third data selection user interface that includes:
a first laboratory results selectable user interface object that corresponds to a first laboratory results data type and that, when selected, modifies the sharing status of the first laboratory results data type in the process for sharing the set of health-related data; and
a second laboratory results selectable user interface object that corresponds to a second laboratory results data type and that, when selected, modifies the sharing status of the second laboratory results data type in the process for sharing the set of health-related data.

30. The non-transitory computer-readable storage medium of claim 29, wherein the first laboratory results selectable user interface object and the second laboratory results selectable user interface object are independently selectable to modify the sharing status of the respective type of laboratory results data.

31. The non-transitory computer-readable storage medium of claim 29, wherein the third data selection user interface includes a eleventh selectable user interface object, the one or more programs further including instructions for:
receiving a user input corresponding to selection of the eleventh selectable user interface object; and
in response to the user input corresponding to selection of the eleventh selectable user interface object, displaying a confirmation user interface that includes a confirmation selectable user interface object that, when selected, modifies the sharing status for all laboratory results data types.

32. The non-transitory computer-readable storage medium of claim 19, the one or more programs further including instructions for:
prior to displaying the first data selection user interface, displaying a contact selection user interface that includes:
a first contactable user selectable user interface object that satisfies a set of contact grouping criteria and that, when selected, designates a first contactable user as a recipient for the set of health-related data; and
a second contactable user selectable user interface object that satisfies the set of contact grouping criteria and that, when selected, designates a second contactable user as a recipient for the set of health-related data.

33. The non-transitory computer-readable storage medium of claim 32, wherein:
the process for sharing the set of health-related data includes designating a single contactable user to receive the set of health-related data; and
both the first contactable user and the second contactable user cannot be, via the contact selection user interface, concurrently designated as recipients for the set of health-related data.

34. The non-transitory computer-readable storage medium of claim 19, the one or more programs further including instructions for:
prior to completing the process for sharing the set of health-related data, displaying a summary user interface, wherein the summary user interface includes indications of the data types that have been selected to be included in the set of health-related data for sharing upon completion of the process for sharing the set of health-related data.

35. The non-transitory computer-readable storage medium of claim 34, wherein the summary user interface includes an eleventh selectable user interface object, the one or more programs further including instructions for:
receiving an input corresponding to the eleventh selectable user interface object; and
in response receiving the input corresponding to the eleventh selectable user interface object, displaying a preview user interface, wherein the preview user interface includes a graphical preview of the set of health-related data as it would be presented to a designated recipient of the set of health-related data after completion of the process for sharing the set of health-related data.

36. The non-transitory computer-readable storage medium of claim 34, wherein the summary user interface includes a twelfth selectable user interface object that when selected, enables modification of the data types that have been selected to be included in the set of health-related data for sharing upon completion of the process for sharing the set of health-related data.

37. The non-transitory computer-readable storage medium of claim 19, the one or more programs further including instructions for:

during the process for sharing the set of health-related data or after completion of the process for sharing the set of health-related data, displaying a thirteenth user selectable user interface object that, when selected, initiates a process to request health-related data from a second designated recipient of the set of health-related data.

38. The non-transitory computer-readable storage medium of claim 19, the one or more programs further including instructions for:

completing the process for sharing the set of health-related data, wherein the process for sharing the set of health-related data causes a first set of health-related data to be shared with a third designated recipient; and completing a second process for sharing a second set of health-related data, wherein:

the second process for sharing the second set of health-related data causes the second set of health-related data to be shared with a fourth designated recipient; and the first set of health-related data includes different data types than those includes in the second set of health-related data.

39. The non-transitory computer-readable storage medium of claim 19, wherein the first data type corresponds to a first health-related measurement and the second data type corresponds to a second health-related measurement.

40. The method of claim 20, wherein the first set of criteria includes a criterion that is satisfied when the first data type includes user data that was created or modified within a predetermined time period.

41. The method of claim 20, further comprising:

while displaying the first selectable user interface object and/or displaying the second selectable user interface object, receiving a third set of one or more inputs;

in response to receiving the third set of one or more inputs:

completing the process for sharing the set of health-related data; and sharing the set of health-related data with at least one external computer system, wherein:

in accordance with a determination that the second set of one or more inputs includes a first input that corresponds to selection of the first selectable user interface object that corresponds to the first data type, the set of health-related data that is shared includes shared data of the first data type; and in accordance with a determination that the second set of one or more inputs includes a second input that corresponds to selection of the second selectable user interface object that corresponds to the second data type, the set of health-related data that is shared includes shared data of the second data type.

42. The method of claim 20, wherein:

the first data type is selected from the group consisting of: user-entered data, data collected by one or more sensors that are in communication with the computer system, data transmitted by one or more external devices, and a combination thereof.

43. The method of claim 20, wherein the first data type and the second data type satisfy a first set of grouping criteria, the method further comprising:

after displaying the first data selection user interface, displaying a second user selection user interface that includes:

a fourth selectable user interface object that corresponds to a third data type and that, when selected, modifies the sharing status of the third data type in the process for sharing the set of health-related data, wherein the third data type satisfies a second set of grouping criteria but does not satisfy the first set of grouping criteria; and a fifth selectable user interface object that corresponds to a fourth data type and that, when selected, modifies the sharing status of the fourth data type in the process for sharing the set of health-related data, wherein the fourth data type satisfies the second set of grouping criteria but does not satisfy the first set of grouping criteria.

44. The method of claim 43, further comprising:

prior to displaying the first data selection user interface, displaying a sixth selectable user interface object;

receiving a fourth set of one or more user inputs that includes an input corresponding to the sixth selectable user interface object; and in response to receiving the fourth set of one or more user inputs, displaying a third data selection user interface that includes:

a seventh selectable user interface object that corresponds to the first data type and that, when selected, modifies the sharing status of the first data type in the process for sharing the set of health-related data; and an eighth selectable user interface object that corresponds to the third data type and that, when selected, modifies the sharing status of the third data type in the process for sharing the set of health-related data.

45. The method of claim 43, wherein the first data selection user interface includes an ninth selectable user interface object, the method further comprising:

receiving a user input corresponding to the ninth selectable user interface object; and in response to receiving the user input corresponding to the ninth selectable user interface object:

displaying a tenth selectable user interface object that corresponds to a fifth data type and that, when selected, modifies the sharing status of the fifth data type in the process for sharing the set of health-related data, wherein:

the fifth data type satisfies the first set of grouping criteria; and the fifth data type does not satisfy the first set of criteria.

46. The method of claim 20, wherein the first selectable user interface object and the second selectable user interface object are independently selectable to modify the sharing status of the respective data type.

47. The method of claim 20, further comprising:

after displaying the first data selection user interface and before completing the process for sharing the set of health-related data, displaying a third data selection user interface that includes:

a first laboratory results selectable user interface object that corresponds to a first laboratory results data type and that, when selected, modifies the sharing status of the first laboratory results data type in the process for sharing the set of health-related data; and a second laboratory results selectable user interface object that corresponds to a second laboratory results data type and that, when selected, modifies the sharing status of the second laboratory results data type in the process for sharing the set of health-related data.

48. The method of claim 47, wherein the first laboratory results selectable user interface object and the second laboratory results selectable user interface object are independently selectable to modify the sharing status of the respective type of laboratory results data.

49. The method of claim 47, wherein the third data selection user interface includes a eleventh selectable user interface object, the method further comprising:

receiving a user input corresponding to selection of the eleventh selectable user interface object; and in response to the user input corresponding to selection of the eleventh selectable user interface object, displaying a confirmation user interface that includes a confirmation selectable user interface object that, when selected, modifies the sharing status for all laboratory results data types.

50. The method of claim 20, further comprising:

prior to displaying the first data selection user interface, displaying a contact selection user interface that includes:

a first contactable user selectable user interface object that satisfies a set of contact grouping criteria and that, when selected, designates a first contactable user as a recipient for the set of health-related data; and a second contactable user selectable user interface object that satisfies the set of contact grouping criteria and that, when selected, designates a second contactable user as a recipient for the set of health-related data.

51. The method of claim 50, wherein:

the process for sharing the set of health-related data includes designating a single contactable user to receive the set of health-related data; and both the first contactable user and the second contactable user cannot be, via the contact selection user interface, concurrently designated as recipients for the set of health-related data.

52. The method of claim 20, further comprising:

prior to completing the process for sharing the set of health-related data, displaying a summary user interface, wherein the summary user interface includes indications of the data types that have been selected to be included in the set of health-related data for sharing upon completion of the process for sharing the set of health-related data.

53. The method of claim 52, wherein the summary user interface includes an eleventh selectable user interface object, the method further comprising:

receiving an input corresponding to the eleventh selectable user interface object; and in response receiving the input corresponding to the eleventh selectable user interface object, displaying a preview user interface, wherein the preview user interface includes a graphical preview of the set of health-related data as it would be presented to a designated recipient of the set of health-related data after completion of the process for sharing the set of health-related data.

54. The method of claim 52, wherein the summary user interface includes a twelfth selectable user interface object that when selected, enables modification of the data types that have been selected to be included in the set of health-related data for sharing upon completion of the process for sharing the set of health-related data.

55. The method of claim 20, further comprising:

during the process for sharing the set of health-related data or after completion of the process for sharing the set of health-related data, displaying a thirteenth user selectable user interface object that, when selected, initiates a process to request health-related data from a second designated recipient of the set of health-related data.

56. The method of claim 20, further comprising:

completing the process for sharing the set of health-related data, wherein the process for sharing the set of health-related data causes a first set of health-related data to be shared with a third designated recipient; and completing a second process for sharing a second set of health-related data, wherein:

the second process for sharing the second set of health-related data causes the second set of health-related data to be shared with a fourth designated recipient; and the first set of health-related data includes different data types than those includes in the second set of health-related data.

57. The method of claim 20, wherein the first data type corresponds to a first health-related measurement and the second data type corresponds to a second health-related measurement.

58. The computer system of claim 1, wherein the plurality of sensors are enabled to detect a plurality of health-related data types consisting of heart rate data, blood oxygen data, blood pressure data, fall detection data, and steps data.

59. The non-transitory computer-readable storage medium of claim 19, wherein the plurality of sensors are enabled to detect a plurality of health-related data types consisting of heart rate data, blood oxygen data, blood pressure data, fall detection data, and steps data.

60. The method of claim 20, wherein the plurality of sensors are enabled to detect a plurality of health-related data types consisting of heart rate data, blood oxygen data, blood pressure data, fall detection data, and steps data.

* * * * *